(12) United States Patent
Teran et al.

(10) Patent No.: US 11,241,502 B2
(45) Date of Patent: Feb. 8, 2022

(54) STABLE COMPOSITIONS OF PEGYLATED CARFILZOMIB COMPOUNDS

(71) Applicant: AMGEN INC., Thousand Oaks, CA (US)

(72) Inventors: Alona Teran, Moorpark, CA (US); William Callahan, Thousand Oaks, CA (US); Qahera Munaim, Chatsworth, CA (US); Rahul Kaushik, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 16/192,469

(22) Filed: Nov. 15, 2018

(65) Prior Publication Data
US 2019/0142957 A1     May 16, 2019

Related U.S. Application Data

(60) Provisional application No. 62/587,070, filed on Nov. 16, 2017.

(51) Int. Cl.
| | |
|---|---|
| *A61K 47/60* | (2017.01) |
| *A61K 38/07* | (2006.01) |
| *A61K 47/26* | (2006.01) |
| *A61P 35/00* | (2006.01) |
| *A61K 47/02* | (2006.01) |
| *A61K 9/00* | (2006.01) |
| *A61K 47/18* | (2017.01) |
| *A61K 9/19* | (2006.01) |
| *A61K 47/42* | (2017.01) |
| *A61K 47/12* | (2006.01) |
| *A61K 9/08* | (2006.01) |

(52) U.S. Cl.
CPC ............ *A61K 47/60* (2017.08); *A61K 9/0019* (2013.01); *A61K 9/08* (2013.01); *A61K 9/19* (2013.01); *A61K 38/07* (2013.01); *A61K 47/02* (2013.01); *A61K 47/12* (2013.01); *A61K 47/183* (2013.01); *A61K 47/26* (2013.01); *A61K 47/42* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 7,417,042 | B2 | 8/2008 | Smyth et al. |
| 7,737,112 | B2 | 6/2010 | Lewis et al. |
| 10,022,326 | B2 | 7/2018 | Chu et al. |
| 10,517,954 | B2 * | 12/2019 | Luehr ............... A61K 47/60 |
| 10,675,353 | B2 * | 6/2020 | Luehr ............ C08G 65/33396 |
| 2005/0245435 | A1 | 11/2005 | Smyth et al. |
| 2013/0150289 | A1 | 6/2013 | Phiasivongsa et al. |
| 2013/0303482 | A1 | 11/2013 | Lewis et al. |
| 2014/0073583 | A1 * | 3/2014 | Hippalgaonkar .... C07D 405/12 |
| 2014/0100154 | A1 | 4/2014 | Phiasivongsa et al. |
| 2014/0100168 | A1 * | 4/2014 | Phiasivongsa .......... A61P 33/02 514/16.7 |
| 2015/0209281 | A1 | 7/2015 | Chu et al. |
| 2017/0340746 | A1 * | 11/2017 | Luehr ................. A61K 9/0053 |

FOREIGN PATENT DOCUMENTS

CN       105 924 500       9/2016

OTHER PUBLICATIONS

Shpilberg et al. ("Subcutaneous administration of rituximab (MabThera) and trastuzumab (Herceptin) using hyaluronidase," British Journal of Cancer (2013) 109, 1556-1561) (Year: 2013).*
FDA Label for Rituxan Hycela™ (rituximab and hyaluronidase human) injection (published Jun. 2017 at fda.gov) (Year: 2017).*
Apr. 23, 2020, U.S. Appl. No. 16/857,111.
Nov. 5, 2019, U.S. Appl. No. 16/675,134, U.S. Pat. No. 10,675,353.
May 23, 2017, U.S. Appl. No. 15/602,823, U.S. Pat. No. 10,517,954.
Dec. 22, 2011, U.S. Appl. No. 13/334,263, U.S. Pat. No. 8,207,124.
Dec. 22, 2011, U.S. Appl. No. 13/334,466, U.S. Pat. No. 8,207,126.
Dec. 22, 2011, U.S. Appl. No. 13/334,288, U.S. Pat. No. 8,207,125.
Dec. 22, 2011, U.S. Appl. No. 13/334,372, U.S. Pat. No. 8,324,174.
Dec. 22, 2011, U.S. Appl. No. 13/334,469, U.S. Pat. No. 8,207,297.
Dec. 22, 2011, U.S. Appl. No. 13/334,544, U.S. Pat. No. 8,207,127.
Apr. 11, 2007, U.S. Appl. No. 11/786,217, U.S. Pat. No. 7,491,704.
Apr. 14, 2005, U.S. Appl. No. 11/106,879, U.S. Pat. No. 7,232,818.
Apr. 14, 2005, U.S. Appl. No. 11/578,626, U.S. Pat. No. 8,129,346.
Aug. 8, 2005, U.S. Appl. No. 11/199,899, U.S. Pat. No. 7,417,042.
Jun. 26, 2020, U.S. Appl. No. 16/912,806.
Aug. 8, 2005, U.S. Appl. No. 11/658,983, U.S. Pat. No. 8,198,270.
Dec. 7, 2005, U.S. Appl. No. 11/299,265, U.S. Pat. No. 7,737,112.
Feb. 1, 2013, U.S. Appl. No. 13/757,148, U.S. Pat. No. 8,921,324.
Feb. 1, 2013, U.S. Appl. No. 13/757,113, U.S. Pat. No. 8,921,583.
Oct. 3, 2008, U.S. Appl. No. 12/287,043, U.S. Pat. No. 8,367,617.
Jul. 17, 2013, U.S. Appl. No. 14/414,568, U.S. Pat. No. 10,022,326.
Sep. 30, 2013, U.S. Appl. No. 14/041,953, U.S. Pat. No. 9,315,542.
Mar. 9, 2016, U.S. Appl. No. 15/065,347, U.S. Pat. No. 9,878,047.
Jan. 29, 2018, U.S. Appl. No. 15/881,919, U.S. Pat. No. 10,682,419.
Jul. 9, 2013, U.S. Appl. No. 13/938,160, U.S. Pat. No. 9,309,283.
International Search Report for PCT/US2018/061346, dated Mar. 1, 2013.
Written Opinion for PCT/US2018/061346, dated Mar. 1, 2013.

* cited by examiner

*Primary Examiner* — Christina Bradley

(57) ABSTRACT

The present invention provides stable pharmaceutical compositions of pegylated carfilzomib compounds, methods for preparing the compositions, and uses of the compositions for treating cancer, including hematologic malignancies such as multiple myeloma. The compositions can be stored in frozen form or lyophilized to dry solid form.

21 Claims, 5 Drawing Sheets

Figures 3-A and 3-B
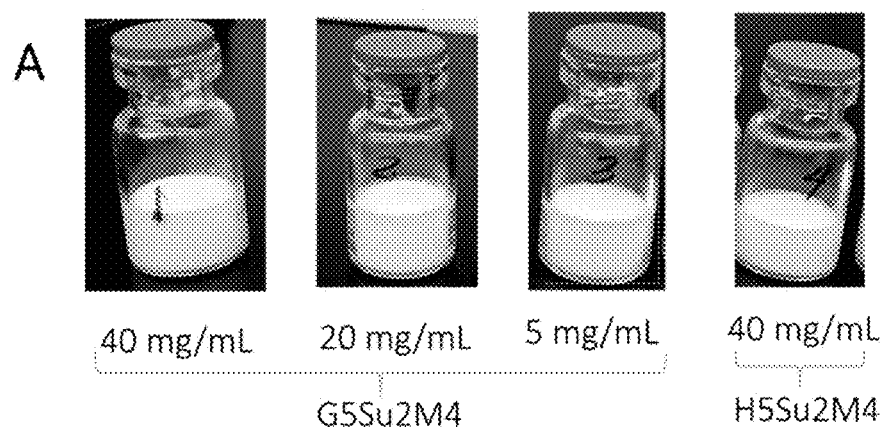
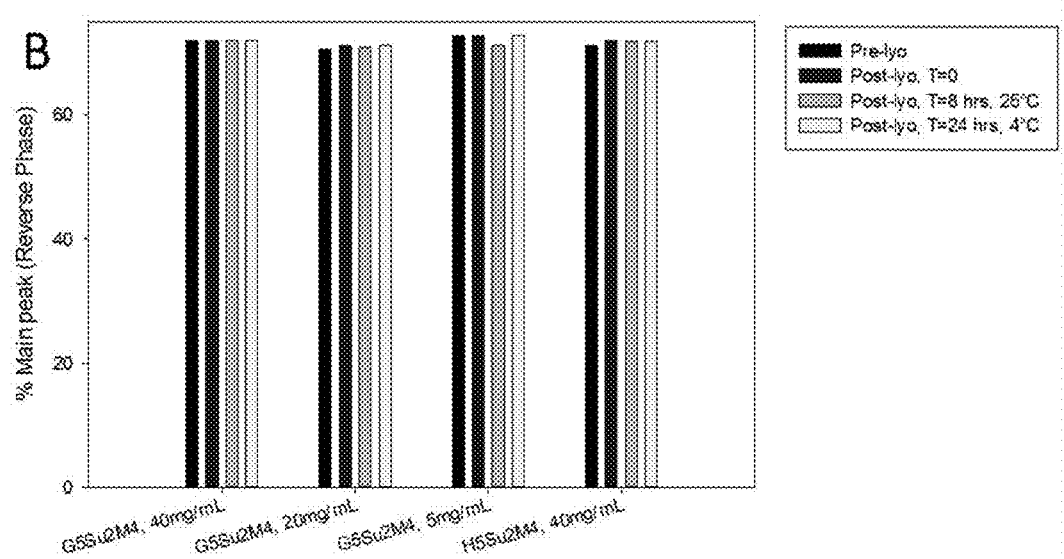

Figures 4-A and 4-B
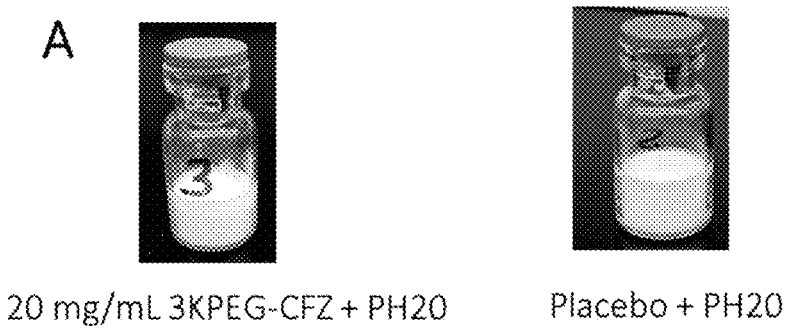
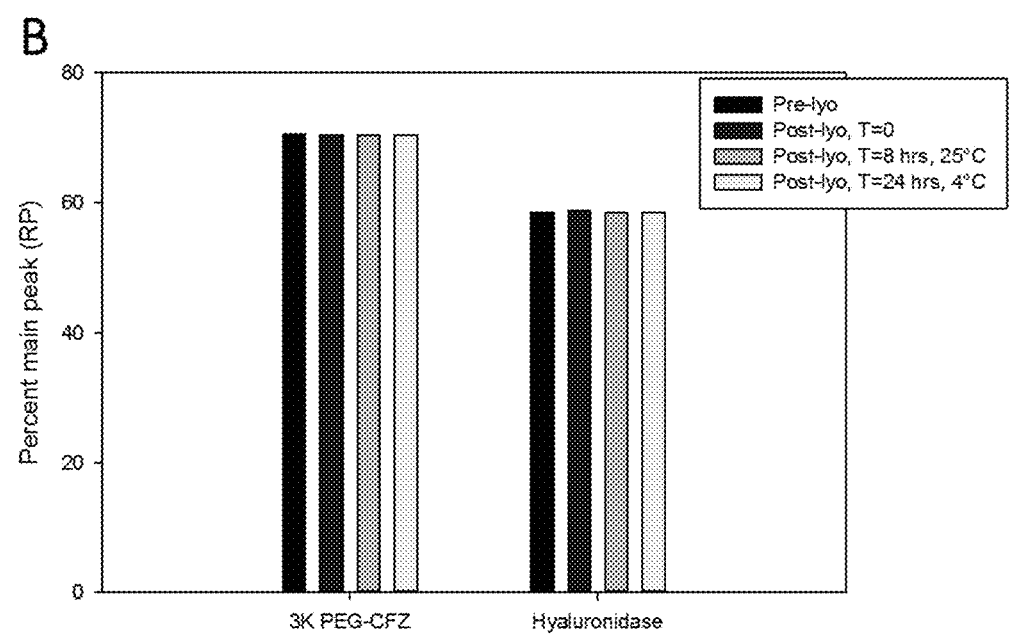

Figures 5-A and 5-B
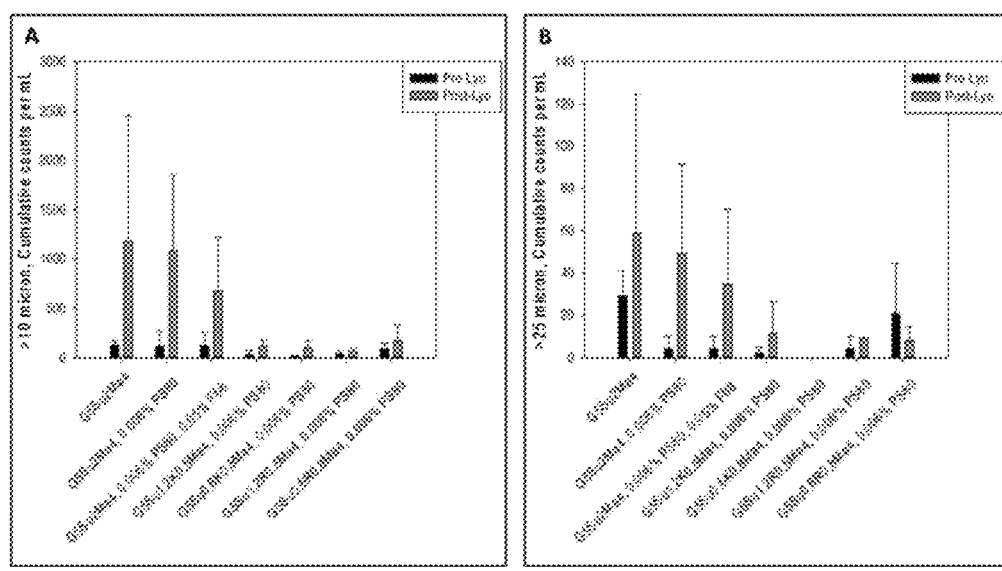

STABLE COMPOSITIONS OF PEGYLATED CARFILZOMIB COMPOUNDS

This application claims the benefit of U.S. Provisional Application No. 62/587,070, filed 16 Nov. 2017 which specification is hereby incorporated here in by reference in its entirety.

FIELD OF THE INVENTION

The present invention relates to stable pharmaceutical compositions of pegylated carfilzomib compounds, methods for preparing the compositions, and uses thereof for treating cancer including hematologic malignancies, such as multiple myeloma, and solid tumors.

BACKGROUND OF THE INVENTION

Cancer is one of the most widespread diseases and a leading cause of death worldwide. In the United States alone, cancer is the second leading cause of death, surpassed only by heart disease. Cancer is often characterized by deregulation of normal cellular processes or unregulated cell proliferation.

Multiple myeloma (MM) is a progressive and malignant neoplastic type of cancer originating from plasma cells. It is characterized by abnormal accumulation of malignant plasma cells within bone marrow, and it accounts for approximately 13% of all hematologic cancers (Palumbo and Anderson, 2011). In 2015, about 26,850 new cases were expected to be diagnosed with MM, and about 11,240 people were expected to die from the disease in the United States (ACS, 2015). The incidence of MM has increased steadily due to increased life expectancy of the general population in the United States (Warren et al., 2013). The disease most commonly affects the elderly population, with the median age of incidence around 69 years old (Howlander et al., 2013; ACS, 2015).

The therapeutic goals of management of MM are to provide symptomatic relief, achieve disease control and provide prolonged remissions (Kurtin, 2013). Conventionally, a combination of high dose chemotherapeutic agents (melphalan, vincristine, cyclophosphamide, doxorubicin, liposomal doxorubicin, bendamamustine) followed by autologous stem-cell transplantation (ASCT) has been utilized to treat young, treatment-naïve and medically fit patients (less than 65 years of age) (Palumbo et al., 2011). Age, comorbid conditions and geriatric assessment are the major criteria for deciding patients' eligibility to tolerate high-dose therapy (HDT) followed by ASCT (Palumbo et al., 2014). For elderly patients ineligible for HDT and ASCT, melphalan plus prednisone had been the standard therapy for several decades (Palumbo et al., 2011; Rodriguez et al., 2012). During the last decade, treatment algorithm of MM underwent a paradigm change with the introduction of novel immunomodulatory agents (such as thalidomide, lenalidomide, and pomalidomide) and targeted proteasome inhibitors (bortezomib and carfilzomib) (Richardson et al., 2007; Dmoszynska, 2008; Gupta et al., 2013).

Carfilzomib is a tetrapeptide epoxy ketone proteasome inhibitor that binds selectively and irreversibly to the constitutive proteosome and immunoproteosome. More specifically, the epoxyketone electrophilic warhead binds to the catalytic threonine residue of the β5 subunit of the proteasome protein. CFZ is well tolerated with acceptable toxicity profile. Carfilzomib, polymorphic forms, methods of making, formulations, its use and other carfilzomib attributes are described in US20050245435, US20140105921 and PCT publications WO2006017842, WO2009045497, WO2014169897, WO2013169282, WO2014011695, WO2006063154, WO2014015016, and WO2010048298, each specification of which is hereby incorporated herein by reference in its entirety.

Carfilzomib has shown an encouraging overall response rates, progression free survival (PFS) and overall survival (OS) in patients with relapsed and refractory MM and with newly diagnosed patients with MM. Carfilzomib was first approved (as Kyprolis®) for treatment in patients with relapsed and refractory MM in July 2012 as a single agent therapy. More recently Kyprolis was approved in combination with lenalidomide and dexamethasone (July 2015) and in combination with dexamethasone (January 2016) for the treatment of patients with relapsed and refractory MM who have received one to three lines of therapy. The approved treatment regimen for carfilzomib is to administer it to the patient by infusion, either over a short 10 minute period or over a slower, longer 30 minute duration of time. This infusion is to occur for 2 consecutive days per week for three consecutive weeks in a 28 day cycle. Thus, to comply with this treatment schedule, patients need to drive or be driven two times per week on consecutive days to an authorized Kyprolis® administration center, such as a doctor's office, a clinic or a hospital, where it can be properly and safely administered. This may be inconvenient or impractical, or may simply be a burden to some patients. This burden increases the likelihood of reduced or decreased compliance with, or even complete non-compliance of, the full and complete course of the prescribed Kyprolis® therapeutic regimen.

Carfilzomib is rapidly metabolized and cleared in humans. Carfilzomib, a small tetrapeptide compound, exhibits a short half-life in-vivo of about 60 minutes or less in humans. One mechanism of carfilzomib clearance is via hepatic blood flow, resulting in the relatively brief half-life for carfilzomib. Drug products possessing short half lives or rapid clearance in general tend to exhibit reduced target coverage leading to decreased and/or shortened biological inhibitory activity. To overcome such shortfalls, additional drug is typically administered to provide more drug and prolonged efficacy at the biological site of action. Hence, both the rapid clearance and the twice weekly frequency of dosing of carfilzomib leave room for possible improvements in efficacy, delivery and/or patient compliance.

Carfilzomib, as currently approved (Kyprolis®), is a sterile lyophilized amorphous solid formulation comprising sulfabutylether beta cyclodextrin (SBECD) and a sodium citrate buffer. Immediately prior to administration, the lyophilate is reconstituted with sterile water, and infused or injected into the patient. The SBECD excipient acts primarily as a solubilizing additive for carfilzomib, and forms a complex with carfilzomib thereby improving carfilzomib water solubility.

History has revealed that attempts to solve weaknesses of drug products and/or to improve upon delivery, use or there aspects of a given drug product, have led to the preparation of alternative forms of these active pharmaceutical ingredients (API or medicinal compounds) and/or new formulations of them. Some alternative compound forms have included discovery of pro-drugs, designed to enhance the pK and/or PD properties of the API. For instance, Greenwald et al disclose Prodrugs of Amine Containing Compounds (*J. Med Chem.*, 1999, 42, 3657-3667). WO2005063777 discloses benzylphosphate and substituted benzylphosphate prodrugs for the treatment of pulmonary inflammation.

WO20090152160 discloses inhaled carbaprotacyclin and prostacyclin prodrugs for the treatment of arterial hypertension. US patent publication no. 20040100225 discloses acyloxymethyl pro-drugs of imatinib (Gleevec®). Also, PCT publication WO2011084846 discloses acyloxymethyl pro-drugs of risperidone. These pro-drug disclosures teach alkyl-acyloxymethyl linked pro-drugs.

Modifications to carfilzomib have also been made to improve upon its properties or other attributes as an active pharmaceutical ingredient and drug product. US patent application publication no. US20140105921 describes carfilzomib and other epoxyketone proteasome inhibitor pro-drugs having an acyloxymethyl linker connecting the inhibitor to polyethylene glycol units (PEG). However, these carfilzomib pro-drug compounds have been found to release quinone methide byproducts during metabolism in vivo, which may be potentially toxic and may present a human safety risk. It is desirable to identify formulations and/or pharmaceutical compositions of modified carfilzomib compounds to suitably deliver them to patients while maintaining or possibly improving the stability, shelf-life, efficacy and/or safety of the currently approved carfilzomib treatments.

BRIEF DESCRIPTION OF THE INVENTION

The present invention provides novel pharmaceutical compositions of pegylated carfilzomib compounds, i.e., stable formulations of peg-carfilomib, that deliver therapeutic anti-cancer benefits to the patient while maintaining comparable or longer carfilzomib plasma concentrations and exposure to the proteasome protein. To this end, the formulations of the present invention provide proteosomal inhibitory activity comparable to that of the currently approved carfilzomib cyclodextrin IV formulation. The present invention further provides pegylated carfilzomib formulations that do not include use of a cyclodextrin as a carfilzomib solubilizing agent.

Particularly, the present invention provides stable, isotonic, cyclodextrin free, lyophilized and liquid formulations of pegylated carfilzomib compounds. The solid lyophilized formulations may be reconstituted, such as with sterile water, and administered via parenteral methods including intravenous administration, injection and also via sub-cutaneous administration. These formulations are useful to treat various types of cancer, including without limitation, multiple myeloma. More particularly, the formulations provided herewith maintain or exhibit suitable bioavailability. The present invention further provides a method of preparing the pharmaceutical compositions, and methods of administering the compositions, such as parenterally by infusion or injection, or subcutaneously, for treating various forms of cancer such as multiple myeloma.

In one aspect, the invention provides a pharmaceutical composition comprising (a) a pegylated carfilzomib compound; (b) at least one excipient selected from the group consisting of sucrose, sorbital, glycerin, maltose, lactose, erythrose, dextrose, lactobiose, cyclodextrin, proline, glycine, arginine, histidine, aspartic acid, valine, leucine, alanine, methionine, proline, glutamic acid, glutamate, and a salt selected from the group consisting of sodium chloride, potassium chloride, ammonium sulfate, potassium chlorate, calcium chloride, zinc chloride, guanidine hydrochloride, ammonium chloride, potassium sulfate, ammonium aspartate, arginine-HCl, lysine-HCl, magnesium chloride and barium sulfate; (c) a buffering agent selected from the group consisting of glutamate, histidine, acetate, and Tris-HCl, or a combination thereof; and (d) optionally a bulking agent selected from the group consisting of mannitol, trehalose, PVP, cyclodextrin, glycine, dextrose, dextran, sucrose, proline, PEG 33350 and PEG 400, (e) optionally an amino acid selected from the group consisting of lysine, arginine, histidine, aspartic acid, valine, leucine, alanine, methionine, proline, glutamic acid and glutamate, (f) optionally a surfactant selected from the group consisting of polysorbate 20, polysorbate 80, pluronic F68, docusate sodium, benzaconium chloride, triton X100, tetrafunctional block O polymers, alcohols, SDS, protamine sulfate and butane, or a combination of (d), (e) and (f). The pharmaceutical compositions of the present invention provide suitable solubility, permeability, pharmacokinetics (pK) and/or pharmacodynamics (PD) properties to the pegylated carfilzomib compounds when compared with the corresponding approved carfilzomib product.

The pharmaceutical compositions provided by the present invention further provide potential drug product benefits including, without limitation, shelf stability, storage capability, safe use after a number of days as a liquid preparation, frozen formulations, dry lyophilized formulations, and other conveniences for the safe maintenance, storage and use of a carfilzomib based drug product. The improved compostions of the present invention facilitate various modes of administration, such as for example intravenously by infusion or injection. The compositions can also be administered subcutaneously under the skin. The invention also provides compositions including hyaluronidase, which may facilitate subcutaneous administration. The compositions are useful for treating cancers, including without limitation, multiple myeloma and solid tumors.

BRIEF DESCRIPTION OF THE FIGURES

FIG. 3-A is a depiction of the resulting lyophilization cakes obtained from formulations G5Su2M4 (3) and H5Su2M4 (1) with 3K pegylated carfilzomib—example 28 herein;

FIG. 3-B is a bar graph displaying the % API (3K pegylated carfilzomib—example 28 herein) remaining as measured by reverse phase chromatography in each of the 4 lyophilized cakes in FIG. 3-A above;

FIG. 4-A is a depiction of the resulting lyophilization cake obtained from a formulation of G5Su2M4+0.006% polysorbate 80+2000 units/mL of hyaluronidase with 3K pegylated carfilzomib—example 28 herein;

FIG. 4-B is a depiction of the resulting lyophilization cake obtained from a placebo comparator formulation with only hyaluronidase;

FIG. 5-A is a bar graph depicting >10 micron particle counts in pre- and post lyophilization exemplary formulations of Table 5 as measured by subvisible light obscuration; and FIG. 5-B is a bar graph depicting >25 micron particle counts in pre- and post lyophilization exemplary formulations of Table 5 as measured by subvisible light obscuration;

DETAILED DESCRIPTION OF THE INVENTION

Figure 1:
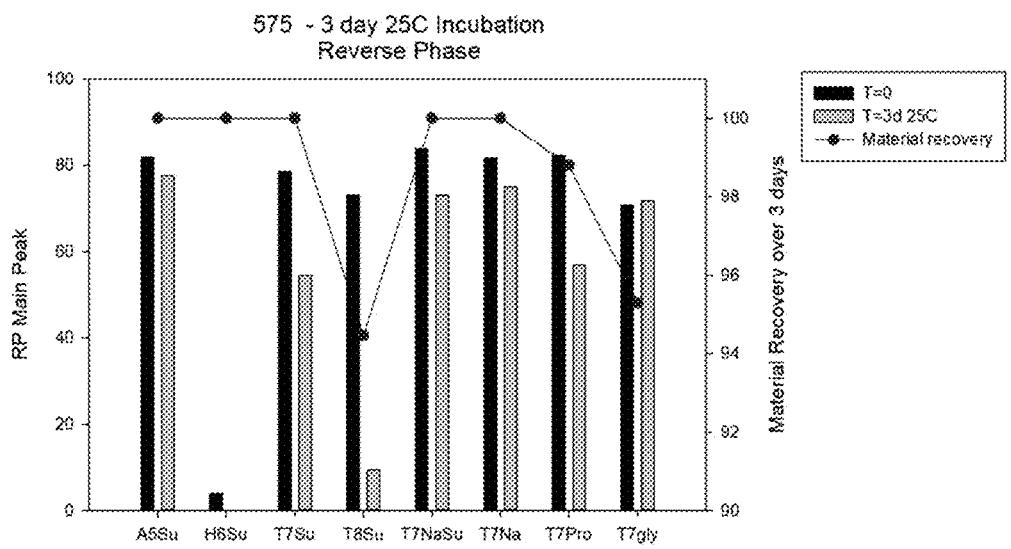
FIG. 1 is a bar graph displaying the % API (5K pegylated carfilzomib—example 34 herein) remaining as measured by reverse phase chromatography after storage at 25° C. for 3 days.

The present invention provides novel pharmaceutical compositions of pegylated carfilzomib compounds, processes for making these formulations, and uses of the compositions for the treatment of cancer, including treatment of hematologic malignancies such as multiple myeloma, lymphoma, leukemia, and treatment of other cancers such as solid tumors. Specifically, the formulations of the present invention are stable, without meaningful degradation of the active pharmaceutical ingredient, resulting in improved shelf life, clarity of solution, longevity and safety of the drug product. The invention provides compositions that are frozen formulations and compositions that are dry lyophilized formulations of pegylated carfilzomib compounds. These formulations are believed to possess API pharmacokinetic (pK) and/or pharmacodynamics (PD) properties comparable to, or improved over, that of the currently approved IV administered Kyprolis® (carfilzomib).

Carfilzomib is an epoxy ketone protease inhibitor described in U.S. Pat. Nos. 7,417,042 and 7,737,112, among others. The present invention provides formulations including pegylated carfilzomib compounds as the API. Exemplary pegylated carfilzomib compounds that may be included in the invention are generally and specifically described in International application no. PCT/US2017/03429. This PCT application has not published as of Nov. 24, 2017.

Representative pegylated carfilzomib compounds that may be included in the pharmaceutical compositions of the present invention are as follows.

In aspect 1 of the invention, the compositions include pegylated carfilzomib compounds of formula I linker is a moiety having the structure of

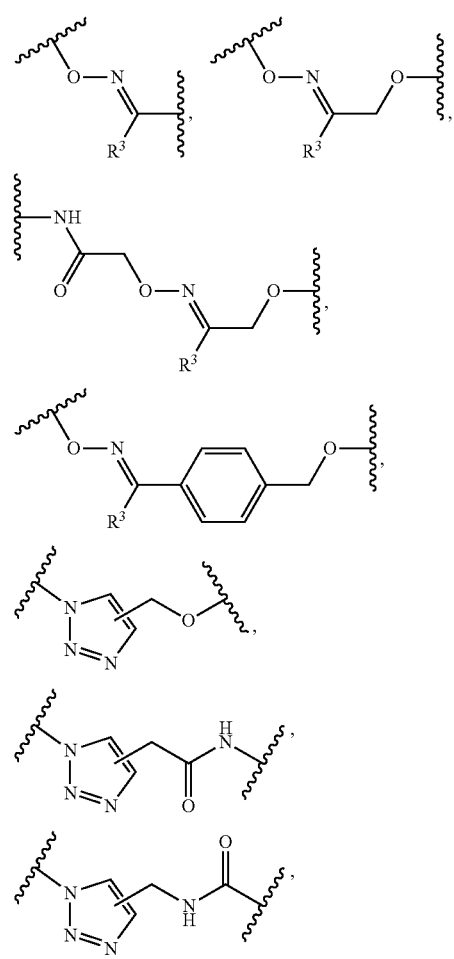

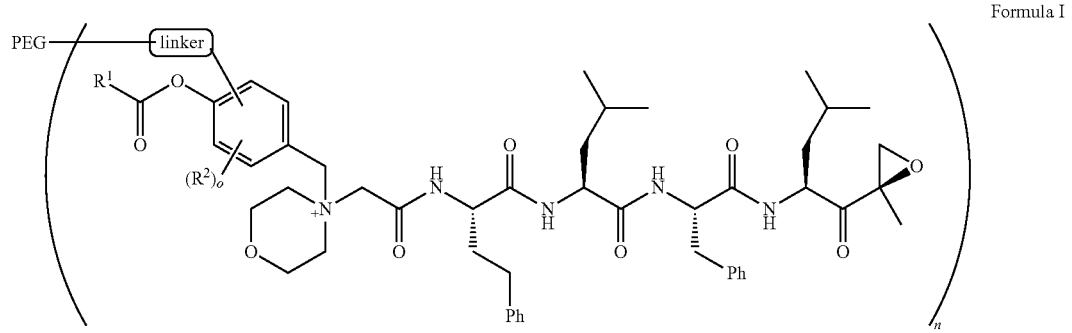

Formula I or a pharmaceutically acceptable salt thereof, wherein

R$^1$ is C$_{1-10}$alkyl or C$_{3-7}$cycloalkyl;

each R$^2$, independently, is C$_{1-6}$alkyl, —OCH$_3$ or halogen;

o is an integer selected from 0, 1, 2 or 3;

-continued

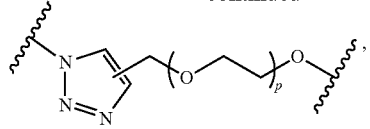

-continued

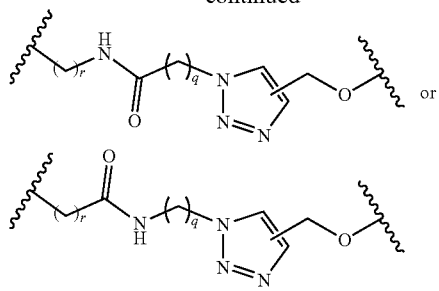   or

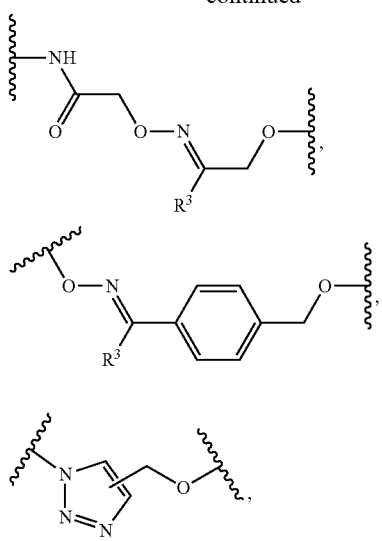

wherein R³ is H or CH₃;
n is an integer selected from 1, 2, 3 or 4;
p is an integer selected from 0, 1, 2, 3 or 4;
q is an integer selected from 1, 2, 3, 4, 5, 6, 7, 8 or 9;
r is an integer selected from 0, 1, 2, 3, 4 or 5; and
PEG is a polyethylene glycol polymeric moiety having a molecular weight ranging from about 500 to about 20,000.

In aspect 1a of the invention, the compositions include pegylated carfilzomib compounds of formula I

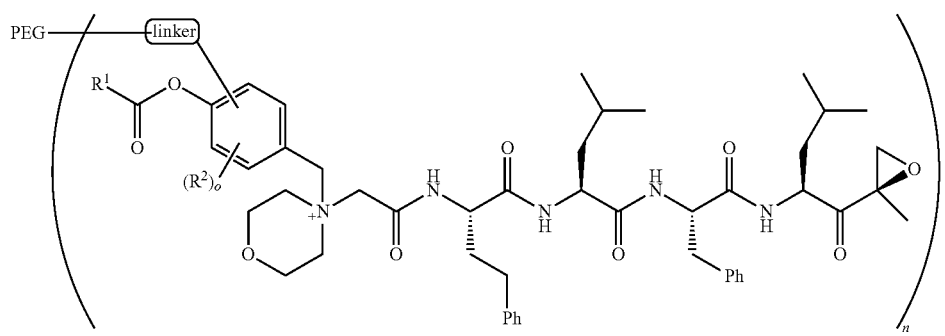

Formula I or a pharmaceutically acceptable salt thereof, wherein
R¹ is $C_{1-10}$alkyl or $C_{3-7}$cycloalkyl;
each R², independently, is $C_{1-6}$alkyl, —OCH₃ or halogen;
o is an integer selected from 0, 1, 2 or 3;
linker is a moiety having the structure of

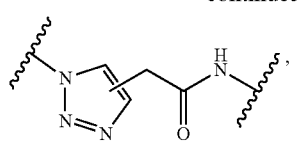

-continued

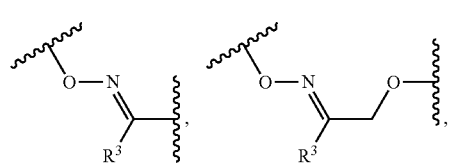

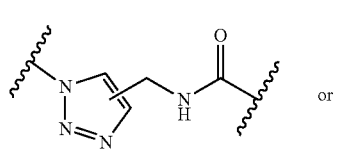   or

-continued

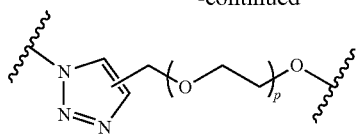

wherein R³ is H or CH₃; and
p is an integer selected from 0, 1, 2, 3 or 4;
n is an integer selected from 1, 2, 3 or 4; and
PEG is a polyethylene glycol polymeric moiety having a molecular weight ranging from about 500 to about 20,000.

In aspect 2 of the invention, the compositions include pegylated carfilzomib compounds of Formula II

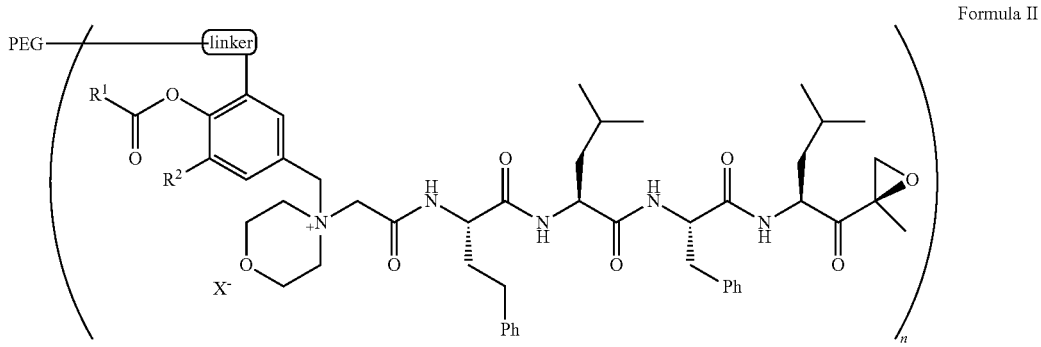

Formula II wherein
R¹ is $C_{1-10}$alkyl or $C_{3-7}$cycloalkyl;
R² is $C_{1-6}$alkyl, —OCH₃ or halogen;
linker is a moiety having the structure of

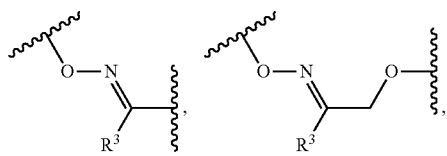

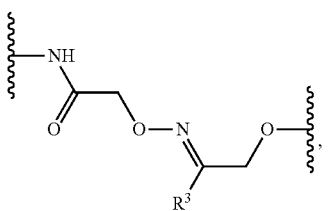

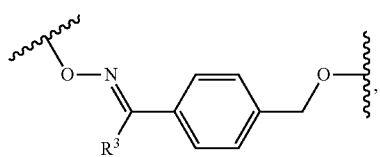

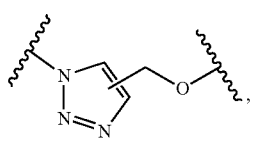

-continued

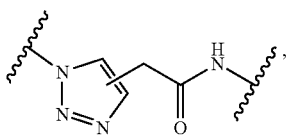

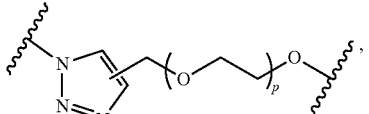

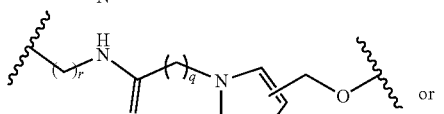

or

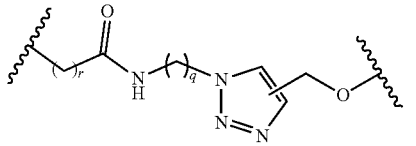

wherein R³ is H or CH₃;
n is an integer selected from 1, 2, 3 or 4;
p is an integer selected from 0, 1, 2, 3 or 4;
q is an integer selected from 1, 2, 3, 4, 5, 6, 7, 8 or 9;
r is an integer selected from 0, 1, 2, 3, 4 or 5;
X is a counter ion salt selected from a chloride, a bisulfate, a sulfate, a nitrate, a phosphate, an alky-sulfonate or an aryl-sulfonate; and
PEG is a polyethylene glycol polymeric moiety having a molecular weight ranging from about 2000 to about 20,000.

In aspect 3 of the invention, the compositions include pegylated carfilzomib compounds of aspects 1, 1a and 2 wherein R¹ is $C_{1-10}$alkyl.

In aspect 4 of the invention, the compositions include pegylated carfilzomib compounds of any one of aspects 1, 1a, 2 and 3 wherein each R², independently, is H, CH₃ or halogen.

In aspect 5 of the invention, the compositions include pegylated carfilzomib compounds of any one of aspects 1, 1a, 2, 3 and 4 wherein each $R^2$, independently, is H, $CH_3$, Cl or F.

In aspect 5a of the invention, the compositions include pegylated carfilzomib compounds of any one of aspects 1, 1a, 2, 3 and 4 wherein each $R^2$, independently, is H, $CH_3$ or F.

In aspect 6 of the invention, the compositions include pegylated carfilzomib compounds of any one of aspects 1, 1a, 2, 3, 4 and 5 wherein the linker is a moiety having the structure of

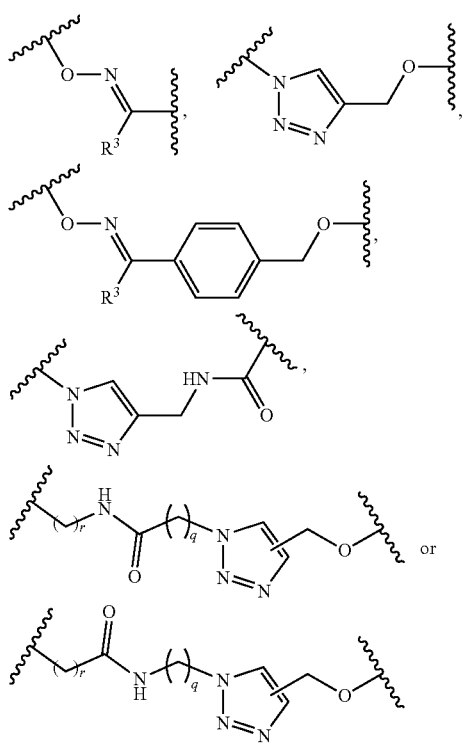

wherein $R^3$ is H or $CH_3$;
q is an integer selected from 1, 2, 3, 4 or 5; and
r is an integer selected from 0, 1, 2, 3 or 4.

In aspect 6a of the invention, the compositions include pegylated carfilzomib compounds of any one of aspects 1, 1a, 2, 3, 4 and 5 wherein the linker is a moiety having the structure of

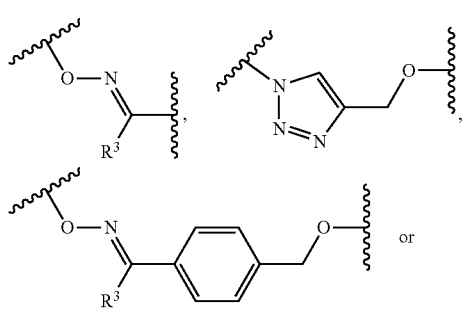

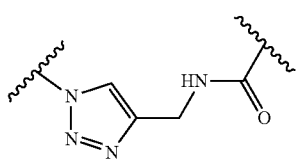

wherein $R^3$ is H or $CH_3$.

In aspect 7 of the invention, the compositions include pegylated carfilzomib compounds of an one of aspects 1, 1a, 2, 3, 4, 5 and 7 wherein the linker is

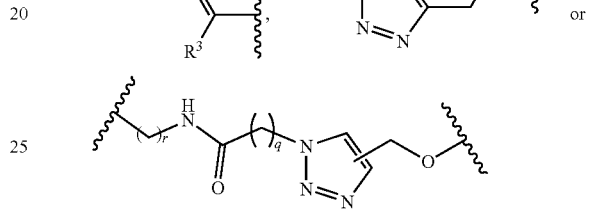

wherein $R^3$ is H or $CH_3$;
q is 4; and
r is 2.

In aspect 7a of the invention, the compositions include pegylated carfilzomib compounds of any one of aspects 1, 1a, 2, 3, 4, 5 and 7 wherein the linker is

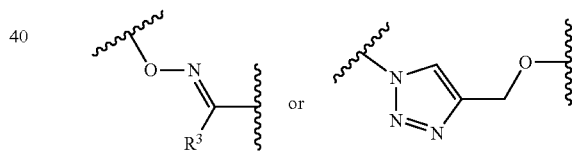

wherein $R^3$ is H or $CH_3$.

In aspect 8 of the invention, the compositions include pegylated carfilzomib compounds of any one of aspects 1, 1a, 2, 3, 4, 6, 6a, 7 and 7a wherein $R^3$ is H.

In aspect 9 of the invention, the compositions include pegylated carfilzomib compounds of any one of aspects 1-8 wherein $R^1$ is methyl, ethyl, propyl, isopropyl, butyl, t-butyl, pentyl, hexyl or heptyl.

In aspect 10 of the invention, the compositions include pegylated carfilzomib compounds of any one of aspects 1-9 wherein $R^1$ is methyl, ethyl, propyl, isopropyl, butyl, t-butyl, pentyl, hexyl or heptyl; and the linker is

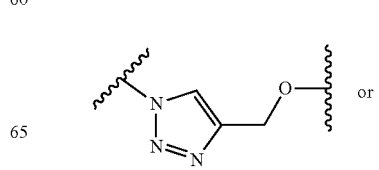

-continued

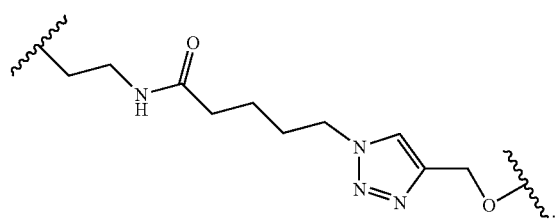

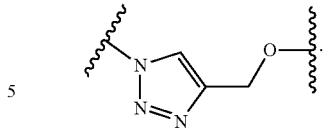

It should be noted that in aspects 1, 1a, 2 and aspects 3-10 that the term "or a pharmaceutically acceptable salt thereof" may include a counter ion salt of the quaternary nitrogen cationic charge, such as that illustrated in formula II of aspect 2, or those illustrated in aspects 11-24 hereinbelow. Further, it should be noted that it is intended that the term "any one of aspects 1-X" also include all sub-aspects of 1-X disclosed herein, including without limitation sub-aspects 1a, 5a, 6a, 7a and 10a.

In aspect 10a of the invention, the compositions include pegylated carfilzomib compounds of any one of aspects 1-9 wherein $R^1$ is methyl, ethyl, propyl, isopropyl, butyl, t-butyl, pentyl, hexyl or heptyl; and the linker is In aspect 11 of the invention, the compositions include pegylated carfilzomib compounds of any one of aspects 1-10, having the structure of

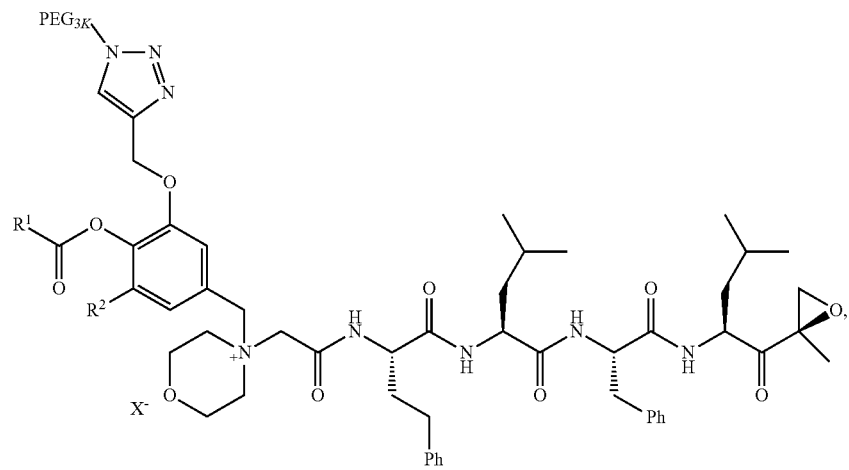

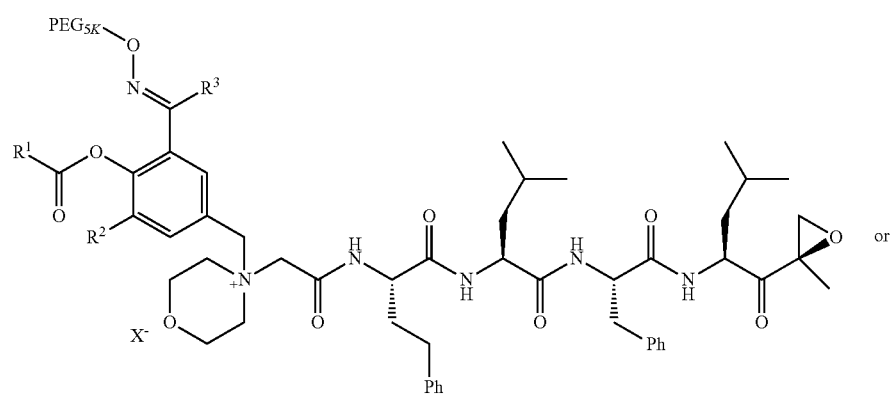

-continued

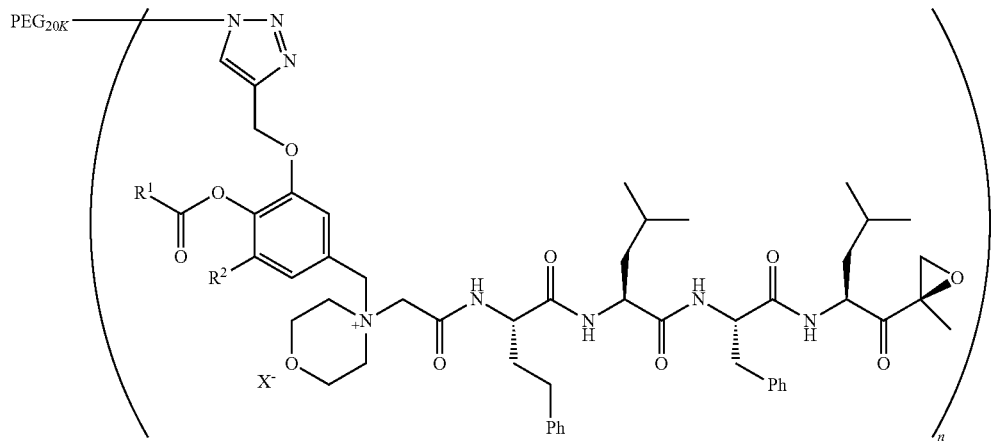

wherein R¹ is $C_{1-10}$alkyl;

R² is $C_{1-6}$alkyl, —OCH₃ or halogen;

R³ is H or CH₃;

X⁻ is a counter anion selected from chloride anion and a alkyl-sulfonate anion;

n is 4; and

PEG is a polyethylene glycol polymeric moiety having a molecular weight ranging from about 2000 to about 20,000.

In aspect 12 of the invention, the compositions include pegylated carfilzomib compounds of any one of aspects 1-11 wherein the compound is

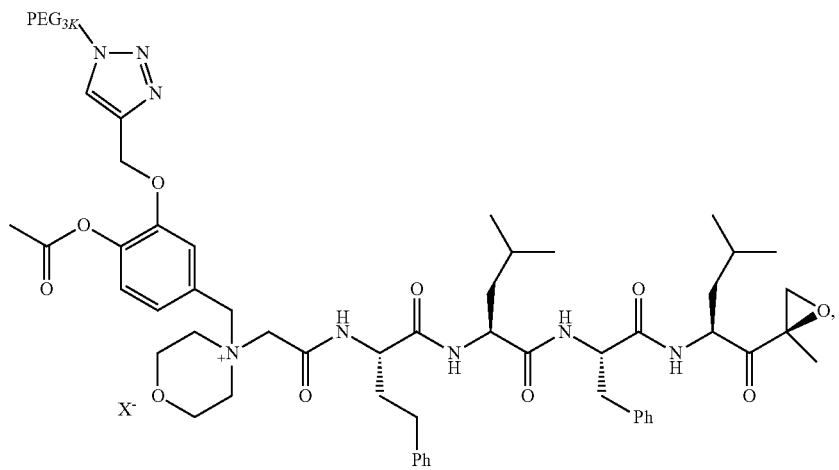

wherein X is a halide, a sulfonate or an alkyl-sulfonate counterion salt.

In aspect 12a of the invention, the compositions include pegylated carfilzomib compounds of any one of aspects 1-11 wherein the compound is

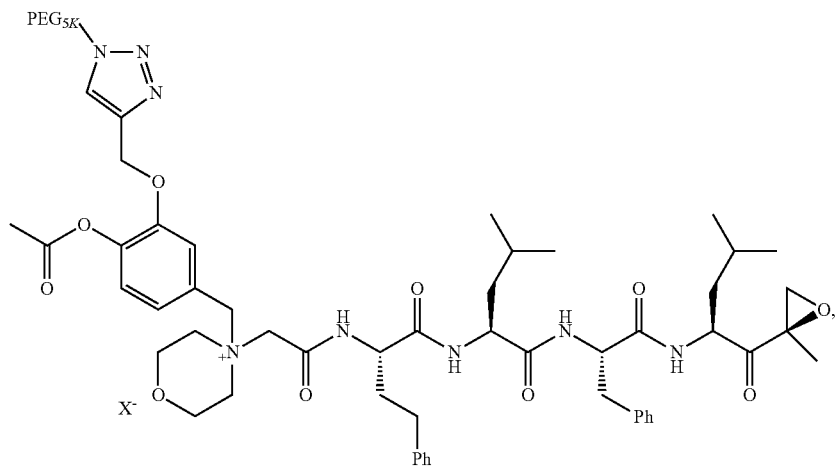

wherein X is a halide, a sulfonate or an alkyl-sulfonate counterion salt.

In aspect 13 of the invention, the compositions include pegylated carfilzomib compounds of any one of aspects 1-11 wherein the compound is

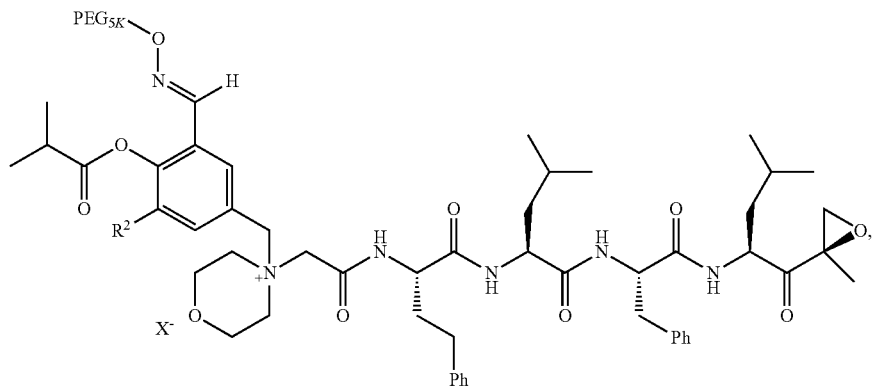

wherein X is a halide, a sulfonate or an alkyl-sulfonate counterion salt.

In aspect 14 of the invention, the compositions include pegylated carfilzomib compounds of any one of aspects 1-11 wherein the compound is wherein $R^3$ is H or $CH_3$; and PEG is a polyethylene glycol polymeric moiety having a molecular weight of 2000, 3000, 5000 or 20,000.

In aspect 16 of the invention, the compositions include pegylated carfilzomib compounds of aspect 15 wherein $R^1$ is

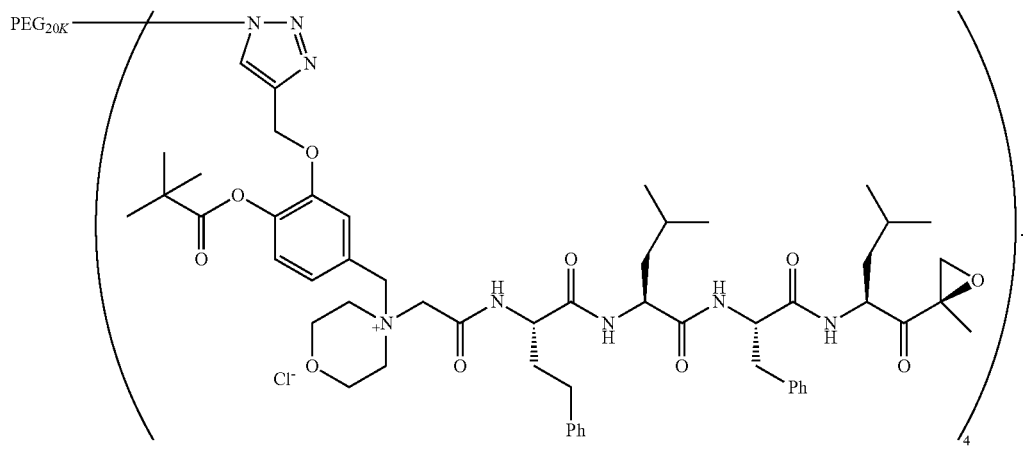

In aspect 15 of the invention, the compositions include pegylated carfilzomib compounds of any one of aspects 1 and 2 wherein $R^1$ is methyl, ethyl, propyl, isopropyl, butyl, t-butyl, pentyl, hexyl or heptyl;

each $R^2$, independently, is $CH_3$ or halogen;

linker is a moiety having the structure of

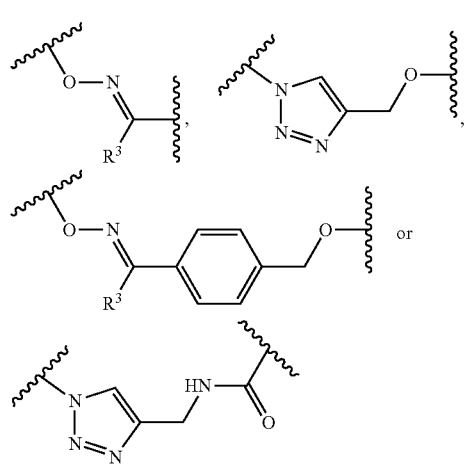

methyl, ethyl, propyl, isopropyl, butyl, t-butyl, pentyl, hexyl or heptyl;

each $R^2$, independently, is $CH_3$;

linker is a moiety having the structure of

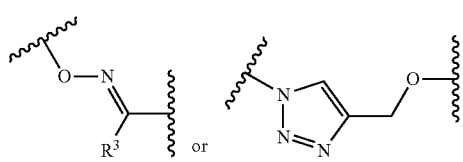

wherein $R^3$ is H; and

PEG is a polyethylene glycol polymeric moiety having a molecular weight of 3000, 5000 or 20,000.

In aspect 17 of the invention, the compositions include pegylated carfilzomib compounds of any one of aspects 1-16 wherein the compound is an individual compound as represented in examples 1-34 described hereinbelow in Table 2, or a pharmaceutically acceptable salt thereof.

In aspect 18 of the invention, the compositions include pegylated carfilzomib compounds of any one of aspects 1-17 wherein the compound is

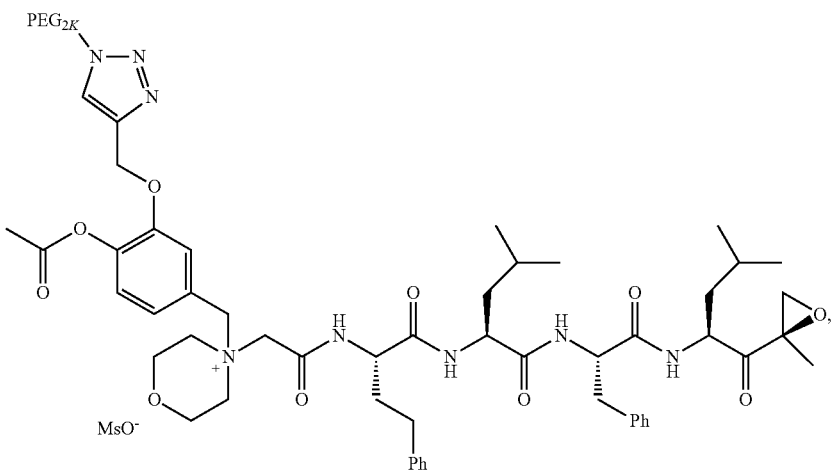
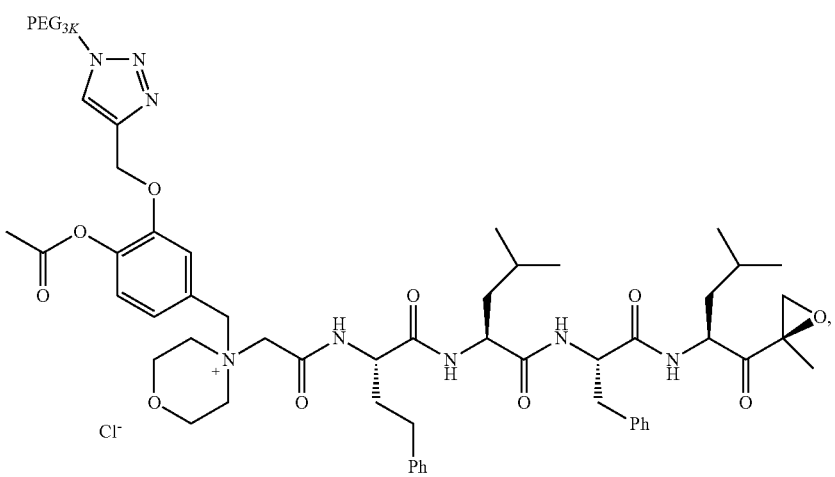
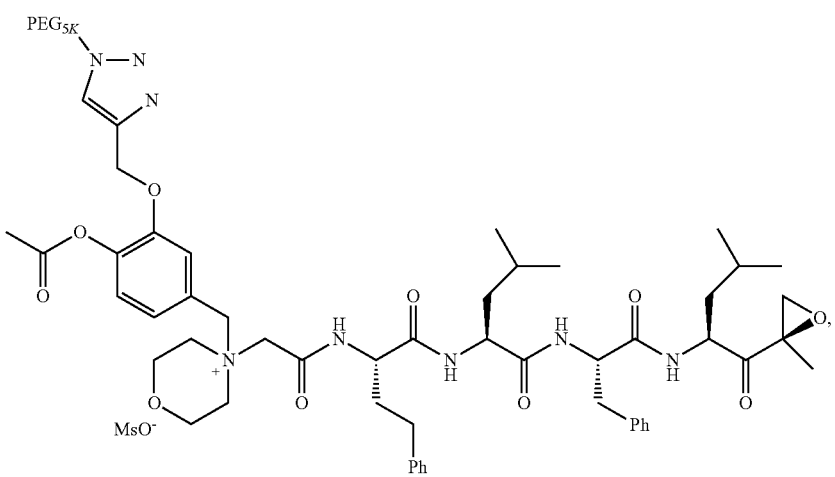

-continued
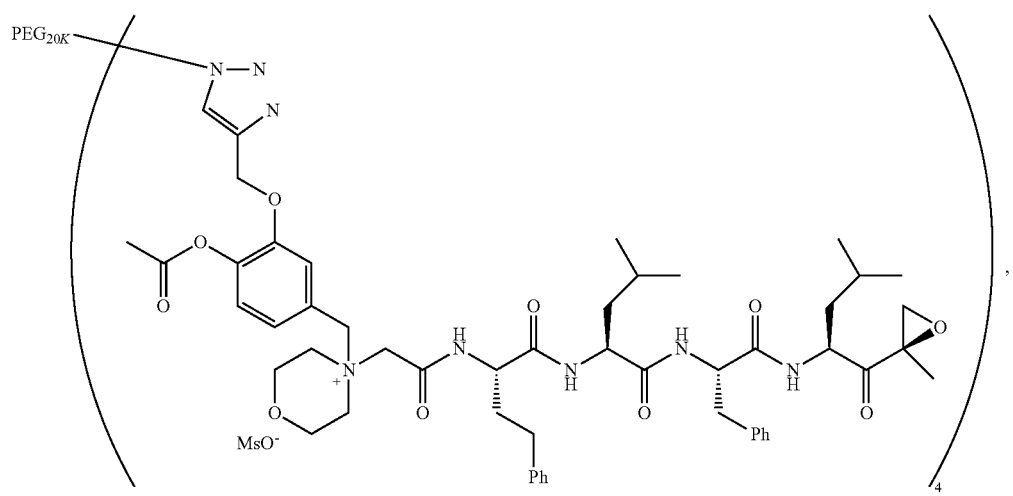
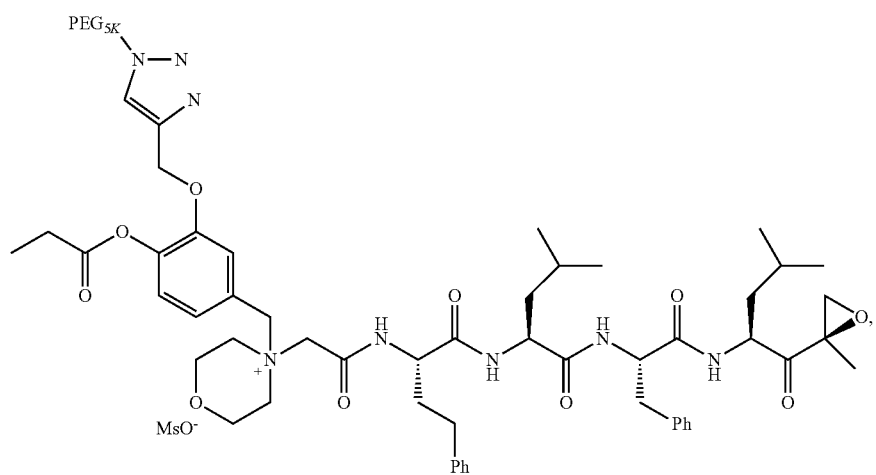
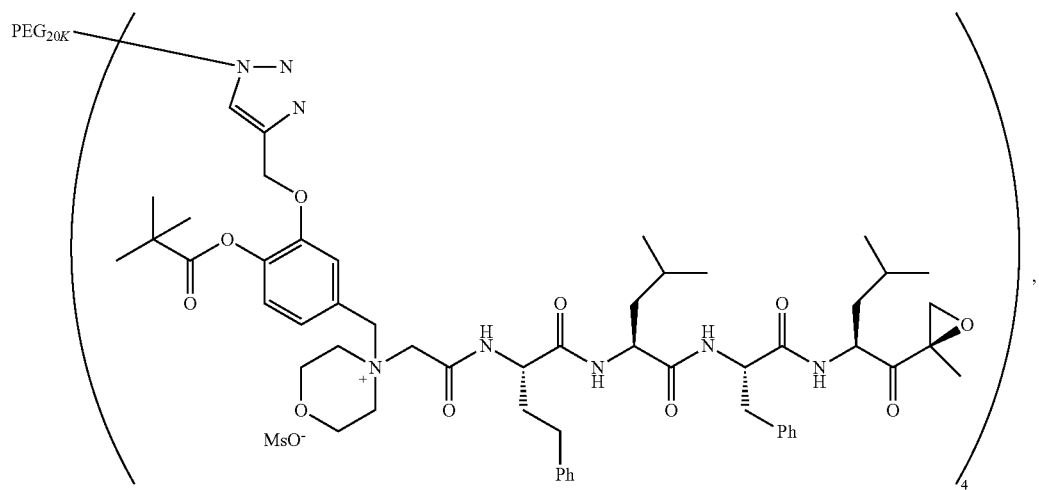

-continued
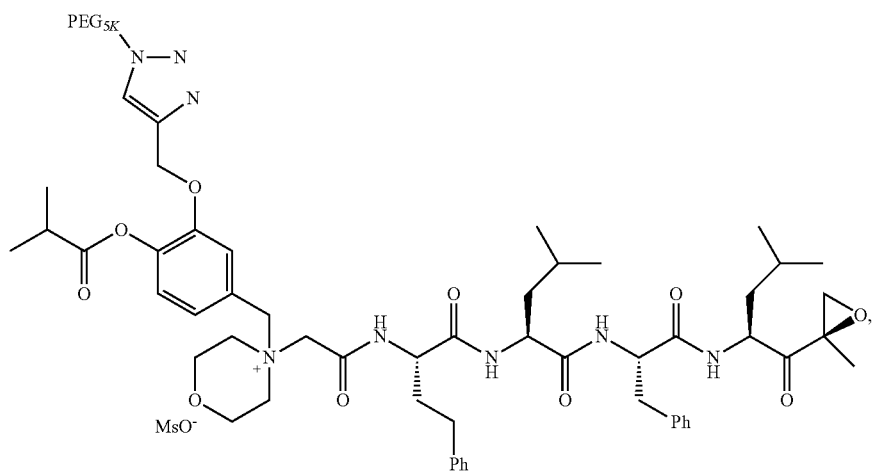
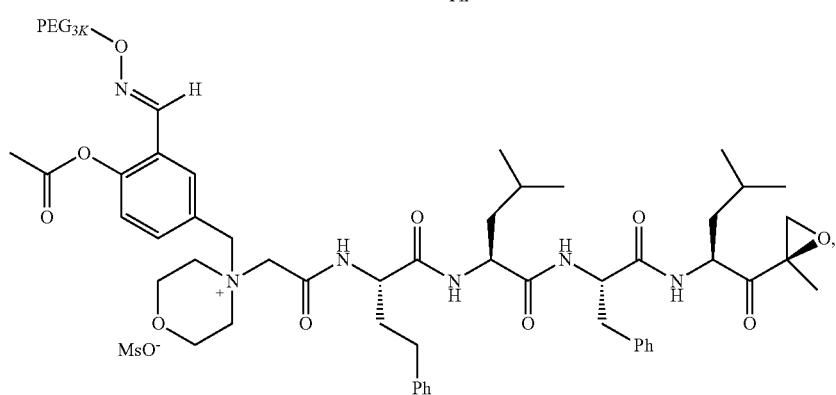
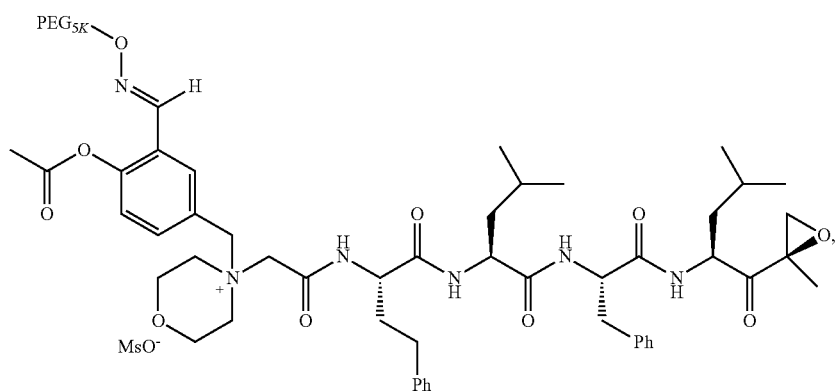
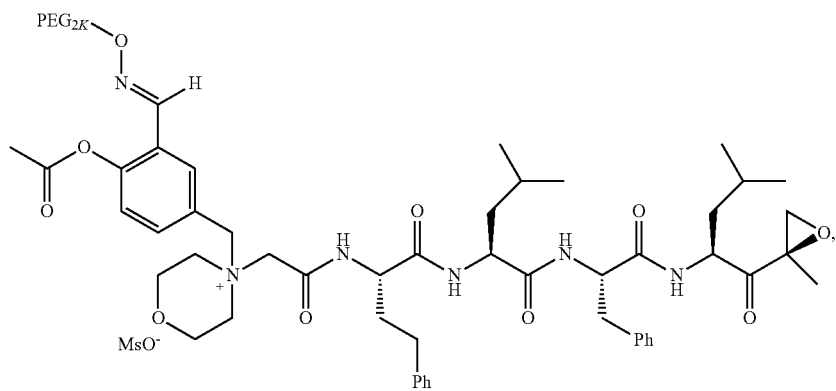

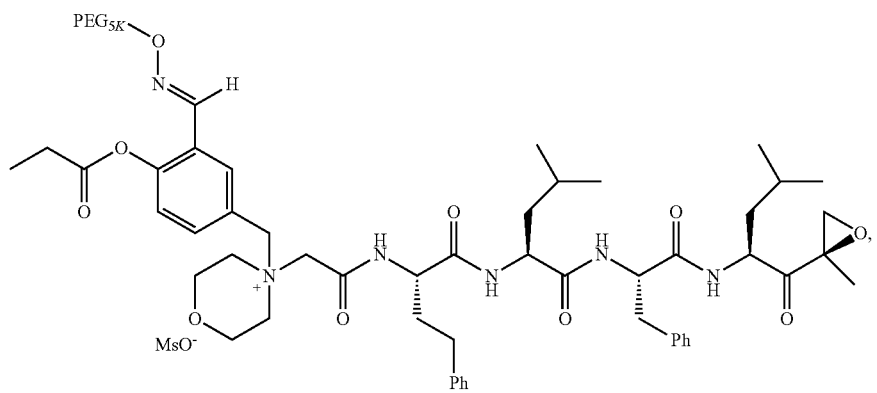
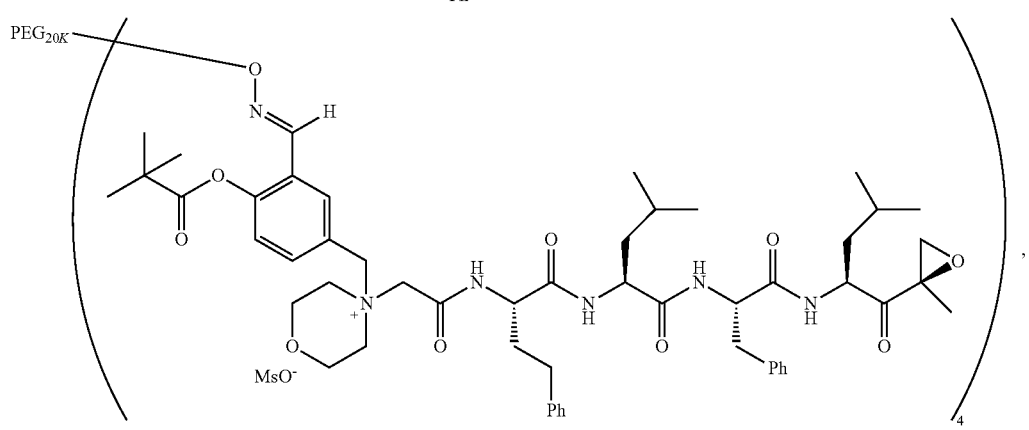
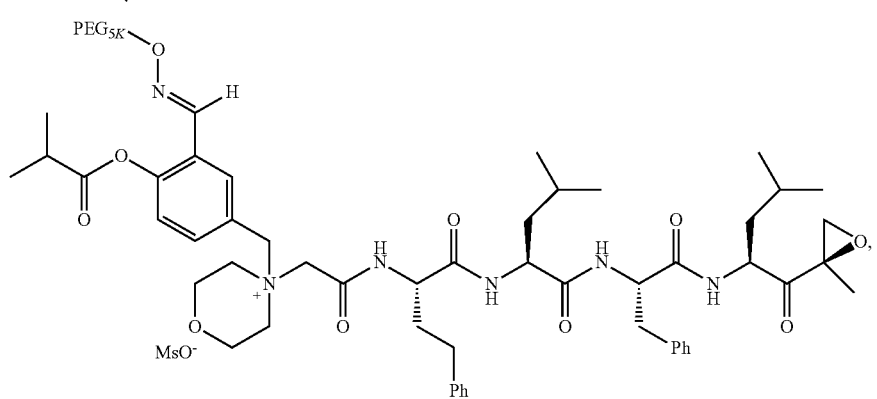
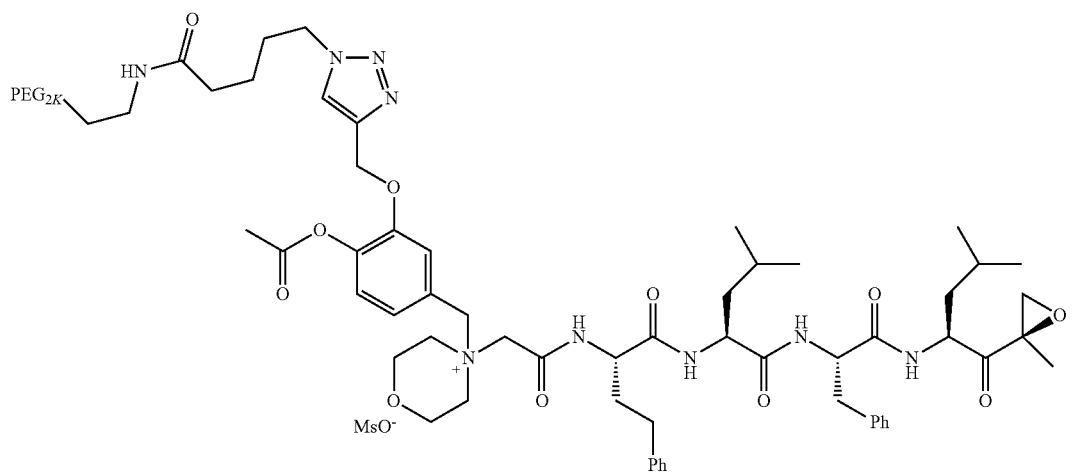
or

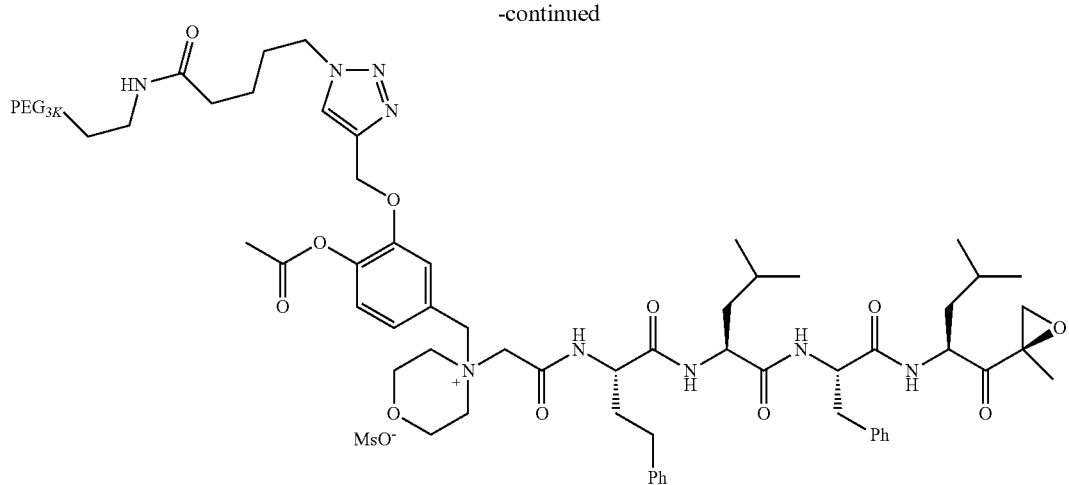
or a pharmaceutically acceptable salt thereof.
In aspect 18a of the invention, the compositions include pegylated carfilzomib compounds of any one of aspects 18 wherein the compound is
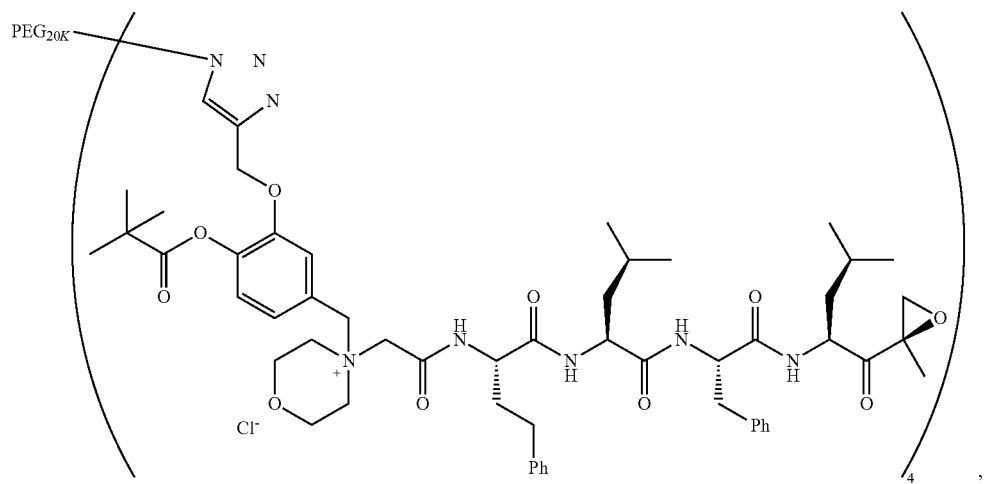
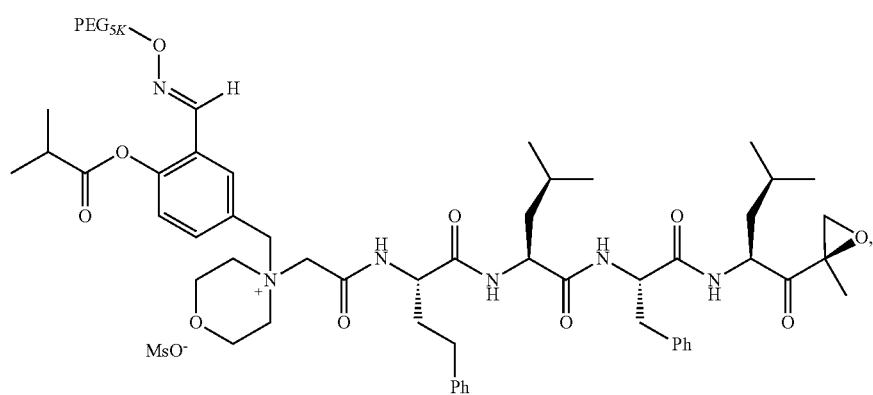

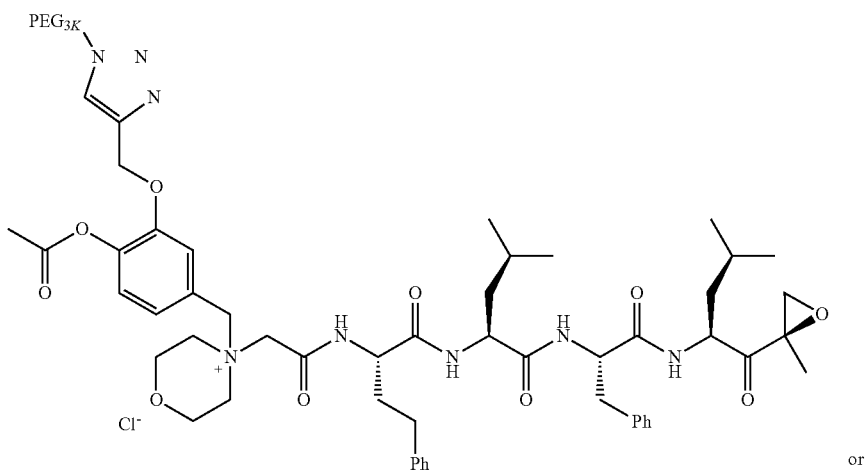
or
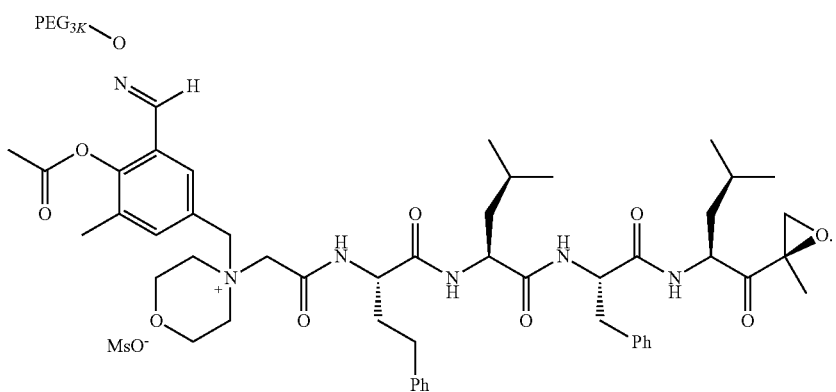
In aspect 19 of the invention, the compositions include pegylated carfilzomib compounds of any one of aspects 1-18 wherein the compound is
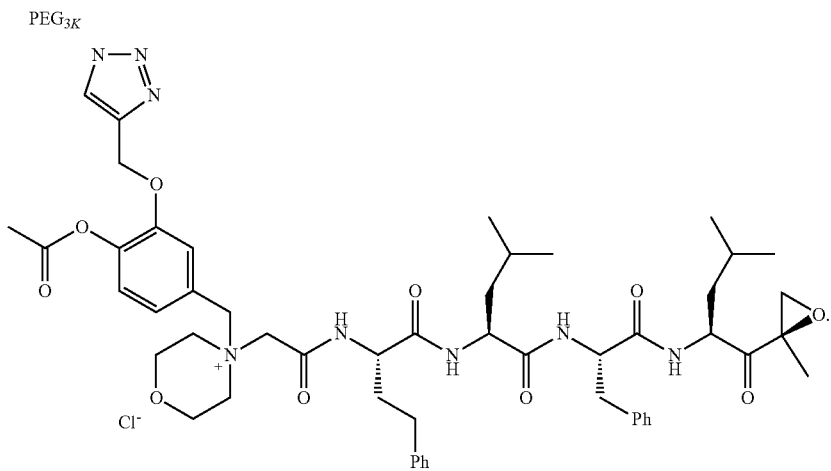

In aspect 19a of the invention, the compositions include pegylated carfilzomib compounds of an one of aspects 1-18 wherein the compound is
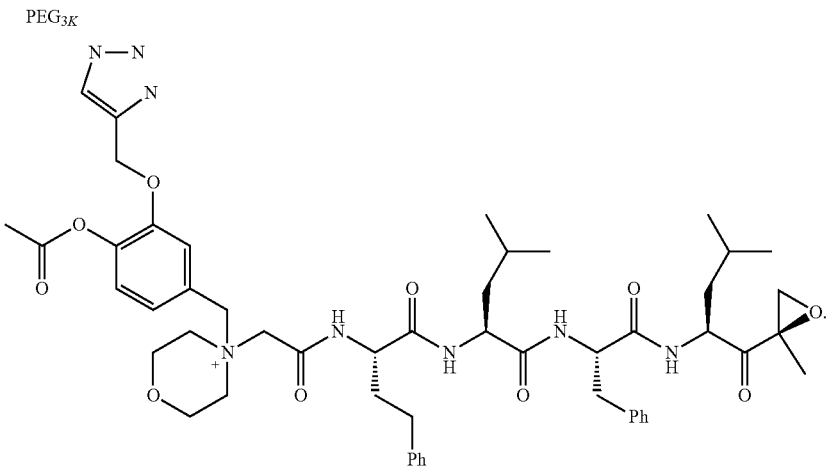
In aspect 20 of the invention, the compositions include pegylated carfilzomib compounds of any one of aspects 1-18 wherein the compound is
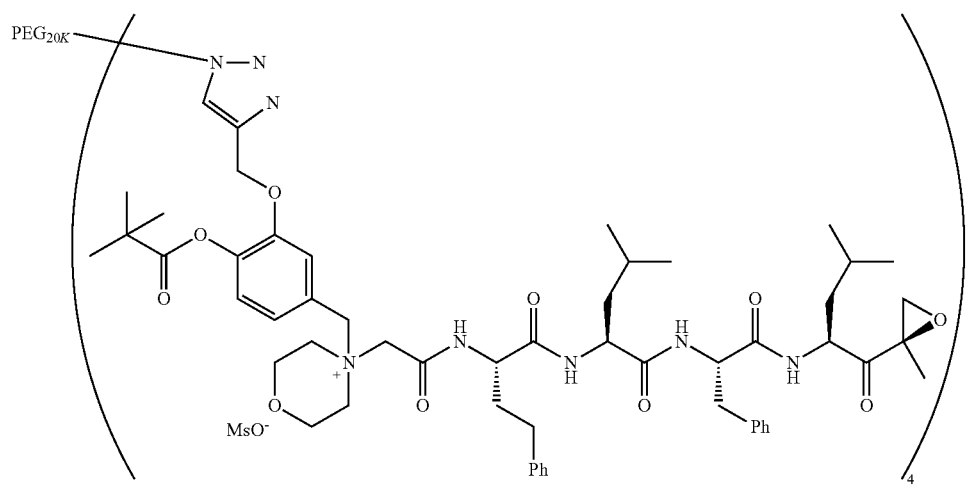

In aspect 21 of the invention, the compositions include pegylated carfilzomib compounds of any one of aspects 1-18 wherein the compound is
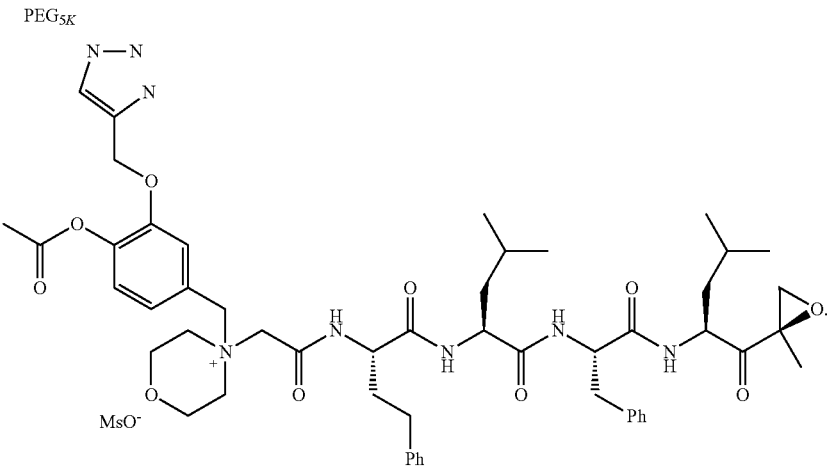
In aspect 22 of the invention, the compositions include pegylated carfilzomib compounds of any one of aspects 1-18 wherein the compound is
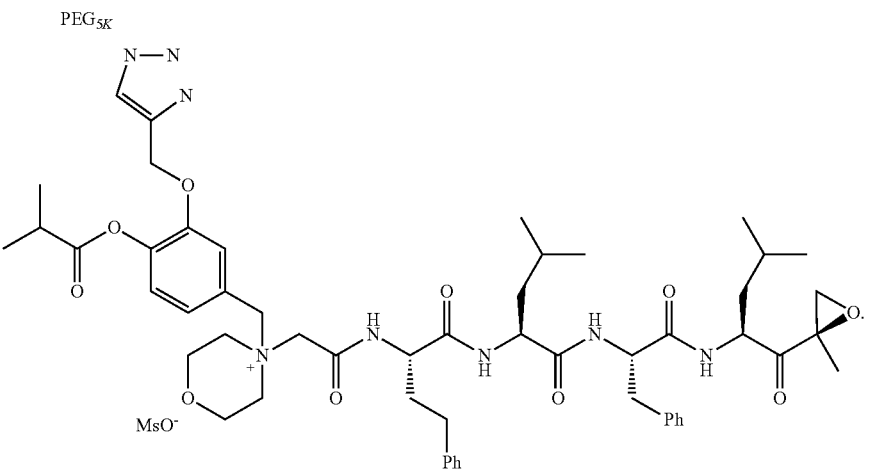

In aspect 23 of the invention, the compositions include pegylated carfilzomib compounds of any one of aspects 1-18 wherein the compound is

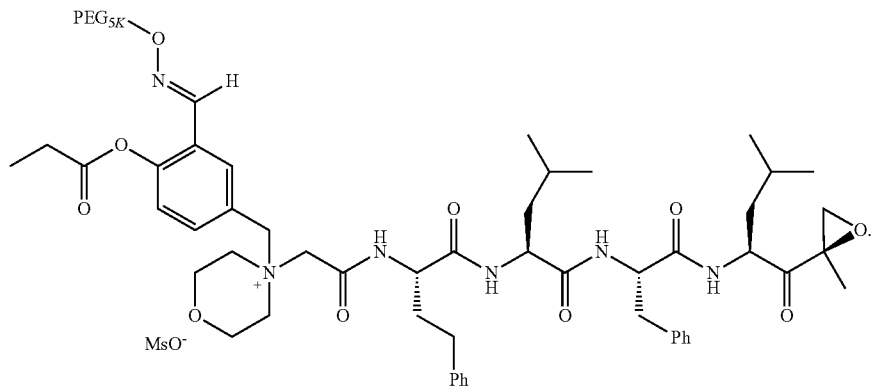

In aspect 24 of the invention, the compositions include pegylated carfilzomib compounds of any one of aspects 1-18 wherein the compound is

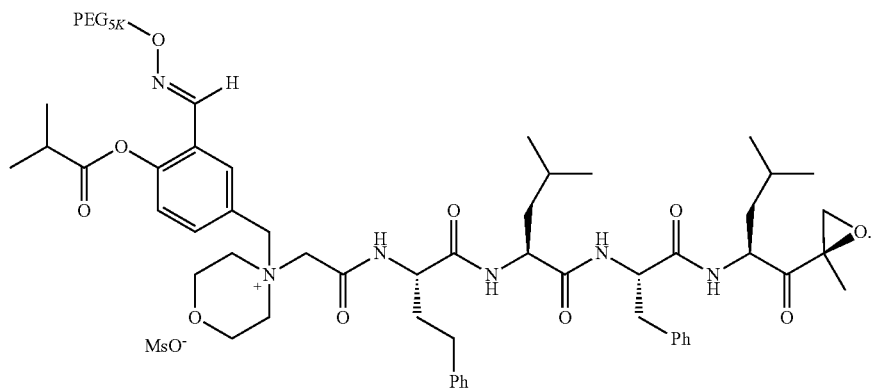

In aspect 25 of the invention, the compositions include pegylated carfilzomib compounds of any one of aspects 1-18 wherein the compound is

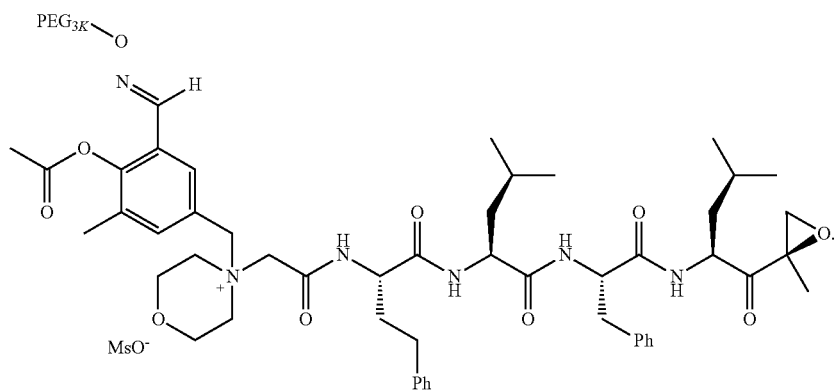

In aspect 26 of the invention, the compositions include pegylated carfilzomib compounds of any one of aspects 1-18 wherein the compound is

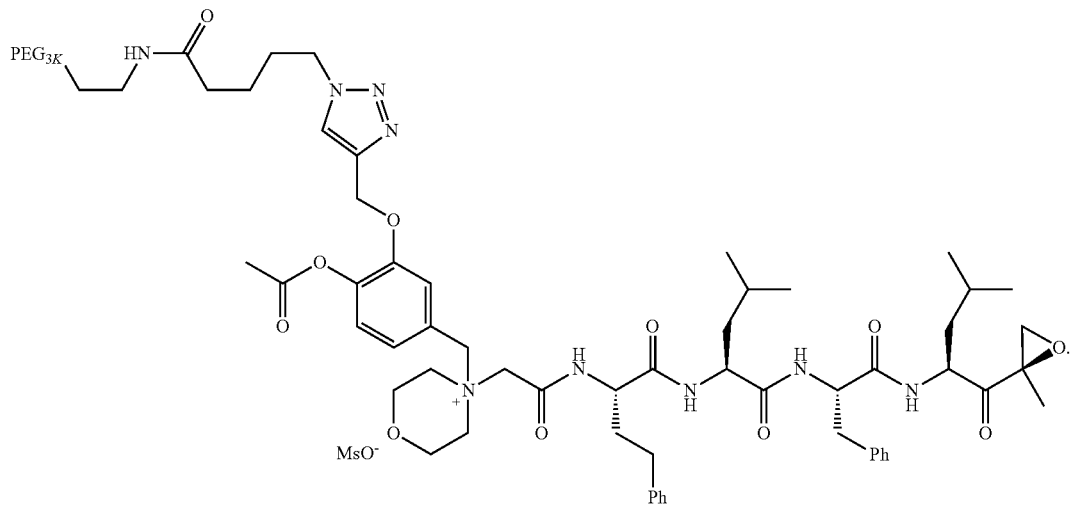

In aspect 27 of the invention the compositions include pegylated carfilzomib compounds of any one of aspects 1-16 wherein the PEG has a weight ranging from about 2K to about 20K.

In aspect 28 of the invention, the compositions include pegylated carfilzomib compounds of any one of aspects 1-16 wherein the PEG has a weight of 3K, 5K or 20K.

In aspect 29 of the invention, the compositions include pegylated carfilzomib compounds of any one of aspects 1-16 that is a pharmaceutically acceptable salt comprising a counter anion selected from a chloride anion, a bisulfate anion, a sulfate anion, a nitrate anion, a phosphate anion, an alky-sulfonate anion or an aryl-sulfonate anion.

In aspect 30 of the invention, the compositions include pegylated carfilzomib compounds of aspect 29 wherein the counter anion is a chloride anion or an alky-sulfonate anion.

In aspect 31 of the invention, the compositions include pegylated carfilzomib compounds of aspect 29 wherein the counter anion is a chloride anion or methane-sulfonate anion.

In aspect 32 of the invention, the compositions include pegylated carfilzomib compounds of any one of aspects 1-26 and a pharmaceutically acceptable excipient, carrier or diluent.

In aspect 33 of the invention, the invention provides a pharmaceutical composition comprising
    (a) a pegylated carfilzomib compound;
    (b) at least one excipient selected from the group consisting of sucrose, sorbital, glycerin, maltose, lactose, erythrose, dextrose, lactobiose, cyclodextrin, proline, glycine, arginine, histidine, aspartic acid, valine, leucine, alanine, methionine, proline, glutamic acid, glutamate, and a salt selected from the group consisting of sodium chloride, potassium chloride, ammonium sulfate, potassium chlorate, calcium chloride, zinc chloride, guanidine hydrochloride, ammonium chloride, potassium sulfate, ammonium aspartate, arginine-HCl, lysine-HCl, magnesium chloride and barium sulfate;
    (c) a buffering agent selected from the group consisting of glutamate, histidine, acetate, and Tris-HCl, or a combination thereof; and
    (d) optionally a bulking agent selected from the group consisting of mannitol, trehalose, PVP, cyclodextrin, glycine, dextrose, dextran, sucrose, proline, PEG 33350 and PEG 400,
    (e) optionally an amino acid selected from the group consisting of lysine, arginine, histidine, aspartic acid, valine, leucine, alanine, methionine, proline, glutamic acid and glutamate,
    (f) optionally a surfactant selected from the group consisting of polysorbate 20, polysorbate 80, pluronic F68, docusate sodium, benzaconium chloride, triton X100, tetrafunctional block O polymers, alcohols, SDS, protamine sulfate and butane,
    or a combination of (d), (e) and (f).

In aspect 33a of the invention, the invention provides a pharmaceutical composition comprising
    (a) a pegylated carfilzomib compound;
    (b) at least one excipient selected from the group consisting of sucrose, proline, glycine, and sodium chloride;
    (c) a buffering agent selected from the group consisting of glutamate, histidine, acetate, and Tris-HCl, or a combination thereof; and
    (d) optionally a bulking agent selected from the group consisting of mannitol, trehalose, PVP, cyclodextrin, glycine, dextrose, dextran, sucrose, proline, PEG 33350 and PEG 400,
    (e) optionally an amino acid selected from the group consisting of lysine, arginine, histidine, aspartic acid, valine, leucine, alanine, methionine, proline, glutamic acid and glutamate,
    (f) optionally a surfactant selected from the group consisting of polysorbate 20, polysorbate 80, pluronic F68, docusate sodium, benzaconium chloride, triton X100, tetrafunctional block O polymers, alcohols, SDS, protamine sulfate and butane,
    or a combination of (d), (e) and (f).

In aspect 33b, the invention provides the compositions of aspects 33 and 33a wherein the (b) at least one excipient is present in an amount ranging from 0.1-30% weight/volume; the (c) buffering agent is present in an amount sufficient to achieve the desired pH of the formulation; the (d) optional bulking agent is present in an amount ranging from 2-50% weight/volume; the (e) optional amino acid is present in an amount ranging from 0.1-10% by weight/volume; and the (f) surfactant is present in an amount ranging from 0.005-3% weight/volume of the composition.

In aspect 33c, the invention provides a pharmaceutical composition comprising
(a) a pegylated carfilzomib compound;
(b) at least one excipient selected from the group consisting of sucrose, proline, glycine, and sodium chloride;
(c) a buffering agent selected from the group consisting of glutamate, histidine, acetate, and Tris-HCl, or a combination thereof; and
(d) optionally a bulking agent selected from the group consisting of mannitol, trehalose, polyvinylpyrrolidone, and dextrose, the bulking agent present in an amount ranging from 2-50% by weight,
(e) optionally an amino acid selected from the group consisting of lysine, arginine, histidine, and proline, the amino acid present in an amount ranging from 0.1-10% by weight,
(f) optionally a surfactant selected from the group consisting of polysorbate 80, pluronic F68, polysorbate 20 and triton X100, the surfactant present in an amount ranging from 0.005-3% by weight, or a combination of (d), (e) and (f).

In aspect 33d, the invention provides a pharmaceutical composition comprising
(a) a pegylated carfilzomib compound;
(b) at least one excipient selected from the group consisting of sucrose in an amount ranging from 0.1-30% by weight, proline or glycine in an amount ranging from 0.1-10% by weight, and sodium chloride in an amount of about 300 nM concentration;
(c) a buffering agent selected from the group consisting of glutamate, histidine, acetate, and Tris-HCl, or a combination thereof; and
(d) optionally mannitol in an amount ranging from 2-50% by weight,
(e) optionally lysine or arginine, in an amount ranging from 0.1-10% by weight,
(f) optionally polysorbate 80 or pluronic F68 in an amount ranging from 0.005-3% by weight,
or a combination of (d), (e) and (f).

In aspect 34 of the invention, the invention provides the pharmaceutical composition of aspects 33 and 33a-33d, wherein the pegylated carfilzomib compounds have the structure of formula I as described herein in aspect 1 and 1a, as described herein in aspect 7, as described herein in aspect 18, or as described herein in aspect 18a.

In aspect 35 of the invention, the invention provides the pharmaceutical composition of any one of aspects 1-33, 33a-33d and 34, wherein the composition is a frozen formulation, wherein the pH of the formulation is in the range from 5.0 to 8.0.

In aspect 36 of the invention, the invention provides the pharmaceutical composition of aspect 35, wherein the excipient is selected from the group consisting of sucrose, proline, glycine, and sodium chloride or a combination thereof, and the buffering agent is selected from the group consisting of histidine, acetate and Tris-HCl or a combination thereof.

In aspect 37 of the invention, the invention provides the pharmaceutical composition of aspect 36, wherein the excipient is selected from the group consisting of sucrose in an amount in the range from about 5-12% weight/volume, proline in an amount in the range from about 50 to 300 mM concentration, glycine in an amount in the range from about 50 to 300 mM concentration, and sodium chloride in an amount in the range from about 30 to 160 mM concentration, or a combination thereof, and the buffering agent is selected from the group consisting of histidine in an amount in the range from about 10 to 30 mM concentration, acetate in an amount in the range from about 10 to 30 mM concentration, and Tris-HCl in an amount in the range from about 10 to 30 mM concentration, or a combination thereof.

In aspect 38 of the invention, the invention provides the pharmaceutical composition of any one of aspects 36 and 37, wherein the excipient is selected from the group consisting of sucrose in an amount of about 9% w/v, L-proline in an amount of about 220 mM concentration, glycine in an amount of about 293 mM concentration, sodium chloride in an amount of about 140 mM concentration, and a combination of sucrose in an amount of about 4.5% and sodium chloride in an amount of about 140 mM concentration; and the buffering agent is selected from the group consisting of histidine in an amount of about 10 mM concentration, acetate in an amount of about 10 mM concentration, and Tris-HCl in an amount of about 10 mM concentration.

In aspect 39 of the invention, the invention provides the pharmaceutical composition of any one of aspect 35-38, wherein the pharmaceutical composition comprises
(a) the pegylated carfilzomib compound in an amount ranging from 150 mg to 2000 mg;
(b) the at least one excipient and buffering agent is (1) 9% sucrose and 10 mM acetate buffer at pH 5; (2) 9% sucrose and 10 mM histidine at pH 6; (3) 9% sucrose and 10 mM Tris-HCl at pH 7; (4) 9% sucrose and 10 mM Tris-HCl at pH 8; (5) 140 mM sodium chloride and 10 mM Tris-HCl at pH 7; (6) 220 mM L-proline and 10 mM Tris-HCl at pH 7; (7) 293 mM glycine and 10 mM Tris-HCl at pH 7; or (8) 70 mM sodium chloride and 4.5% sucrose with 10 mM Tris-HCl at pH 7.

In aspect 40 of the invention, the invention provides the pharmaceutical composition of any one of aspects 1-33, 33a-33d and 34, wherein the composition is a dry lyophilized formulation.

In aspect 41 of the invention, the invention provides the pharmaceutical composition of claim 40, wherein the at least one excipient is sucrose in an amount ranging from 0.5% to 2% weight/weight, the bulking agent is mannitol in an amount ranging from 2 to 4% weight/weight, the amino acid is either absent or selected from lysine or arginine, and the surfactant is either absent or is polysorbate 80 or pluronic F68, and the buffering agent is glutamate.

In aspect 42 of the invention, the invention provides the pharmaceutical composition of claim 41, wherein the excipient is sucrose in an amount in the range from about 1-2% weight/volume, mannitol in an amount in the range from about 2 to 4%, an amino acid selected from lysine or arginine in an amount ranging from about 0.5% to 0.8%, the surfactant that is either 0.0065 polysorbate 80 or 0.05% pluronic F68, and the buffer is 10 mM glutamate.

In aspect 43 of the invention, the invention provides the pharmaceutical composition of any one of aspects 1-33, 33a-33d, 34, 41 and 42, wherein the composition consists essentially of
  10 mm glutamate, 2% sucrose, and 4% mannitol, or
  10 mM glutamate, 2% sucrose, 4% mannitol, and 0.006% polysorbate 80, or
  10 mM glutamate, 2% sucrose, 4% mannitol, and 0.05% pluronic F68, or 10 mM glutamate, 2% sucrose, 4% mannitol, 0.5% lysine and 0.006% polysorbate 80, or 10 mM glutamate, 2% sucrose, 4% mannitol, 0.8% lysine and 0.006% polysorbate 80, or 10 mM glutamate, 2% sucrose, 4% mannitol, 0.5% arginine and 0.006% polysorbate 80, or 10 mM glutamate, 2% sucrose, 4% mannitol, 0.8% arginine and 0.006% polysorbate 80; and a pegylated carfilzomib compound in an amount ranging from 100 mg to 3000 mg.

In aspect 44 of the invention, the invention provides the pharmaceutical composition of aspect 43 where in when the composition is dissolved in water sufficient to achieve a concentration of about 10 mg/ml of the pegylated carfilzomib compound, the pH of the composition was about 5.0.

In aspect 45 of the invention, the invention provides the pharmaceutical composition of any one of aspects 40-44, wherein the pharmaceutical composition comprises the pegylated carfilzomib compound in an amount ranging from 150 mg to 2000 mg.

In aspect 46 of the invention, the invention provides the pharmaceutical composition of any one of aspects 40-45, wherein the pharmaceutical composition comprises the pegylated carfilzomib compound in an amount ranging from 300 mg to 2000 mg.

In aspect 47 of the invention, the invention provides the pharmaceutical composition of any one of aspects 40-46, wherein the pharmaceutical composition comprises the pegylated carfilzomib compound in an amount ranging from 800 mg to 3000 mg.

In aspect 48 of the invention, the invention provides the pharmaceutical composition of any one of aspects 40-45, wherein the pegylated carfilzomib compound is a 2K, 3K or 5K pegylated carfilzomib compound in an amount ranging from 200 mg to 800 mg.

In aspect 49 of the invention, the invention provides the pharmaceutical composition of any one of aspects 1-48 wherein the composition further comprises hyaluronidase.

In aspect 50 of the invention, the invention provides the pharmaceutical composition of aspect 49 wherein the hyaluronidase is present in an amount ranging from 1500 to 2500 units/mL.

In aspect 50a of the invention, the invention provides the pharmaceutical composition of aspects 49 and 50 wherein the hyaluronidase is present in an amount of 2000 units/mL.

In aspect 51 of the invention, the invention provides the pharmaceutical composition of any one of aspects 1-50 and 50a that does not contain a cyclodextrin.

In aspect 52 of the invention, the invention provides the pharmaceutical composition of any one of aspects 40-51 wherein the lyophilized formulation when dissolved in 1.0 ml of water at room temperature provides a clear solution within a time period of about 3 minutes.

In aspect 53 of the invention, the invention provides the pharmaceutical composition of any one of aspects 1-1-33, 33a-33d and 34-50, 50a, 51 and 52 that is administered parenterally by infusion, injection, or subcutaneous route of administration.

In aspect 54 of the invention, the invention provides the pharmaceutical composition of any one of aspects 1-52 that is administered intravenously by infusion or injection.

In aspect 55 of the invention, the invention provides the pharmaceutical composition of any one of aspects 1-1-33, 33a-33d and 34-50, 50a, 51 and 52 that is administered by sub-cutaneous injection.

In aspect 56 of the invention, the invention provides a method of treating cancer comprising administering to a patient in need thereof, a therapeutically effective amount of the pharmaceutical composition of any one of aspects 1-1-33, 33a-33d and 34-50, 50a and 51-55.

In aspect 57 of the invention, the invention provides the method of aspect 56 wherein the cancer is multiple myeloma.

In aspect 58 of the invention, the invention provides the method of aspect 57 wherein the multiple myeloma is relapsed, refractory or relapsed and refractory multiple myeloma.

In aspect 59 of the invention, the invention provides the method of aspect 58 wherein the multiple myeloma is newly diagnosed multiple myeloma.

In aspect 60 of the invention, the invention provides a process of making the pharmaceutical composition of any one of aspects 1-1-33, 33a-33d and 34-50 and 50a, the process comprising the step of (a) combining a pegylated carfilzomib compound in an amount effective to treat multiple myeloma with at least one excipient selected from the group consisting of sucrose, proline, glycine, and sodium chloride; and a buffering agent selected from the group consisting of glutamate, histidine, acetate, and Tris-HCl, or a combination thereof; and (b) mixing the combination to provide a clear solution.

While not wishing to be bound by theory, it is possible that the pharmaceutical compositions of the present invention may mask or partially mask the protease inhibitory activity of the API temporarily. This effect may occur until the pegylated linked moieties of the pegylated carfilzomib compounds have cleaved thereby releasing free carfilzomib into the systemic circulation. This delay in activity may reduce or eliminate undesired side effects, which may otherwise be associated with various routes of administration. It is also noted that the pegylated carfilzomib compounds included in the compostions of the present invention may act as pro-drugs of carfilzomib. Alternatively, these compounds may very well possess active proteasome inhibitory activity in and of themselves.

The beneficial properties of the compositions of the present invention may also facilitate subcutaneous administration of the pegylated carfilzomib compounds. By virtue of sub-cutaneous administration, the invention potentially improves dosing as well as patient convenience and compliance in treatment with the selected pegylated carfilzomib compound.

In other aspects or embodiments of the invention, which maybe later described herein, methods are featured for treating a disease or condition selected from the group consisting of cancer, autoimmune disease, graft or transplant-related condition, neurodegenerative disease, fibrotic-associated condition, ischemic-related conditions, infection (viral, parasitic or prokaryotic) and diseases associated with bone loss, the method includes administering to a patient a pharmaceutical composition according to the present invention, the composition comprising a therapeutically effective amount of a pegylated carfilzomib compound, such as those described herein. In still further aspects, methods for treating cancer (e.g., multiple myeloma, e.g., multiple myeloma that is relapsed and/or refractory) in a patient are provided by the invention.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety, as if herein written. In case of conflict, the present specification, including definitions, will control. Other features and advantages of the disclosure will be apparent from the brief description of the figures, the figures themselves, the detailed description and from the claims.

As used herein, the term "aspect" is used synonymously and interchangeably with the term "embodiment."

Definitions

The following definitions should further assist in understanding the terms as used herein and the scope of the invention described herein.

The term "$C_{x-y}$alkyl" refers to substituted or unsubstituted saturated hydrocarbon groups, including straight-chain alkyl and branched-chain alkyl groups that contain from x to y carbons in the chain. The term "haloalkyl" refers to alkyl groups in which at least one hydrogen atom is replace by a halo (e.g., fluoro, chloro, bromo, iodo), e.g., $CH_2F$, $CHF_2$, trifluoromethyl and 2,2,2-trifluoroethyl.

The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond, respectively. In some embodiments, divalent groups alkenylene and alkynylene include from 2 to 12 carbon atoms. In certain embodiments, alkylene and alkynylene include from 2 to 10 carbon atoms. In certain embodiments, alkylene and alkynylene include from 2 to 6 carbon atoms (e.g., 2, 3, 4, 5, or 6 carbon atoms).

The term "alkoxyl" refers to an alkyl group having an oxygen attached thereto. Representative alkoxyl groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "$C_{3-y}$cycloalkyl", as used herein, refers to a fully saturated, substituted or unsubstituted, ring in which each atom of the ring is carbon, and the ring contains from 3 to y carbon atoms in size. For instance, the term $C_{3-7}$cycloalkyl is intended to mean a carbocyclic ring containing anywhere from 3 to 7 carbon atoms in size. Such rings include, for example, cyclopropyl, cyclobutyl, cyclopentyl, cyclohexyl and cycloheptyl rings. These rings may further be substituted as specified.

The terms "cancer" and "cancerous" when used herein refer to or describe the physiological condition in subjects that is typically characterized by unregulated cell growth. Examples of cancer include, without limitation, hematologic malignancies or blood borne cancers such as multiple myeloma and leukemia, and other cancers such as carcinoma, lymphoma, sarcoma, and blastoma. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers, in a subject, which have become resistant in some degree to treatment with anti-cancer agents, including without limitation chemotherapeutic agents, antimitotic agents, anthracyclines and the like, and for cancers which have relapsed post treatment with such anti-cancer agents.

The term "comprising" is meant to be open ended, including the indicated component(s) but not excluding other elements.

The term or abbreviation "eg" or "eg." as used herein is intended to mean "example."

The term "inhibitor" is meant to describe a compound that blocks or reduces an activity of an enzyme or system of enzymes, receptors, or other pharmacological target (for example, inhibition of proteolytic cleavage of standard fluorogenic peptide substrates such as suc-LLVY-AMC, Box-LLR-AMC and Z-LLE-AMC, inhibition of various catalytic activities of the 20S proteasome). An inhibitor can act with competitive, uncompetitive, or noncompetitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme. The term inhibitor is used more broadly herein than scientific literature so as to also encompass other classes of pharmacologically or therapeutically useful agents, such as agonists, antagonists, stimulants, co-factors, and the like.

The terms "drug resistant" and "multidrug resistant" when used herein refers to cancer cells that have developed and/or are resistant to drug. These include cancer cells exhibiting little to no efficacy or decreased efficacy from that exhibited at the initial dose of the drug. The cancer cells may be resistant to one drug or to multiple drugs of different chemical structures that are directed to act at different biological targets within the cancer cell.

The term "pharmaceutically-acceptable salt" embraces salts commonly used to form alkali metal salts and to form addition salts of free acids or free bases. The nature of the salt is not critical, provided that it is pharmaceutically-acceptable. Suitable pharmaceutically-acceptable acid addition salts of the compound may be prepared from an inorganic acid or from an organic acid. Examples of such inorganic acids include, without limitation, hydrochloric, hydrobromic, hydroiodic, nitric, carbonic, sulfuric and phosphoric acid. Examples of organic acids include, without limitation, aliphatic, cycloaliphatic, aromatic, arylaliphatic, heterocyclic, carboxylic and sulfonic classes of organic acids, examples of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid.

Suitable pharmaceutically-acceptable base addition salts of the compound include, without limitation, metallic salts such as salts made from aluminum, calcium, lithium, magnesium, potassium, sodium and zinc, or salts made from organic bases including primary, secondary, tertiary amines and substituted amines including cyclic amines such as caffeine, arginine, diethylamine, N-ethyl piperidine, histidine, glucamine, isopropylamine, lysine, morpholine, N-ethyl morpholine, piperazine, piperidine, triethylamine, trimethylamine. All of the salts contemplated herein may be prepared by conventional means from the corresponding compound by reacting, for example, the appropriate acid or base with the compound.

The term "proteasome" as used herein is meant to include immuno- and constitutive proteasomes.

The term "refractory" when used here is intended to refer to not-yielding to, resistant or non-responsive to treatment, stimuli (therapy) or cure, including resistance to multiple therapeutic curative agents. "Refractory" when used herein in the context of characterizing a cancer or tumor is intended to refer to the cancer or tumor being non-responsive or having a resistant or diminished response to treatment with one or more anticancer agents. The treatment typically is continual, prolonged and/or repetitive over a period of time resulting in the cancer or tumor relapsing or developing resistance or becoming refractory to that very same treatment.

The term "subject" as used herein refers to any mammal, including humans, and animals such as cows, horses, dogs and cats. Thus, the invention may be used in human patients as well as in veterinarian subjects and patients. In one embodiment of the invention, the compounds of the invention may be administered to a human subject.

The phrase "therapeutically-effective" or "therapeutically effective amount" is intended to quantify the amount of the compound of the invention, which when administered as part of a desired dosage regimen (to a patient, e.g., a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment. Thus, it is the amount of the compound of the invention that can treat cancer, whether it is multiple myeloma or other hematologic malignancy or a solid tumor.

The terms "treat", "treating" and "treatment" as used herein refer to therapy, including without limitation, curative therapy, prophylactic therapy, and preventative therapy and generally include reversing, reducing, or arresting the symptoms, clinical signs, and underlying pathology of a condition in manner to improve or stabilize a patient's condition. Prophylactic treatment generally constitutes either preventing the onset of disorders altogether or delaying the onset of a pre-clinically evident stage of disorders in individuals. The term "prophylactic or therapeutic" treatment is art-recognized and includes administration to the host of one or more of the subject compositions. If it is administered prior to clinical manifestation of the unwanted condition (e.g., disease or other unwanted state of the host animal), or after the condition has subsided, then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term PEG, as used herein, is intended to have its commonly understood and traditional meaning. Particularly, PEG is a moiety made up of repeating poly(ethylene glycol) polymeric units, the precise number of which determines its molecule weight. The unit of this molecular weight is daltons. Thus, it is intended that reference to a molecular weight of PEG as used herein (the specification, claims and abstract), for example, reference of "2K", "3K", "5K" and "20K" or "2000", "3000", "5000" or "20000" with respect to a given PEG means a 2000 dalton (or 2 kilodalton), 3000 dalton (or 3 kilodalton), 5000 dalton (or 5 kilodalton), and 20000 dalton (or 20 kilodalton), respectively, PEG weight. Further, as used herein "KDa" means kilodalton.

General Synthesis and Representative Examples of the Pegylated Carfilzomib Compounds Used in the Present Invention As described, the pegylated carfilzomib compounds in formulas I and II are cleavable polymer PEG carriers of the active pharmaceutical ingredient, carfilzomib (Formulas I and II) and release free carfilzomib in vivo. The following abbreviations used throughout both the general schemes and the examples, are intended to mean the following:

| | |
|---|---|
| DCM | dichloromethane; methylene dichloride |
| DMF | dimethylformamide |
| DMSO | dimethyl sulfoxide |
| EtOAc | ethyl acetate |
| MeOH | methanol |
| mpk | milligram per kilogram; mg/kg |
| RT, rt | room temperature |
| NaCl | sodium chloride |
| tBuOH | t-butanol; t-butyl alcohol |

Carfilzomib, used to prepare the pegylated carfilzomib compounds, is described in PCT publications WO2006017842, WO2009045497, WO2014169897, WO2013169282, WO2014011695, WO2006063154, WO2014015016, WO2010048298 and U.S. Pat. Nos. 7,714,042 and 7,737,112.

Scheme 1: Cleavage of benzyl elimination quaternary salt

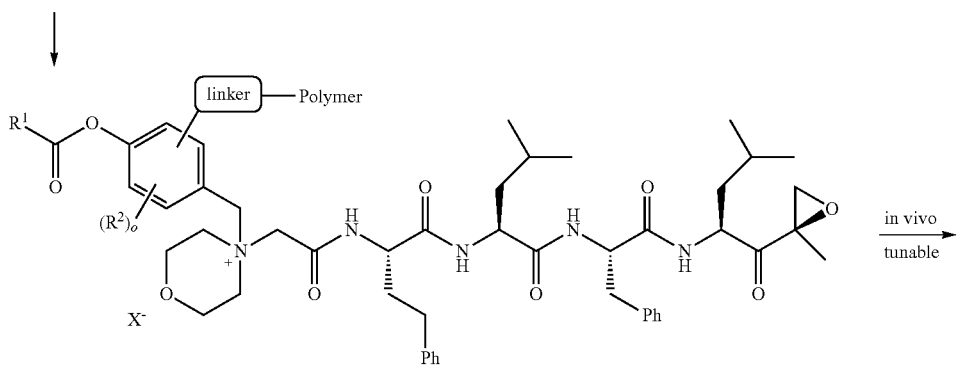

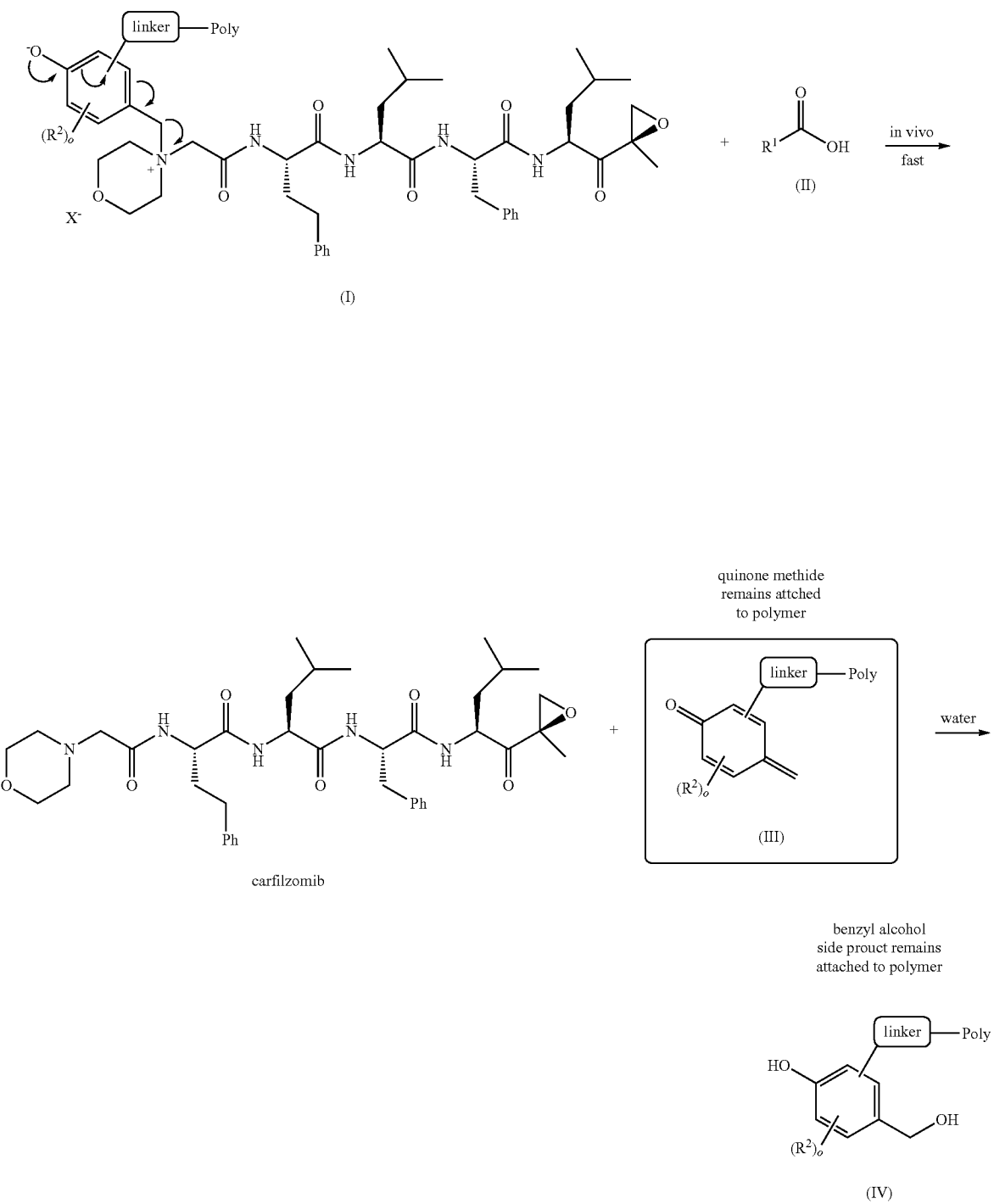

Enzymatic and/or chemical hydrolysis of the phenyl ester provides a carboxylic acid (II) and a phenolate intermediate (I) which undergoes rapid 1, 6 elimination to provide free carfilzomib and a quinone methide which remains covalently attached to the solubilizing PEG polymer. Quinone methides are known to be reactive Michael acceptors and are believed to present risks related to potential genotoxicity. In this invention, permanent attachment of the quinone methide linker byproduct to the polymer may attenuate toxicity by preventing cellular access and lowering reactivity to serum nucleophiles. The most likely fate of intermediate III in vivo is reaction with water to form a benzyl alcohol-polymer adduct that is quickly removed from the body by excretion.

Scheme 2: Cleavage of previously described carfilzomib-polymer conjugates

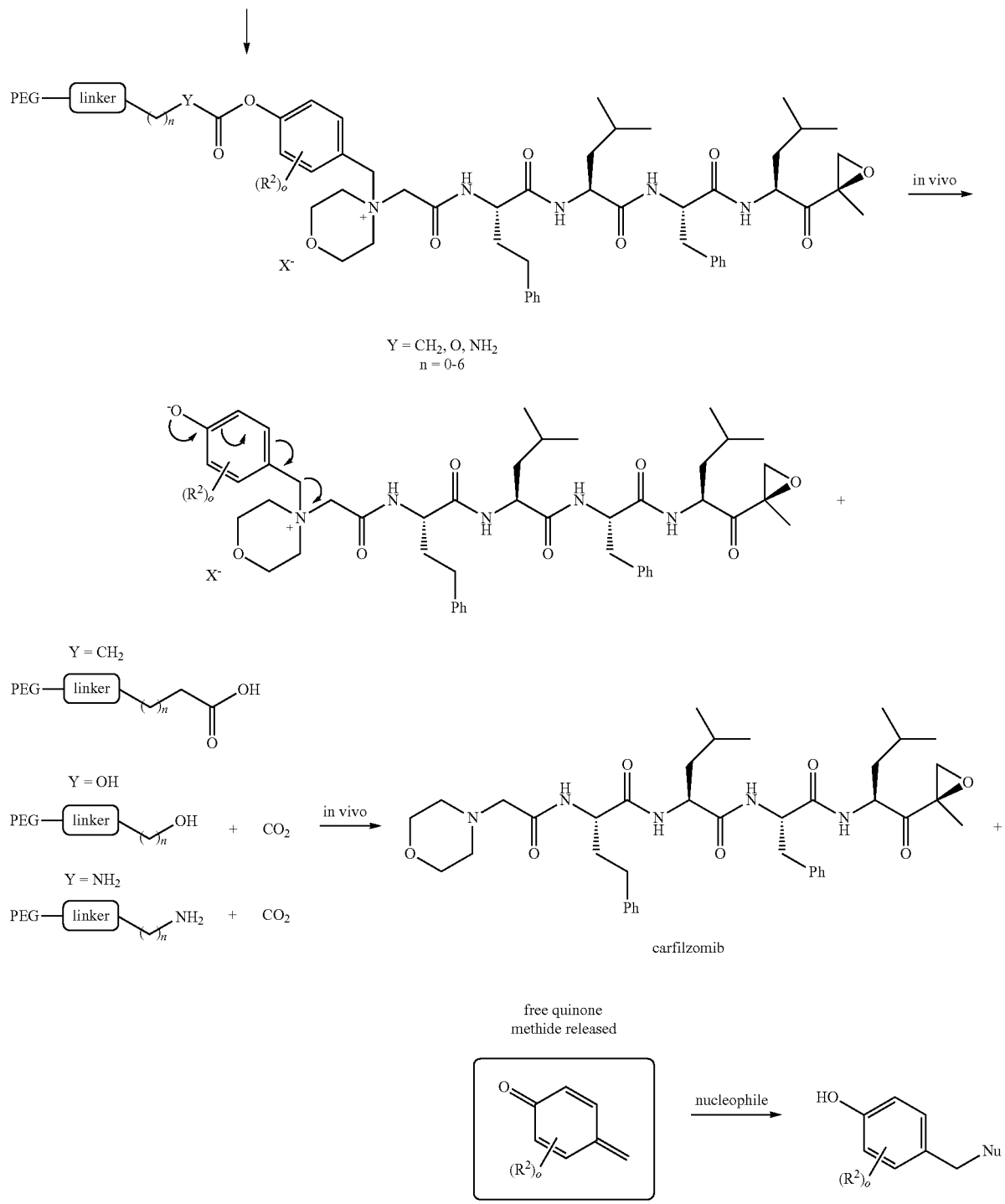

Scheme 2 illustrates one metabolic pathway for the carfilzomib polymer compounds described in WO2014011695. Here, as illustrated above, the carfilzomib-polymer conjugates interact with an esterase enzyme or are subject to chemical attack as shown by the arrow. This attack results in the release of a free quinone methide (encapsulated above) upon ester hydrolysis. This methide intermediate is free to react further with cellular nucleophiles, which may possibly result in toxicity. The pegylated carfilzomib compounds of the present invention avoid this potentially toxic byproduct, as described in scheme 1.

Scheme 3: Two-step PEG polymer conjugation procedure
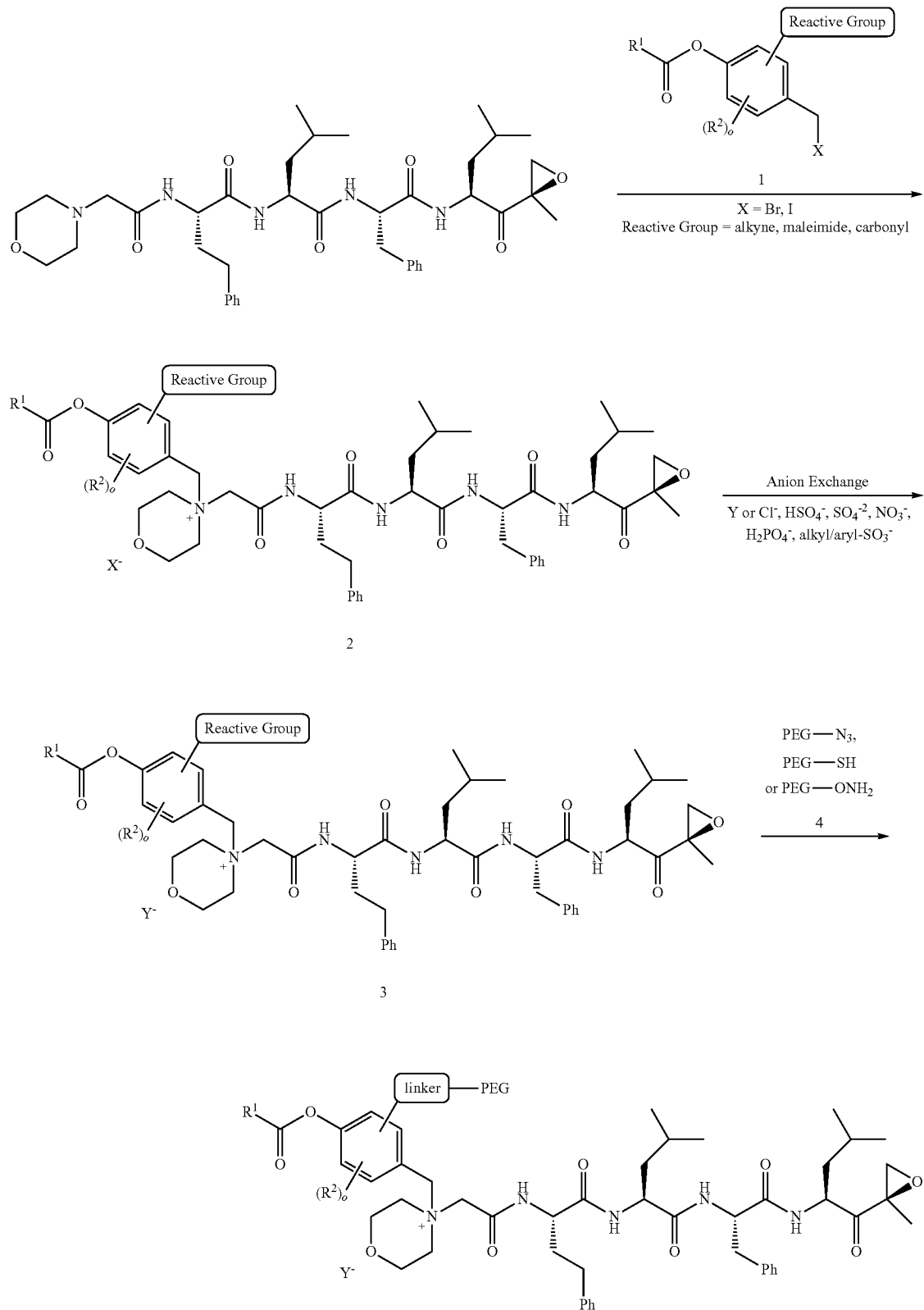

The carfilzomib-PEG compounds provided by the present invention are prepared in a two-step procedure, as shown in Scheme 3. Carfilzomib is first reacted with an appropriately substituted para-alkanoyloxy substituted benzyl halide (1) to give a quaternary salt intermediate (2). The quaternary salt bromide or iodide anion may be exchanged to a pharmaceutically acceptable anion such as bisulfate, sulfate, nitrate, dihydrogen phosphate or alkyl/aryl sulfonate via ion exchange resin to give intermediate (3). This intermediate is conveniently appended with a reactive group suitable for reaction with a complimentarily functionalized polymer reagent (4) to afford desired product 5. A large number of PEG reagents are commercially available in a range of molecular weights, architectures, end group chemistries, and number of reactive end groups (arms) (see Table 1). They may be directly compatible with the linker chemistries described in this disclosure or may require some further chemical manipulation by known methods. Branched chain and multi-arm PEGs may offer advantages over linear PEGs such as the potential for higher drug loading, improved stability, and/or lower formulation viscosities.

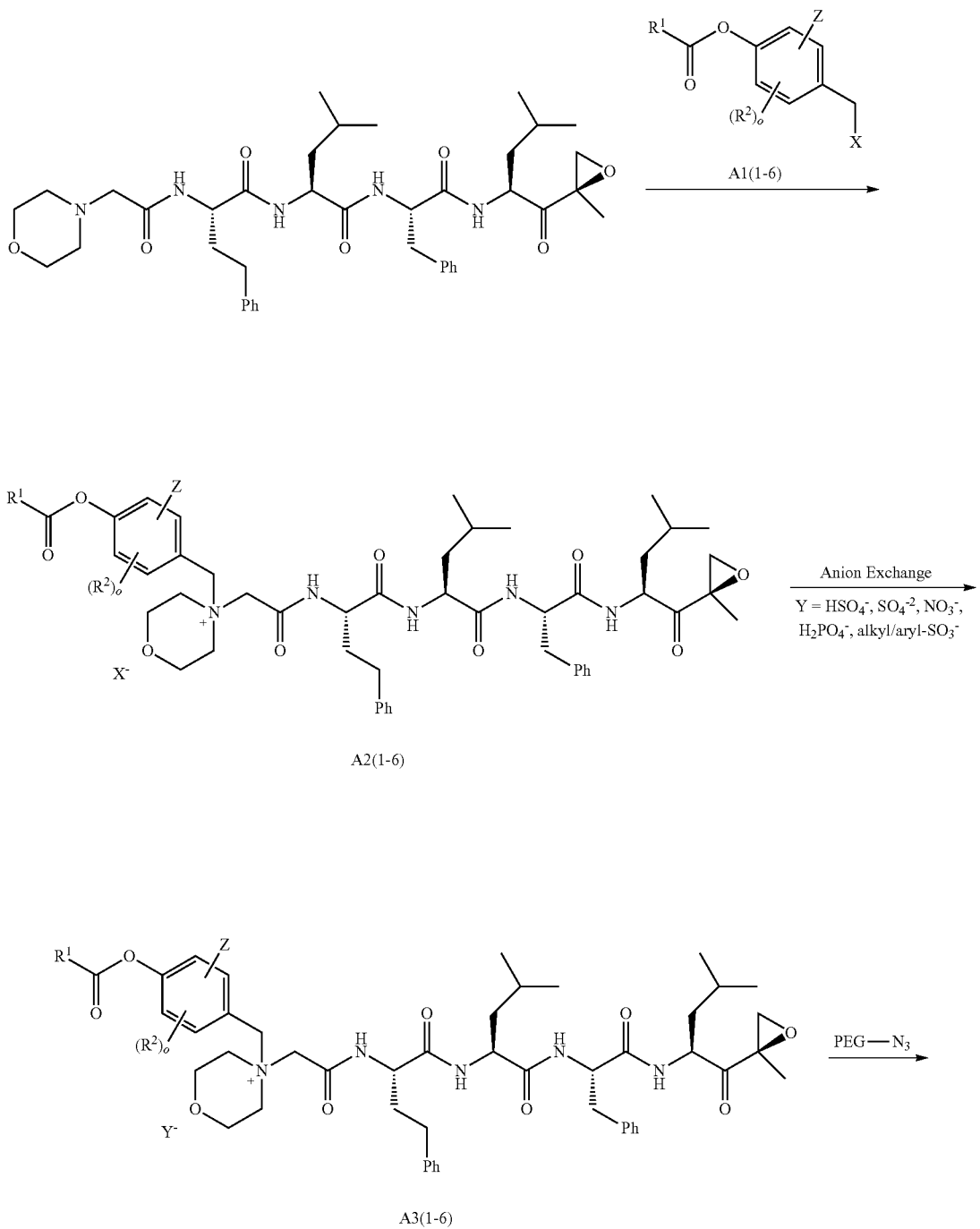

Scheme 4: Two-step polymer conjugation via azide/alkyne Click chemistry

-continued
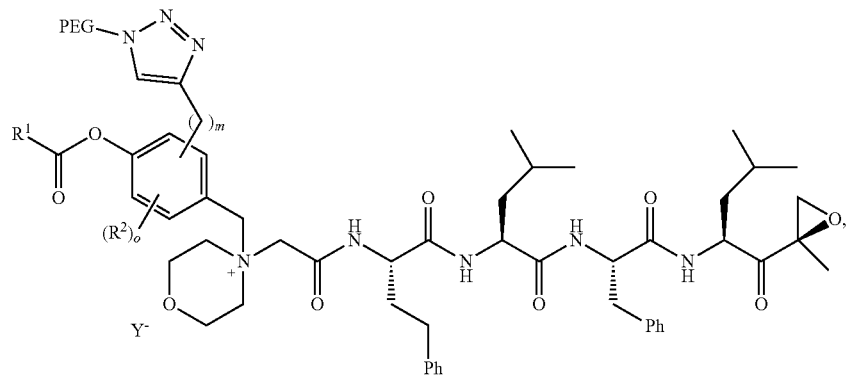
A4-1
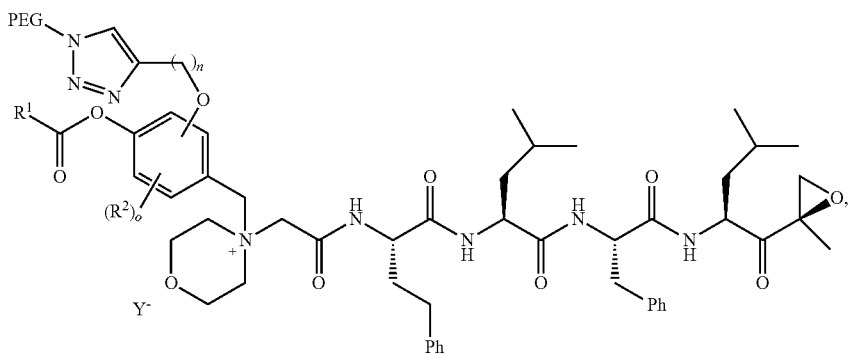
A4-2
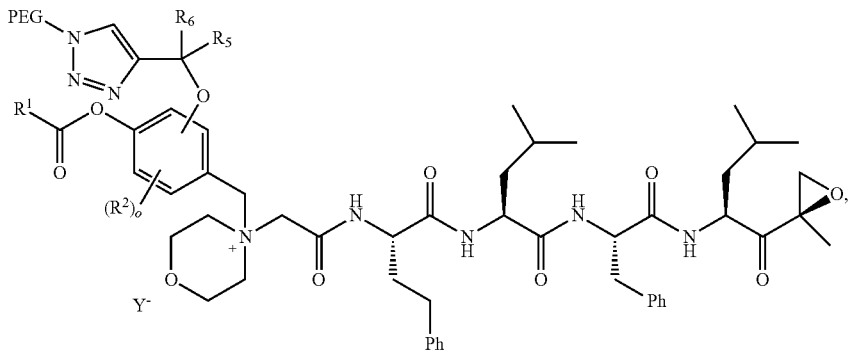
A4-3
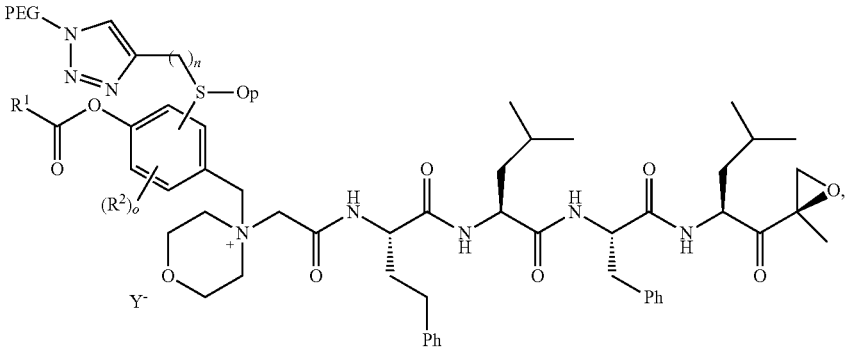
A4-4

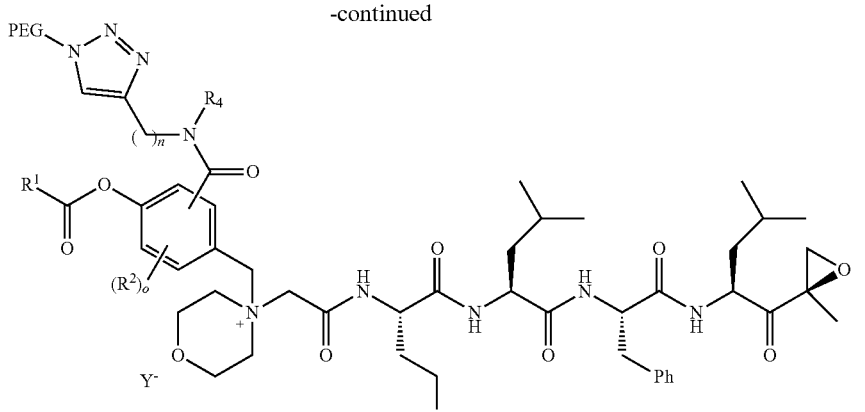

A4-5 or

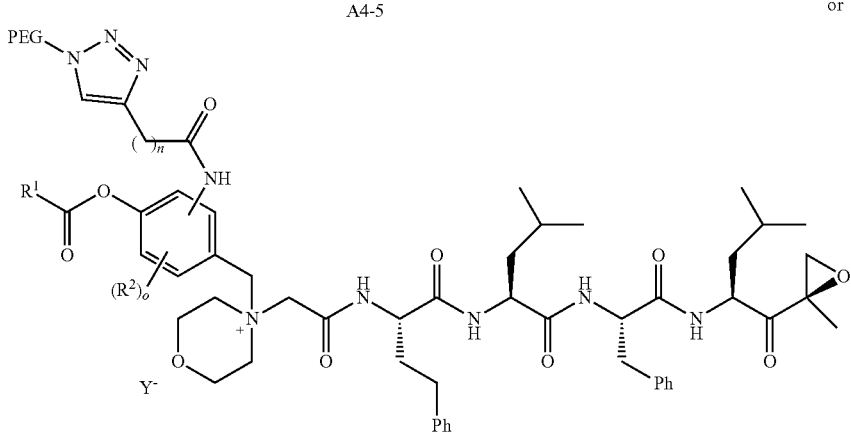

A4-6

X = Br, I
R₄ = H, Me
R₅, R₆ = H, Me
m = 0-4
n = 1-4
p = 0, 1, 2

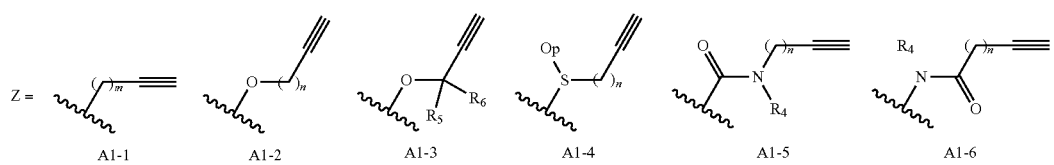

Z =   A1-1   A1-2   A1-3   A1-4   A1-5   A1-6

Scheme 4 illustrates "Click" chemistries, such as Huisgen 1, 3-dipolar azide/alkyne cycloaddition and aminooxy/aldehyde oximation that are particularly well suited for polymer and polymeric PEG attachments due to high chemical yields, inoffensive byproducts, large thermodynamic driving forces, and starting material availability.

Huisgen 1, 3-dipolar azide/alkyne cycloaddition requires that the benzyl group be substituted with an alkyne group (A1-(1-6)) capable of reacting with an azide functionalized polymeric carrier such as PEG-Azide (—N₃) to give a 1,2,3-triazole linked conjugate (A4-(1-6)). The alkyne moiety may be directly linked or linked via an alkyl spacer (A1-1), linked via an ether (A1-2,3), thioether, sulfoxide or sulfone (A1-4) bond, or linked via an amide bond (A1-5,6). Many azido substituted PEG reagents are now commercially available in a wide variety of sizes and architectures, but also may be readily prepared from any available PEG-alcohol via activation by mesylation or tosylation followed by reaction with an azide salt. The cycloaddition reaction can be performed using commercially available cuprous salt catalysts, but works more efficiently using a mixture of copper (II) (e.g. copper (II) sulfate, copper (II) methanesulfonate) and a reducing agent (e.g. sodium ascorbate) to produce Cu (I) in situ. Since copper (I) is unstable in aqueous solution and in the presence of oxygen, stabilizing ligands such as tris-(benzyltriazolylmethyl)amine (TBTA), tris(3-hydroxypropyltriazolylmethyl)amine (THPTA), 2-[4-({bis[(1-tert-butyl-1H-1,2,3-triazol-4-yl)methyl]amino}methyl)-1H-1,2,3-triazol-1-yl]ethyl hydrogen sulfate (BTTES) or 2-[4-({bis[(1-tert-butyl-1H-1,2,3-triazol-4-yl)methyl]amino}methyl)-1H-1,2,3-triazol-1-yl]acetic acid (BTTAA) may be optionally added. The reaction can be run at RT or at an elevated temperature in a variety of solvents, and mixtures of water and a variety of miscible organic solvents including alcohols, DMSO, DMF, tBuOH and acetone. The final PEG-carfilzomib product (A4-(1-6)) may be conveniently worked up by dilution of the reaction mixture with water or brine, extraction with an organic solvent such as DCM, and reprecipitation from isopropanol or ether/isopropanol mixtures until product of desired purity is obtained. The exposure of intermediates or products to anions during workup procedures, such as chloride anions in brine, typically result in a mixture of anions in the final product, and a final anion exchange resin treatment may be necessary to ensure product salt homogeneity.

The intermediate quaternary halide salt (bromide or iodide, (A2-(1-6)) can be converted to an anion which does not precipitate with the copper (I) catalyst such as methanesulfonate, bisulfate or sulfate (A3-(1-6)) to achieve high reaction yields. In addition it may be desirable to exchange the halide anion to prevent opening of the epoxide and possible formation of bromohydrin or iodohydrin side-products.

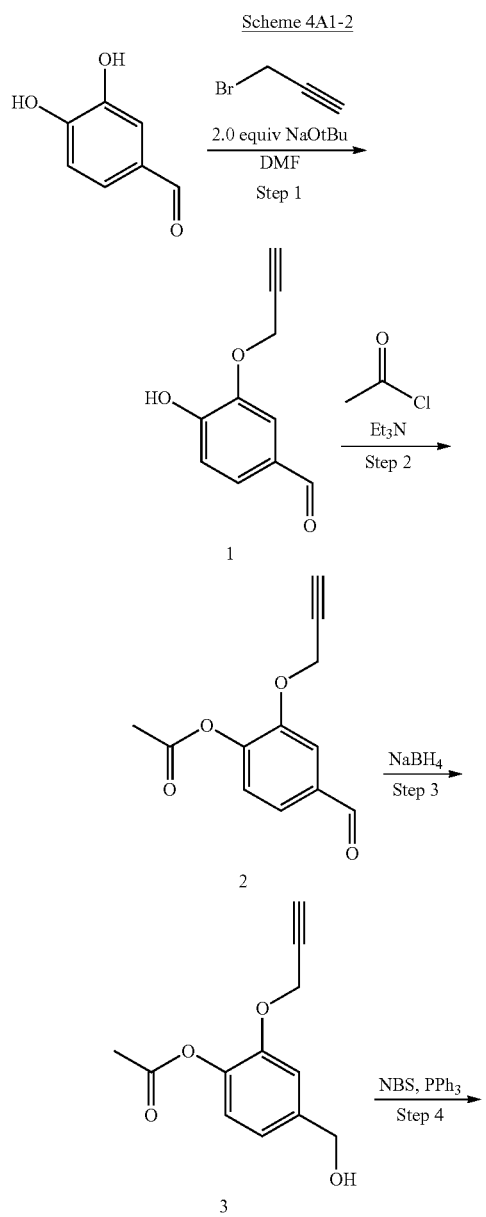

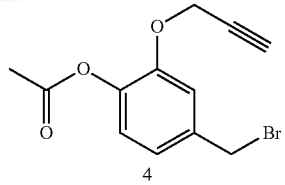

Synthesis of 4-(Bromomethyl)-2-(prop-2-ynyloxy) phenyl Acetate (Intermediate A1-2 in Scheme 4)

Step 1: 4-Hydroxy-3-(prop-2-ynyloxy)benzaldehyde (1)

To a mixture of NaOtBu in DMF (150 mL) was added 3,4-dihydroxybenzaldehyde (10 g, 72.5 mmol) in DMF (50 mL) at 20° C. The mixture was cooled with an ice bath and stirred while 3-bromoprop-1-yne (8.62 g, 72.5 mmol) was added portionwise, attempting to keep internal temperature between 15-20° C. The reaction mixture was stirred at RT for 2 hours. The mixture was diluted with water (300 mL) and extracted with EtOAc (200 mL×3). The combined organic layers were washed with water to remove DMF, dried over anhydrous $Na_2SO_4$, and concentrated to a brown solid. The residue was crystallized repeatedly from DCM/Petroleum Ether (30 mL/500 mL) to afford compound 1. 1 H NMR (CDCl3, 300 MHz): δ 9.87 (s, 1H), 7.54 (d, J=1.2 Hz, 1H), 7.49 (dd, J1=1.5 Hz, J2=8.1 Hz, 1H), 7.09 (d, J=8.1 Hz, 1H), 4.82 (m, 2H), 2.62 (m, 1H).

Step 2: 4-Formyl-2-(prop-2-ynyloxy)phenyl Acetate (2)

To a solution of compound 1 (10.00 g, 56.82 mmol) in DCM (150 mL) was added $Et_3N$ (11.48 g, 113.64 mmol) followed by acetyl chloride (5.35 g, 68.18 mmol) at 0° C. The reaction mixture was stirred at RT for 2 hours. The mixture was washed with saturated 2N aqueous HCl (100 mL) and water (50 mL), dried over anhydrous $MgSO_4$, and concentrated to afford compound 2, which was used in the next step without further purification. $^1$H NMR ($CDCl_3$, 400 MHz): δ 9.96 (s, 1H), 7.63 (d, J=1.6 Hz, 1H), 7.54 (dd, J, =1.6 Hz, 12=8.0 Hz, 1H), 7.25 (d, J=8.0 Hz, 1H), 4.79 (d, J=2.4 Hz, 2H), 2.57 (t, J=2.4 Hz, 1H), 2.35 (s, 3H).

Step 3: 4-(Hydroxymethyl)-2-(prop-2-ynyloxy)phenyl Acetate (3)

To a solution of compound 2 (12.00 g, 55.05 mmol) in DCM/MeOH (150 mL/15 mL) was added $NaBH_4$ (3.06 g, 82.57 mmol) in small portions at 0° C. The reaction mixture was stirred at RT for 30 min. The mixture was quenched by acetone (5 mL), and concentrated. The residue was purified by flash column chromatography on silica gel (Petroleum Ether/EtOAc=2:1) to afford compound 3. $^1$H NMR ($CDCl_3$, 400 MHz): δ 7.16 (d, J=1.6 Hz, 1H), 7.04 (d, J=8.0 Hz, 1H), 6.98 (dd, J, =1.6 Hz, $J_2$=8.0 Hz, 1H), 4.72 (d, J=2.4 Hz, 2H), 4.69 (s, 2H), 2.53 (t, J=2.4 Hz, 1H), 2.32 (s, 3H).

Step 4: 4-(Bromomethyl)-2-(prop-2-ynyloxy)phenyl Acetate (4)

To a solution of compound 3 (11.50 g, 52.27 mmol) in DCM (150 mL) were added $PPh_3$ (20.50 g, 78.41 mmol) and NBS (11.04 g, 62.73 mmol) at 0° C. The reaction mixture was stirred at room temperature for 0.5 hour. An excess of solvent was concentrated and the residue was purified by flash column chromatography on silica gel (Petroleum Ether/EtOAc=20:1) to afford compound 4 (7.82 g, 53% yield). $^1$H NMR (CDCl$_3$, 400 MHz): δ 7.14 (m, 1H), 7.02 (m, 2H), 4.73 (d, J=2.4 Hz, 2H), 4.48 (s, 2H), 2.55 (t, J=2.4 Hz, 1H), 2.32 (s, 3H).

in Scheme 5. The carfilzomib quaternary salt anion present in intermediates or final products may be efficiently converted to a different strong acid anion such as bisulfate, sulfate, dihydrogen phosphate, nitrate or alkyl/aryl sulfonate via anion exchange resin. An anion exchange resin such as Amberlyst A26 (OH$^-$ form) is pretreated with the desired acid or ammonium salt, and then the quaternary halide salt is passed through. Conjugates prepared from weak acid anions such as acetate, formate or lactate are unstable due to the increased basicity of the quaternary salt and incompatibility with the ester trigger group.

Scheme 5: Quaternary salt anion exchange

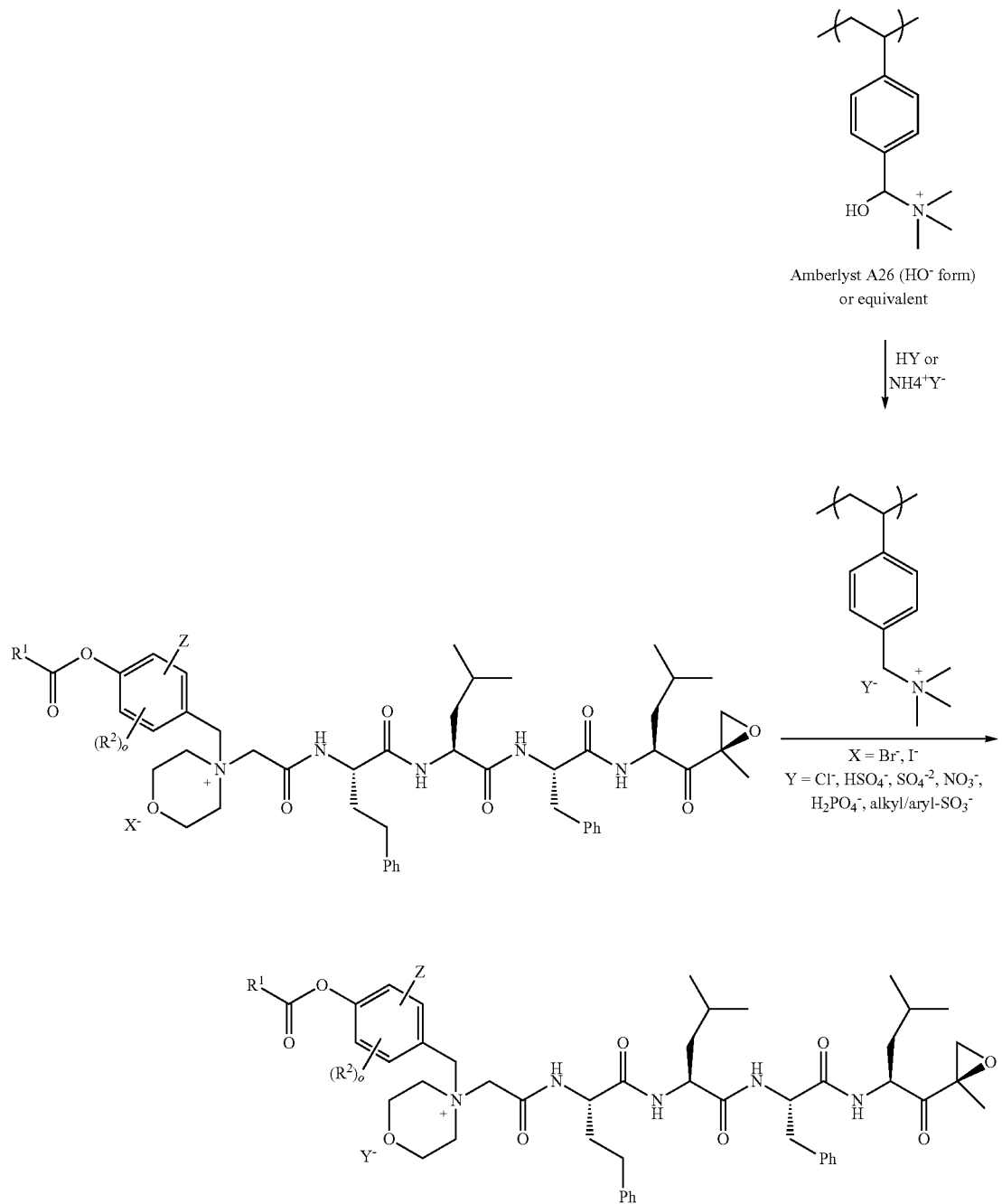

Ion exchange may be accomplished by reaction of the intermediate quaternary halide with a silver salt or more practically, passage through an ion exchange resin, as shown Scheme 6: Two-step polymer conjugation via aminooxy/carbonyl chemistry
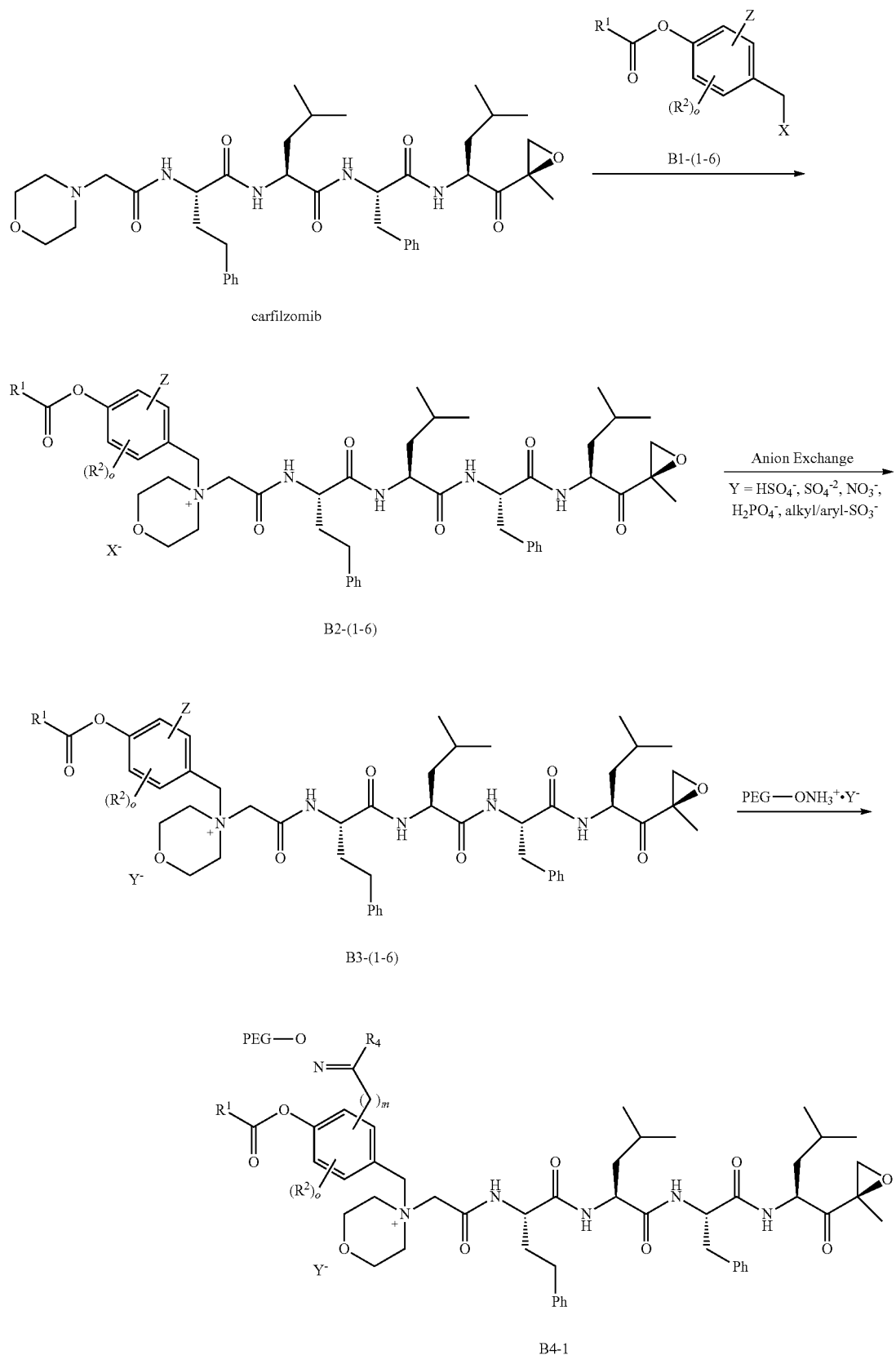

-continued
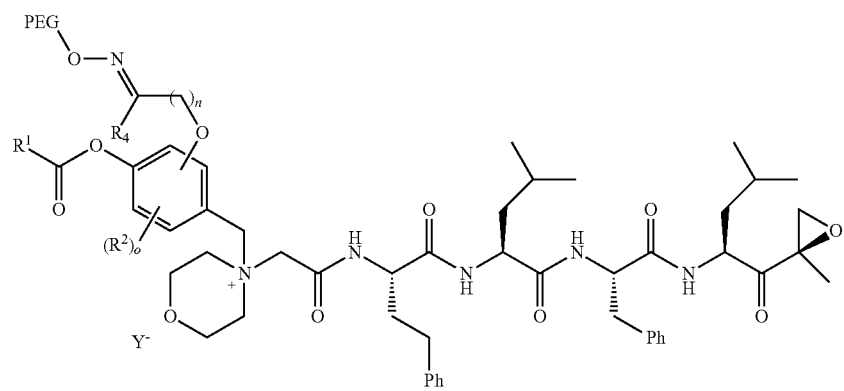
B4-2
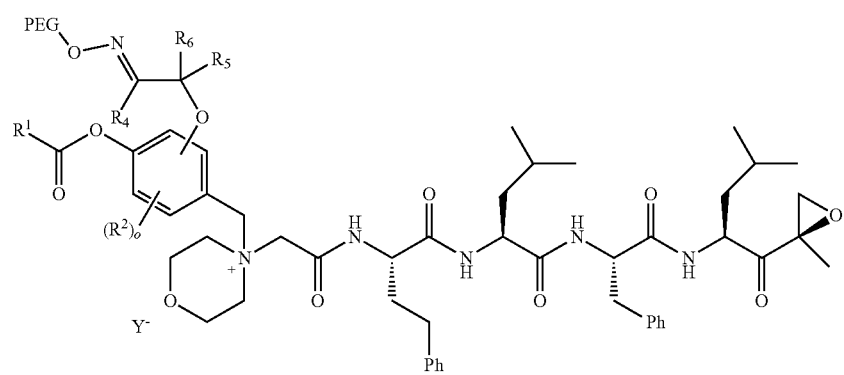
B4-3
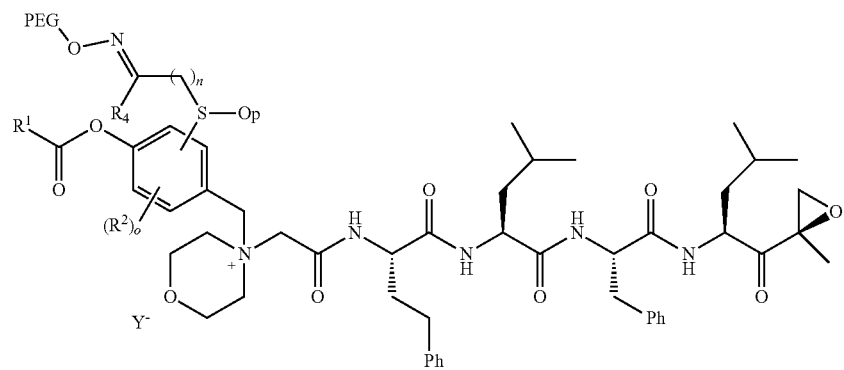
B4-4

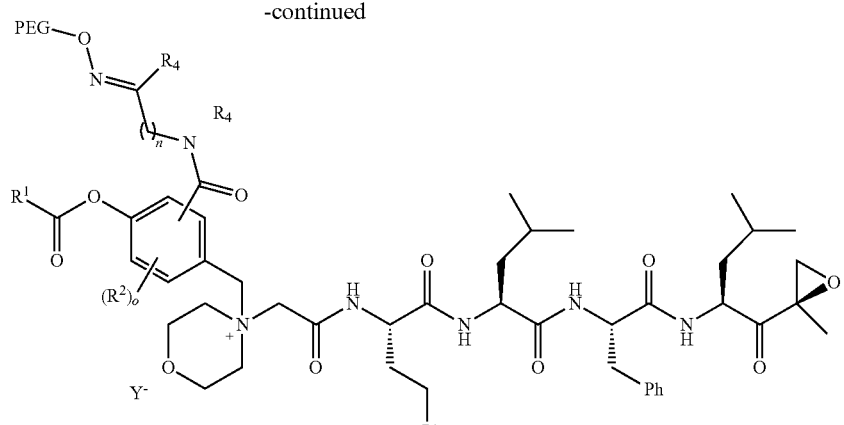

B4-5

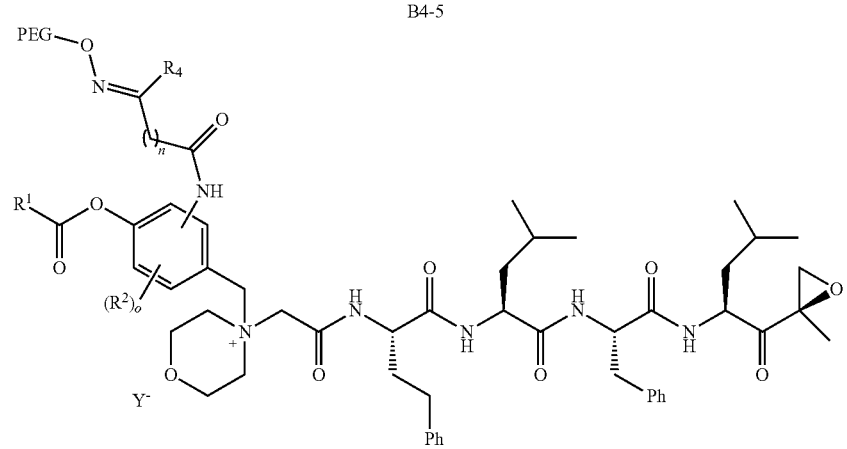

B4-6

X = Br, I
R$_4$ = H, Me
R$_5$, R$_6$ = independently H or alkyl C$_{1-3}$
m = 0 - 4
n = 1 - 4
p = 0, 1, 2

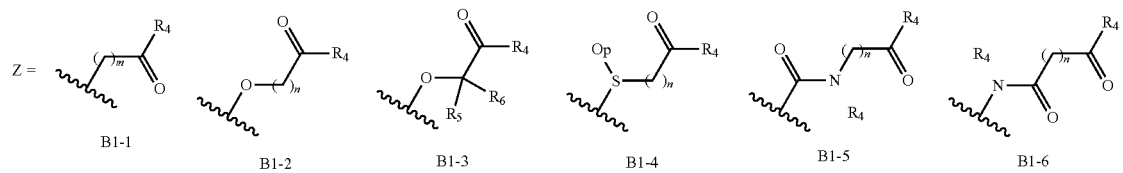

Alternatively, the benzyl group (B1-(1-6)) may be substituted with a carbonyl (aldehyde or ketone) group which is capable of reacting with an aminooxy functionalized polymeric carrier such as PEG-aminooxy (—ONH$_2$) to provide a stable oxime linked conjugate (B4-(1-6)). The carbonyl moiety may be directly linked or linked via an alkyl spacer (B1-1), linked via an ether (B1-2,3), thioether, sulfoxide or sulfone (B1-4) bond, or linked via an amide bond (B1-5,6). Carfilzomib and benzyl halide (B1-(1-6)) are allowed to react at RT or at an elevated temperature in a suitable organic solvent such as acetonitrile to provide quaternary intermediate (B2-(1-6)) as a bromide or iodide salt. It is desirable to exchange this halide anion to prevent opening of the epoxide and possible formation of bromohydrin or iodohydrin side-products. Anion exchange may be accomplished by reaction of the intermediate quaternary halide with a silver salt or more practically, passage through an ion exchange resin as described previously (Scheme 5). The carfilzomib quaternary salt intermediate (B3-(1-6)) and the PEG-ONH$_3$$^+$Y$^-$ polymer reagent are then allowed to react at RT or at an elevated temperature in a suitable organic such as DCM or a mixed aqueous organic solvent. Oximation catalysts such as aniline, p-phenylenediamine, or 5-methoxyanthranilic acid may be optionally added but are not usually necessary. Note that the carfilzomib quaternary salt intermediate (B3-(1-6)) and PEG-aminooxy reagent anion salts are identical to obviate the formation of a mixed anion salt final product and the need for any further anion manipulation. The final PEG-carfilzomib product may be conveniently worked up by evaporation of the reaction solvent and re-precipitation of the residue from isopropanol or ether/isopropanol mixtures until product of desired purity is obtained.

Scheme 7: Synthesis of PEG-Aminooxy reagents

A.

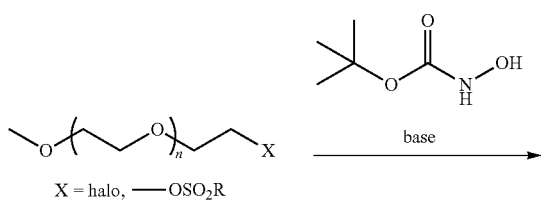

B.

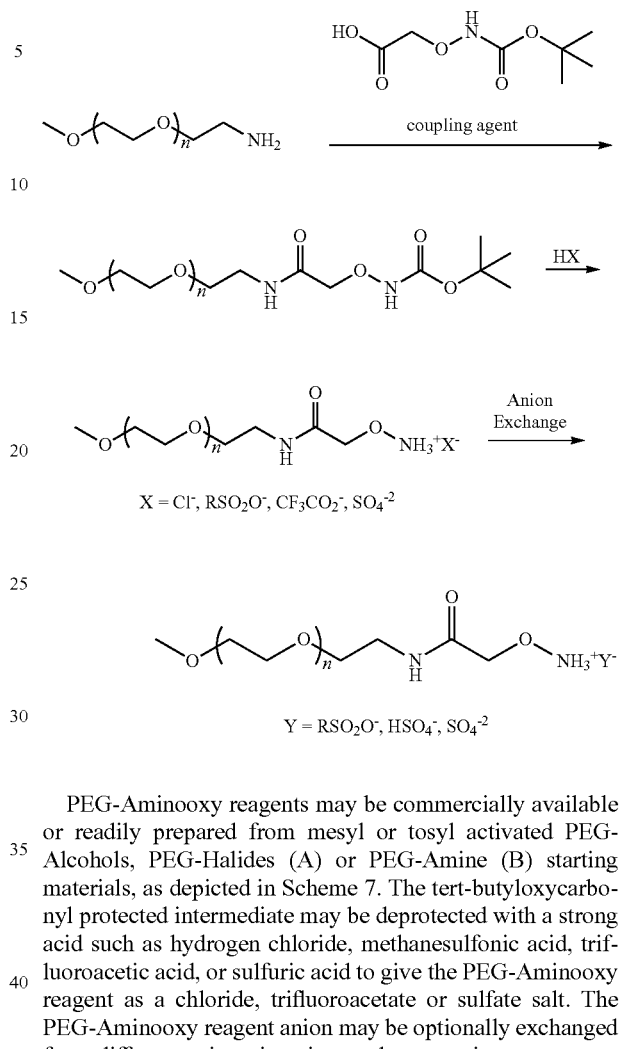

PEG-Aminooxy reagents may be commercially available or readily prepared from mesyl or tosyl activated PEG-Alcohols, PEG-Halides (A) or PEG-Amine (B) starting materials, as depicted in Scheme 7. The tert-butyloxycarbonyl protected intermediate may be deprotected with a strong acid such as hydrogen chloride, methanesulfonic acid, trifluoroacetic acid, or sulfuric acid to give the PEG-Aminooxy reagent as a chloride, trifluoroacetate or sulfate salt. The PEG-Aminooxy reagent anion may be optionally exchanged for a different anion via anion exchange resin.

Scheme 8: Oxime isomers

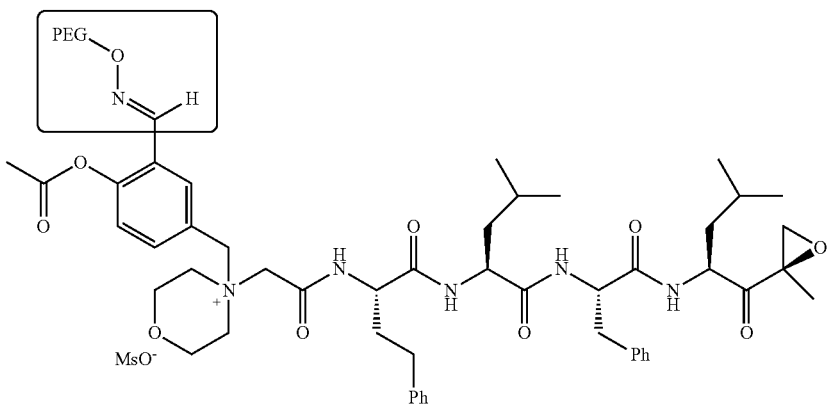

Aromatic Aldoxime (E)-isomer

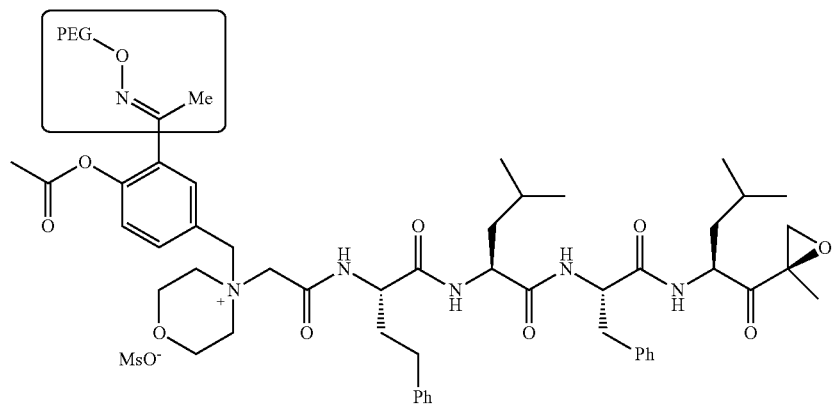

Ketoxime (E)-isomer

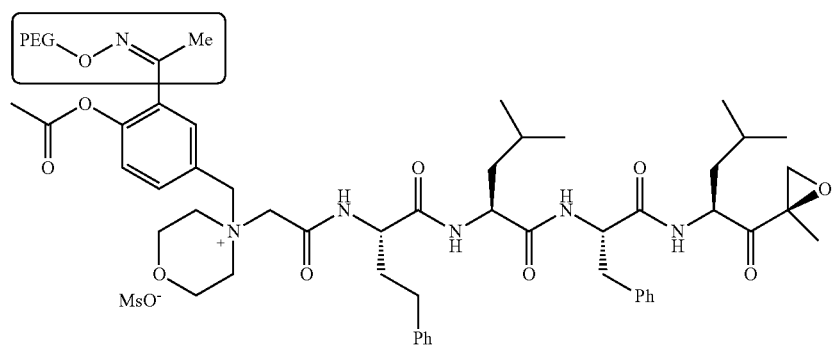

Ketoxime (Z)-isomer

It is readily understood by persons of ordinary skill in the art that oximes may exist as two geometric isomers: a syn (Z)-isomer and an anti (E)-isomer, as depicted in Scheme 8. Many of the examples in this disclosure are aromatic aldoximes and exist only as (E)-isomers. Non-aromatic aldoximes and ketoximes can usually be completely separated and obtained as a (Z)-isomer and an (E)-isomer. The pegylated non-aromatic aldoximes and ketoximes described in this invention may exist as separate (Z) and (E)-isomers or as a mixture of (Z) and (E)-isomers.

Scheme 9: Direct polymer conjugation to form quaternary salt

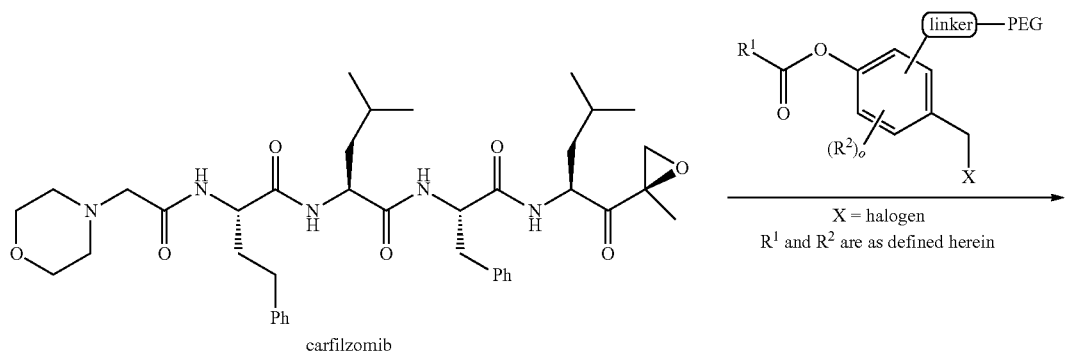

carfilzomib

X = halogen
$R^1$ and $R^2$ are as defined herein

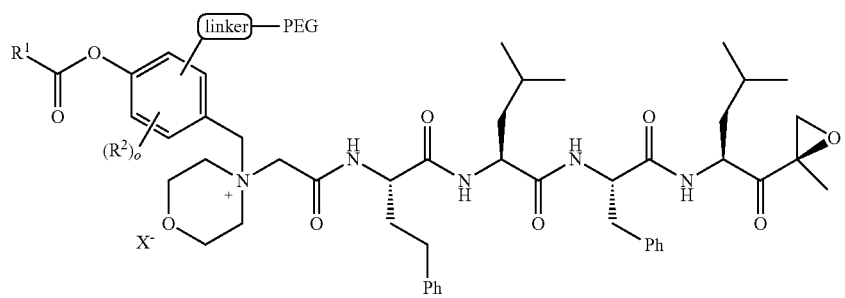

Alternatively, the carfilzomib-polymer conjugates described in this invention may be prepared in a one-step reaction of carfilzomib and a para-alkanoyloxy substituted benzyl halide pre-appended with the desired polymer chain, as shown in Scheme 9. The polymer chain may be appended via a wide variety of known chemistries or the alkyne/azide or carbonyl/aminooxy chemistries described previously. This route may be less desirable due to the difficulty in separating PEG containing products from unreacted pegylated starting materials.

Representative Compound Examples for Use in the Invention

The following pegylated carfilzomib compounds are representative examples of pegylated carfilzomib compound that may be used in the invention and are not intended to be construed as limiting the scope of the present invention. The pegylated carfilzomib compounds were prepared using the following two general PEG linking methods (A and B).

PEG Triazole-Linker Method A

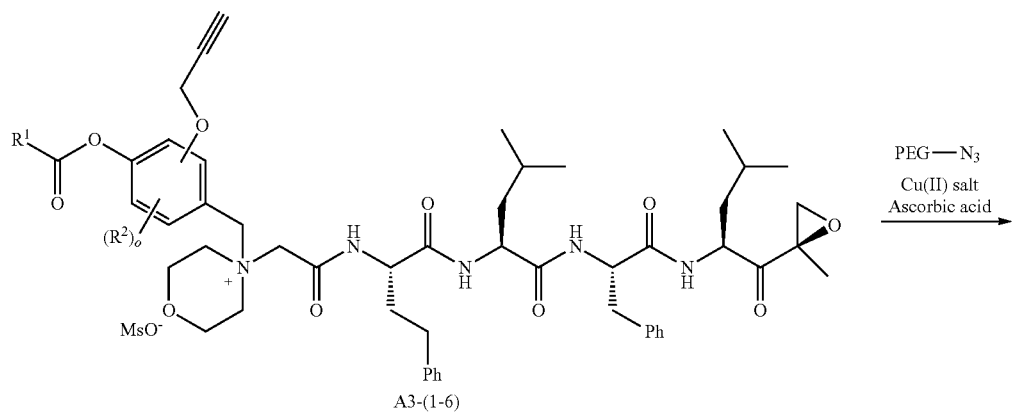

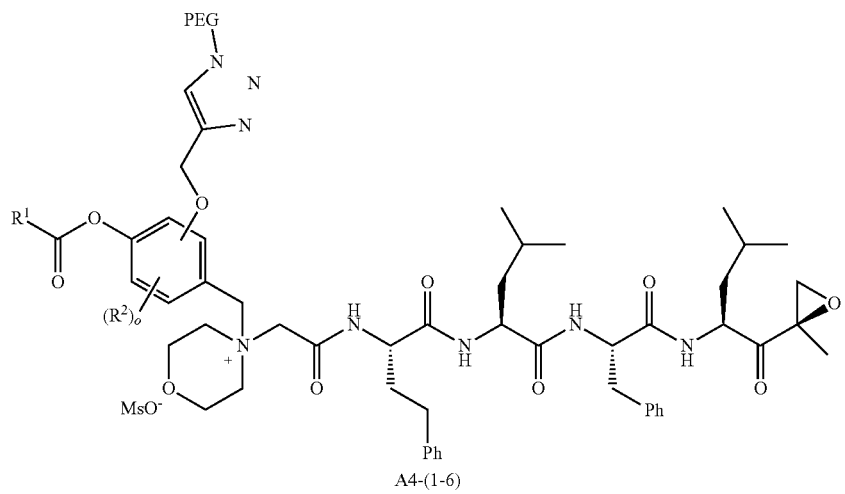

Carfilzomib quaternary salt intermediate A3-(1-6) (1.5 eq), PEG-Azide (1 eq) and (L)-ascorbic acid (0.75 eq) were mixed in DMF (50 mL/mmol PEG-Azide) to give a cream-colored suspension. The mixture was stirred vigorously for 5 minutes and a solution of copper (II) sulfate pentahydrate (0.3 eq) in water (10 mL/mmol PEG-Azide) added rapidly dropwise. The reaction darkened immediately to a yellowish-brown color and the suspension turned clear within 5 min. After 1 hour, a second portion of ascorbic acid (0.75 eq) was added and the reaction mixture stirred for 60 minutes. A third portion of ascorbic acid (0.38 eq) was added and the reaction mixture stirred overnight at RT. Water (100 mL/mmol PEG-Azide) and NaCl (15 g/mmol PEG-Azide) were added and the mixture stirred until the NaCl dissolved. The product was extracted with DCM (3×35 mL/mmol PEG-Azide). The extract was dried over anhydrous sodium sulfate, filtered, and concentrated under vacuum at 40° C. The residue was dissolved in isopropanol (125 mL/mmol PEG-Azide) at 40° C. Once the solids dissolved completely, diethyl ether (90 mL/mmol PEG-Azide) was added and the solution cooled in an ice bath. The resulting solid was filtered and the filter cake washed with 2-propanol and diethyl ether each twice. The filter cake was dissolved in DCM and concentrated under vacuum. The residue was dissolved in warm (40° C.) isopropanol (200 mL/mmol PEG-Azide) and then allowed to cool in an ice bath. The resulting solid was filtered and the filter cake washed with 2-propanol and diethyl ether each twice and then dried under vacuum.

Carfilzomib quaternary salt intermediate B3-(1-6) (1 eq), PEG-ONH$_3$$^+$MsO$^-$ (0.8 eq) and 5-methoxyanthranilic acid (oximation catalyst, 0.3 eq) in DCM (15 mL/mmol B3-(1-6)) were stirred at RT until complete consumption of the PEG reagent was observed by HPLC (ELS detector). The reaction mixture was evaporated to dryness and the residue dissolved in isopropanol (15 mL/mmol B3-(1-6)) at 40° C. The clear solution was cooled to RT and ether (5 mL/mmol B3-(1-6)) added to induce crystallization. The mixture was cooled in an ice bath for 5-10 minutes and the formed solid collected by filtration. Recrystallization from isopropanol/ether was repeated one or two more times until all the unreacted carfilzomib quaternary salt intermediate B3-(1-6) was removed as detected by HPLC. The final solid was dried under vacuum at 30° C. Typical yields: 60-80%; Typical reaction times: 10-30 min for intermediates containing an aldehyde function, 24 h for intermediates with a ketone function.

Examples of PEG-Carfilzomib compounds prepared, PEG architecture and PEG linker methodology are listed in Table 1. Table 1 further includes the size and weight (Daltons) of the PEG adduct and method used to append the PEG moiety to the carfilzomib backbone.

PEG Oxime-Linker Method B

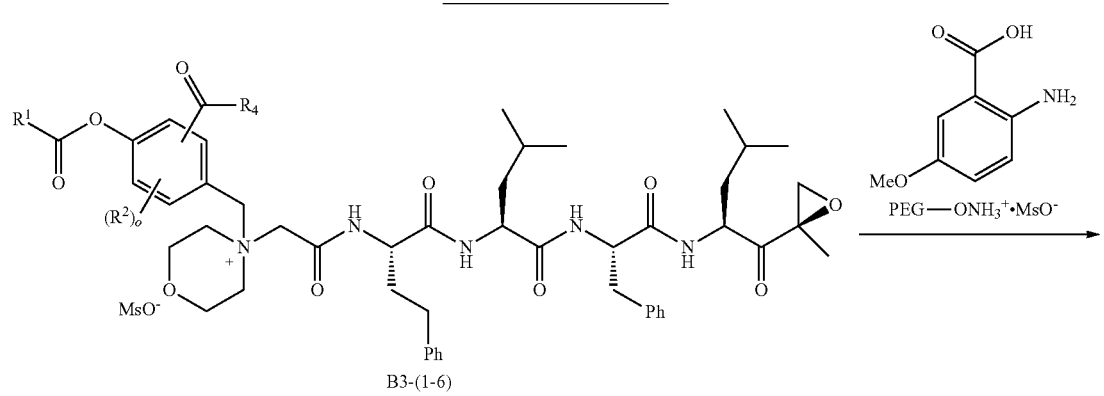

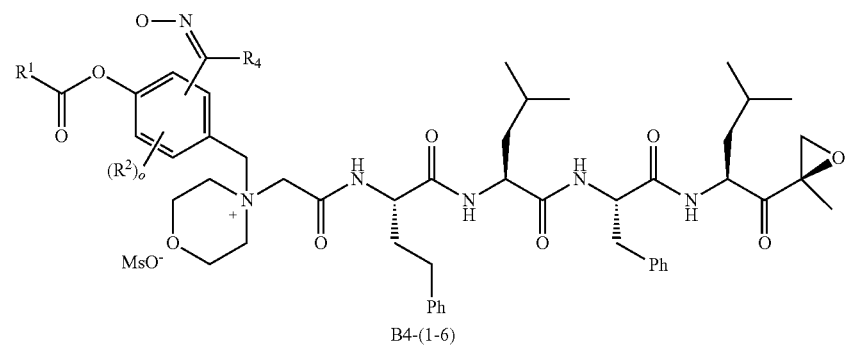

TABLE 1
| Example | Structure | PEG Size/Arms | PEG Linker Method |
|---|---|---|---|
| 1 | 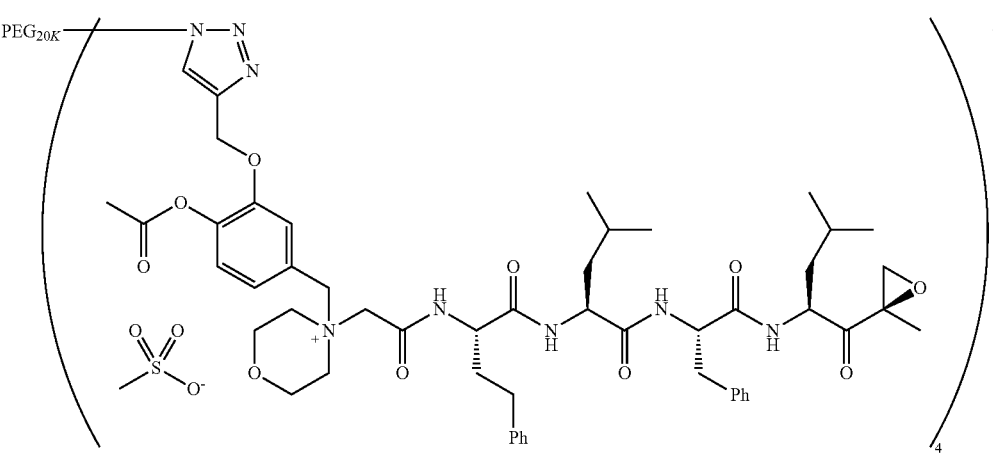 | 20K/4 | A |
| 2 | 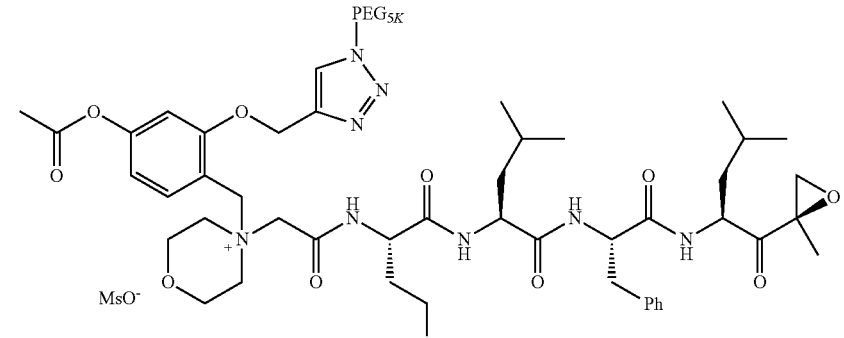 | 5K/1 | A |
| 3 | 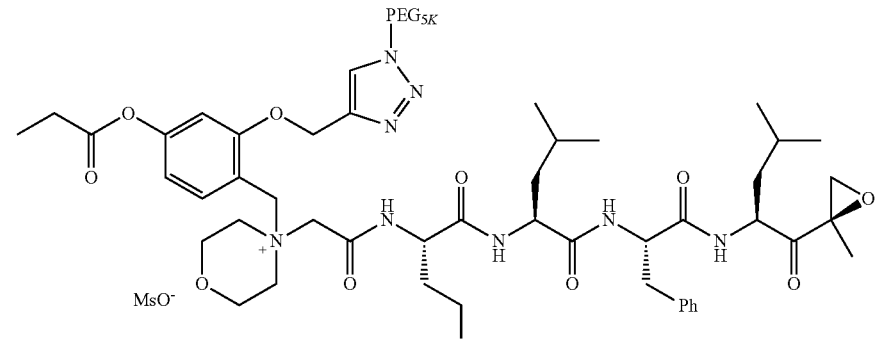 | 5K/1 | A |

TABLE 1-continued

| Example | Structure | PEG Size/Arms | PEG Linker Method |
|---|---|---|---|
| 4 | 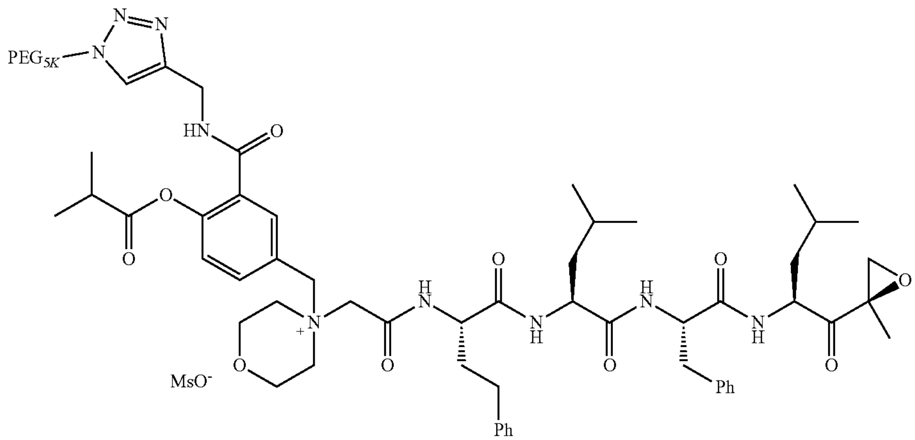 | 5K/1 | A |
| 5 | 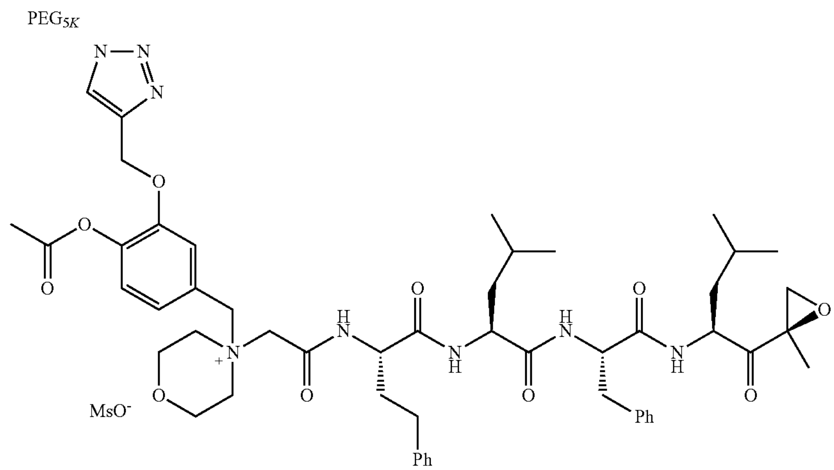 | 5K/1 | A |
| 6 | 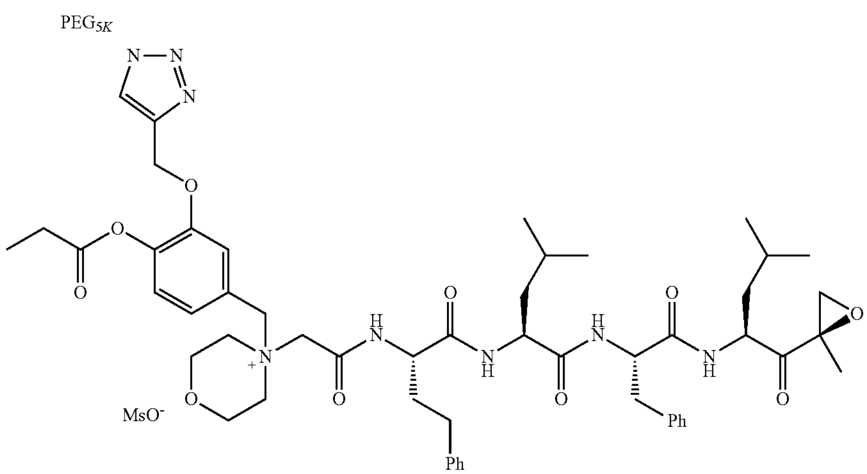 | 5K/1 | A |

TABLE 1-continued
| Example | Structure | PEG Size/Arms | PEG Linker Method |
|---|---|---|---|
| 7 | PEG5K 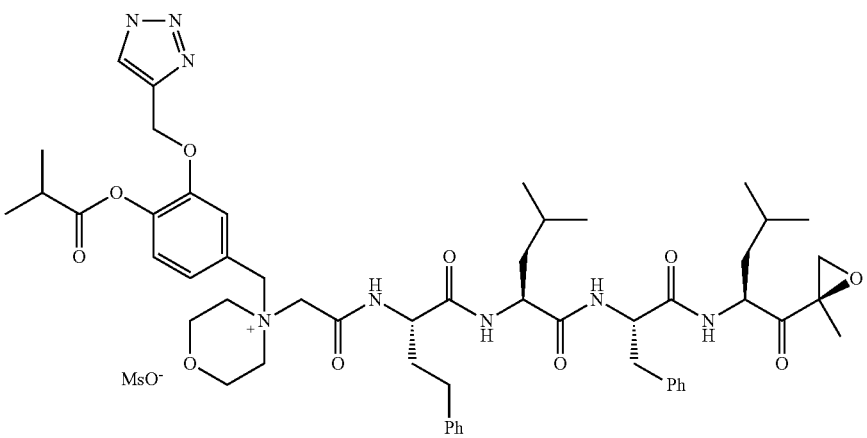 | 5K/1 | A |
| 8 | PEG5K 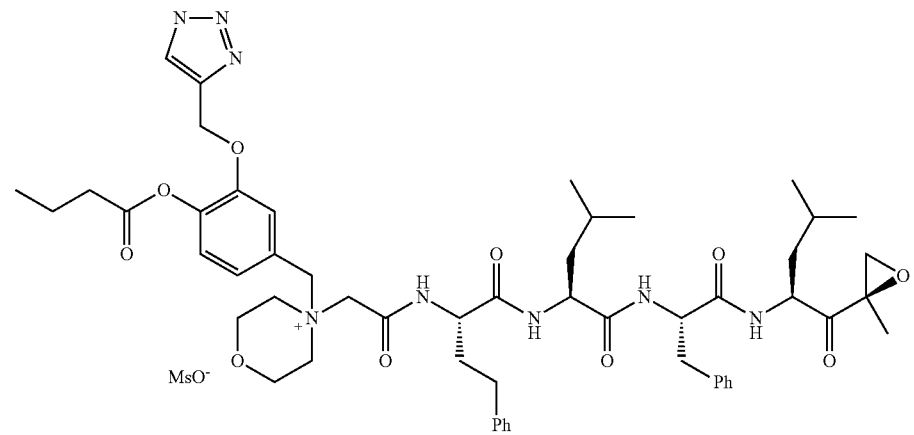 | 5K/1 | A |
| 9 | PEG5K 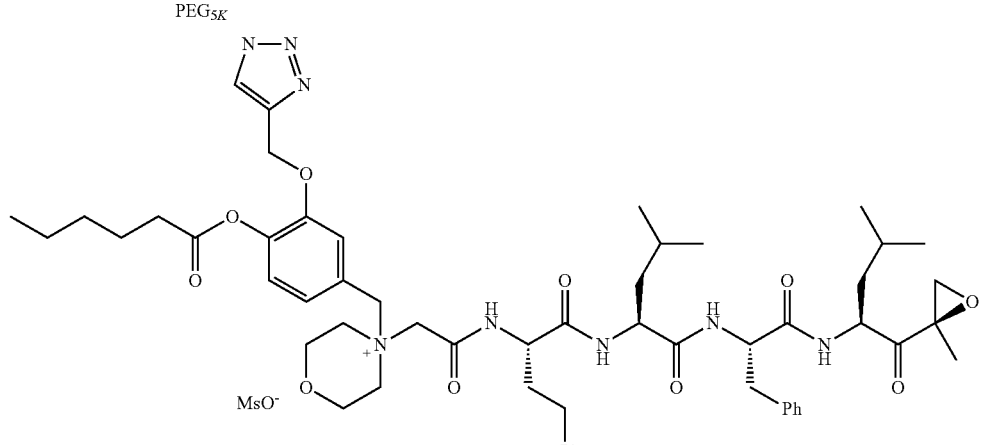 | 5K/1 | A |

TABLE 1-continued
| Example | Structure | PEG Size/Arms | PEG Linker Method |
|---|---|---|---|
| 10 | 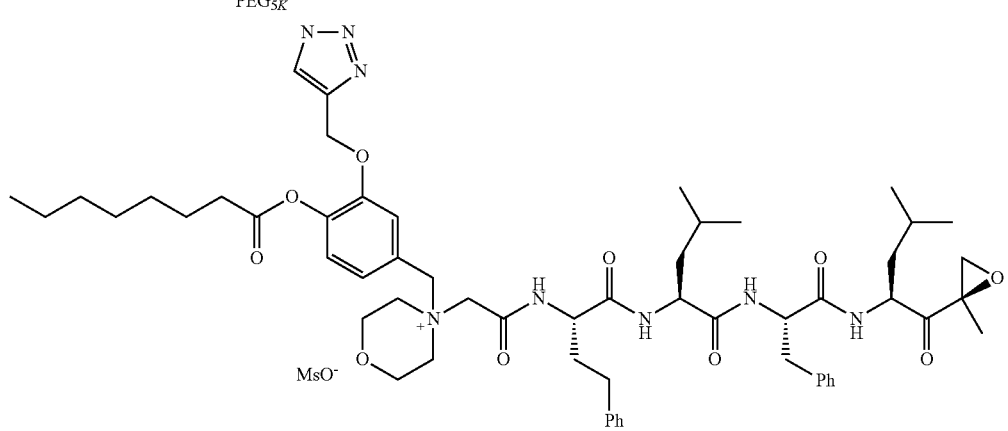 | 5K/1 | A |
| 11 | 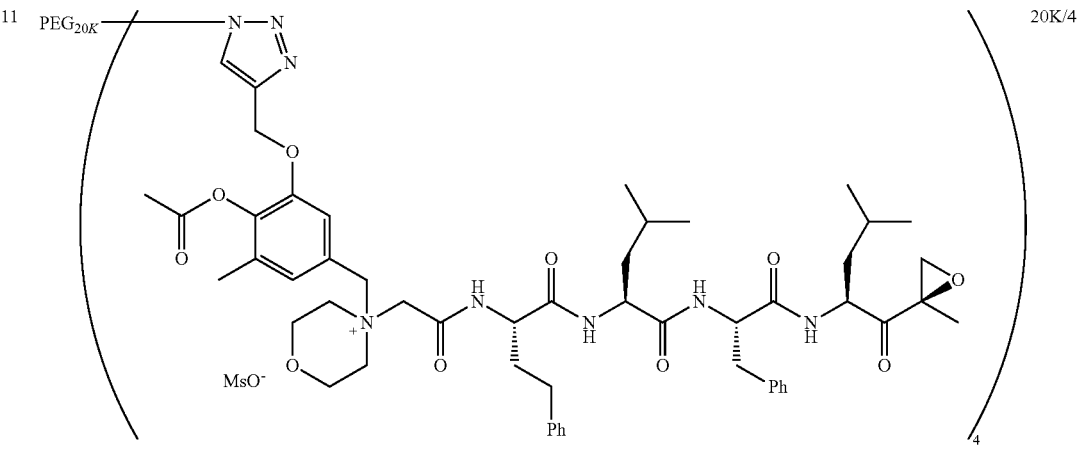 | 20K/4 | A |
| 12 | 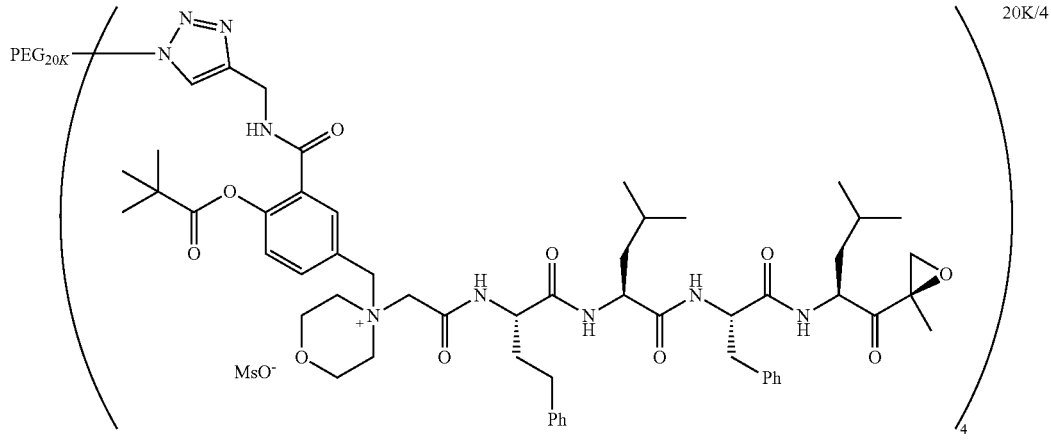 | 20K/4 | A |

TABLE 1-continued

| Example | Structure | PEG Size/Arms | PEG Linker Method |
|---|---|---|---|
| 13 | 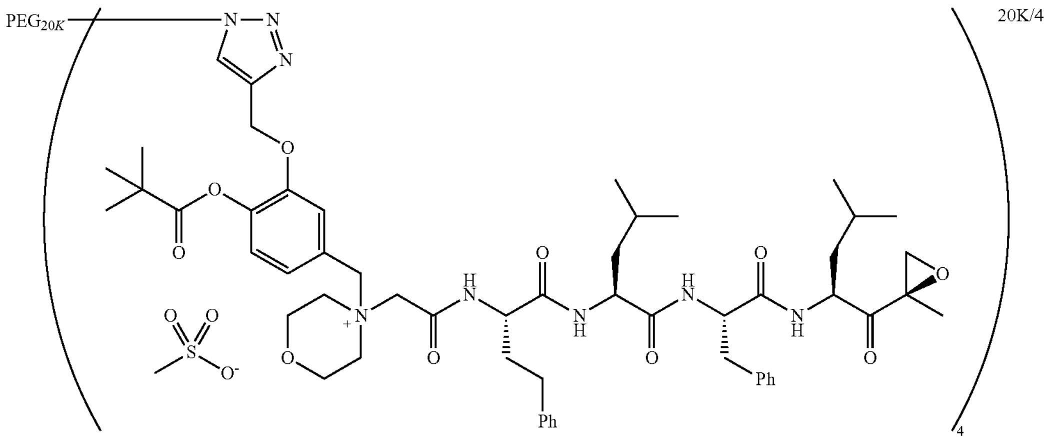 | 20K/4 | A |
| 14 | 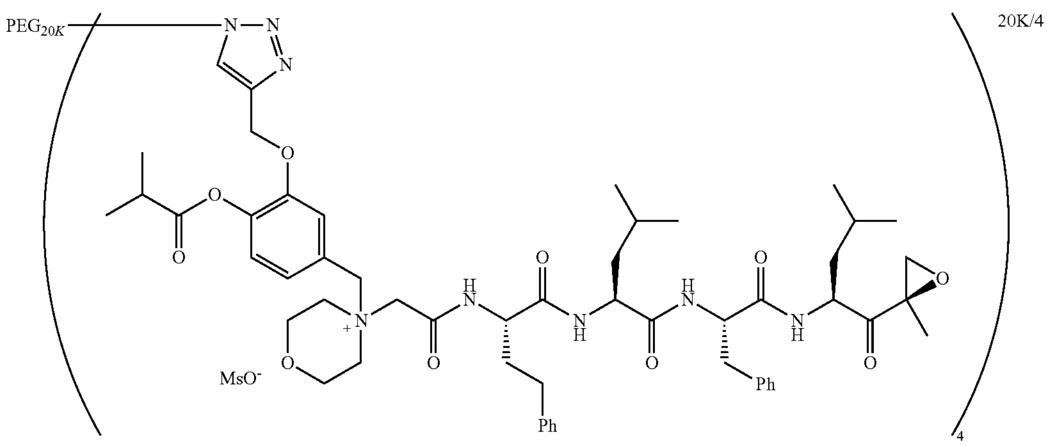 | 20K/4 | A |
| 15 | 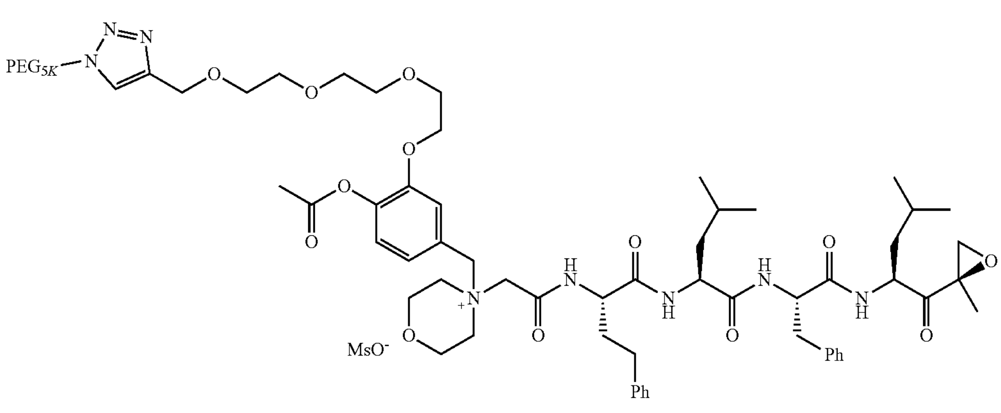 | 5K/1 | A |

TABLE 1-continued
| Example | Structure | PEG Size/Arms | PEG Linker Method |
|---|---|---|---|
| 16 | 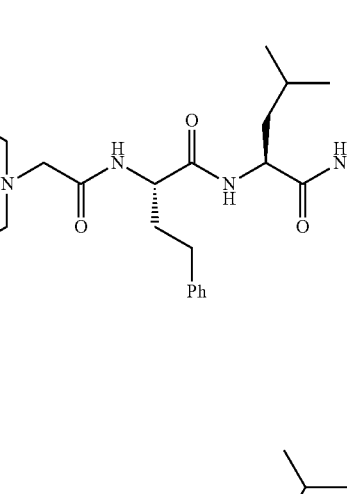 | 5K/1 | B |
| 17 | 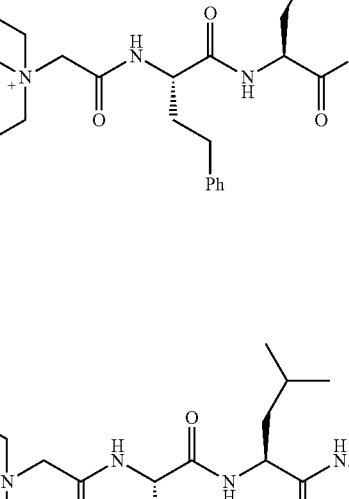 | 5K/1 | B |
| 18 | 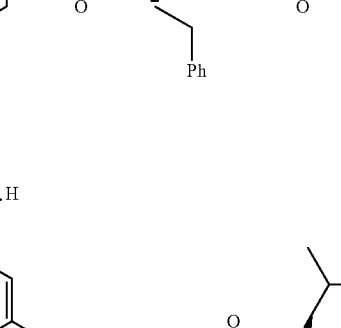 | 5K/1 | B |
| 19 | 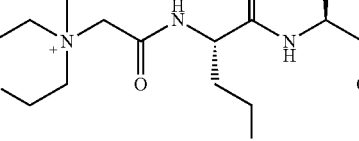 | 5K/1 | B |

TABLE 1-continued

| Example | Structure | PEG Size/Arms | PEG Linker Method |
|---|---|---|---|
| 20 | 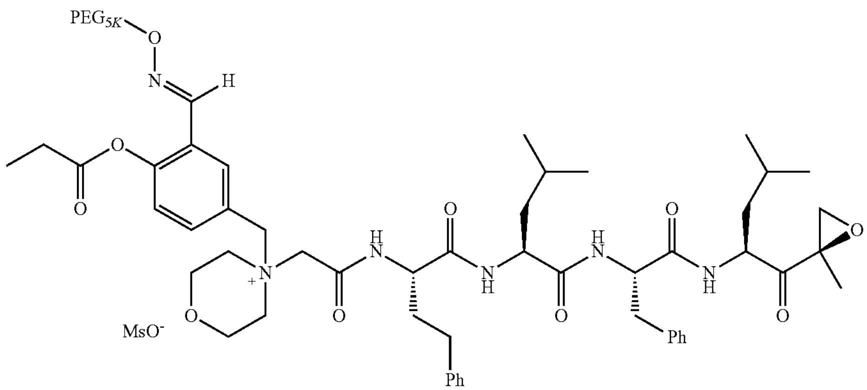 | 5K/1 | B |
| 21 | 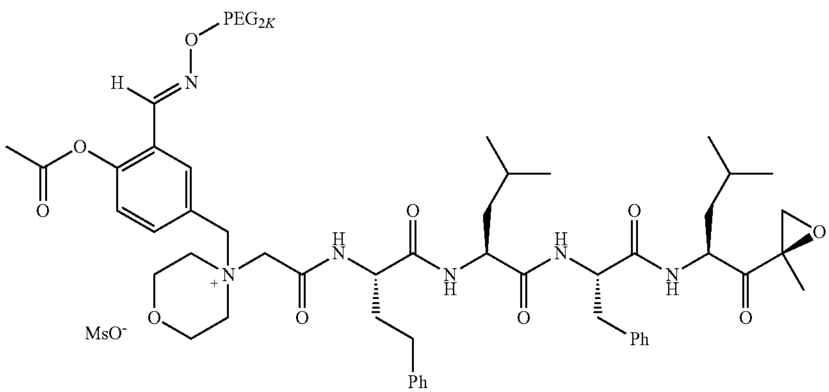 | 2K/1 | B |
| 22 | 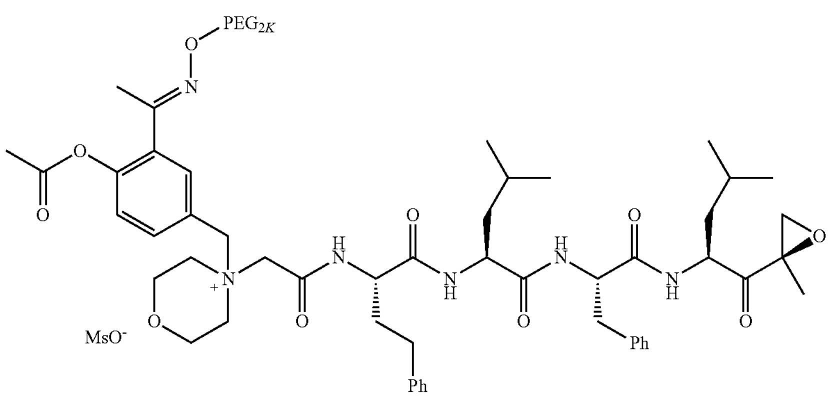 | 2K/1 | B |
| 23 | 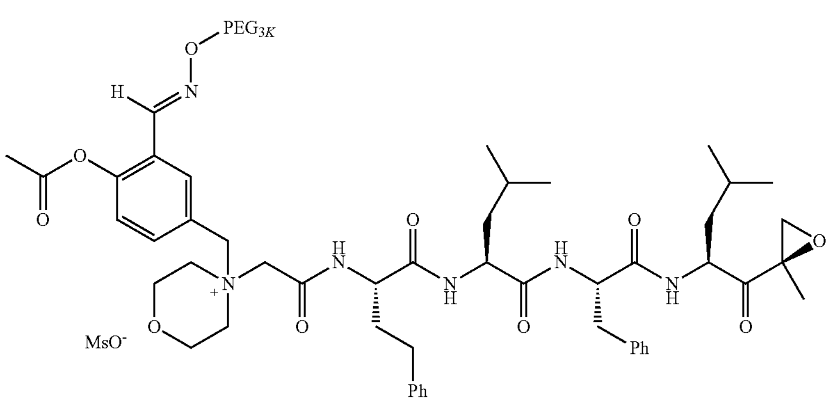 | 3K/1 | B |

TABLE 1-continued

| Example | Structure | PEG Size/Arms | PEG Linker Method |
|---|---|---|---|
| 24 | 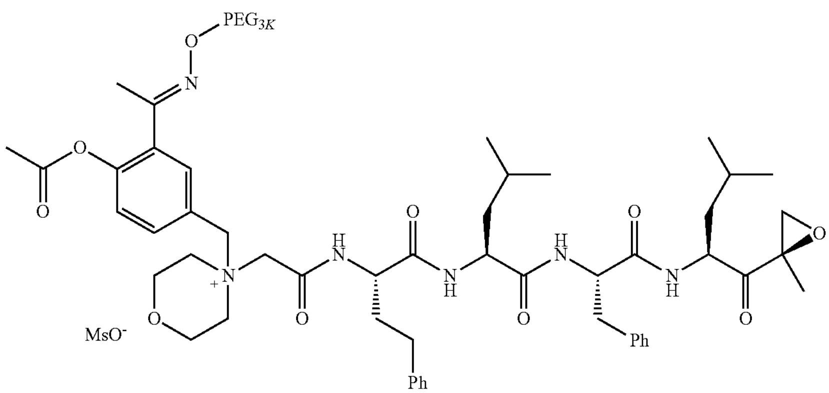 | 3K/1 | B |
| 25 | 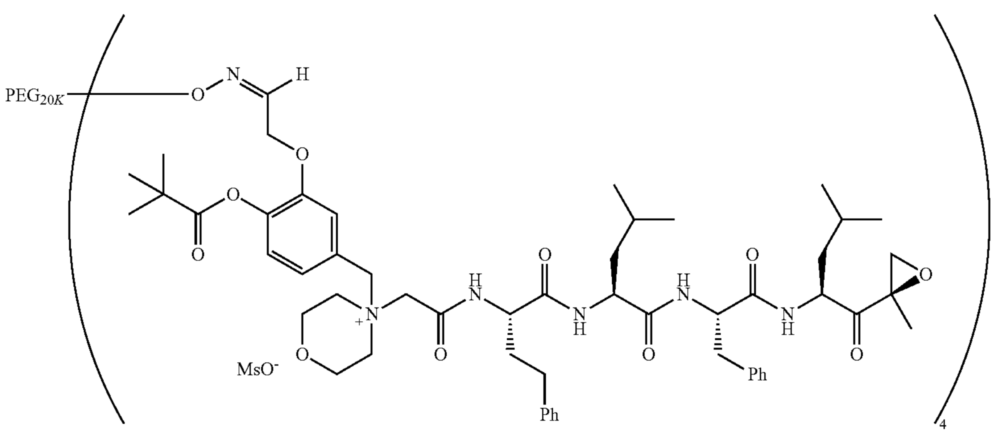 | 20K/4 | B |
| 26 | 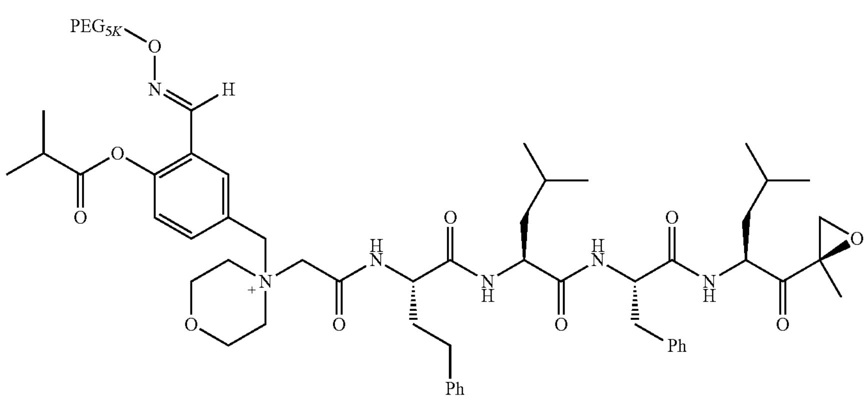 | 5K/1 | B |

TABLE 1-continued

| Example | Structure | PEG Size/Arms | PEG Linker Method |
|---|---|---|---|
| 27 | 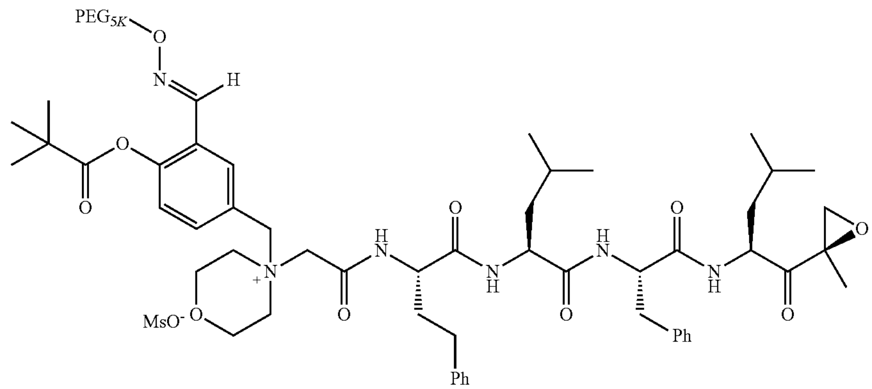 | 5K/1 | B |
| 28 | 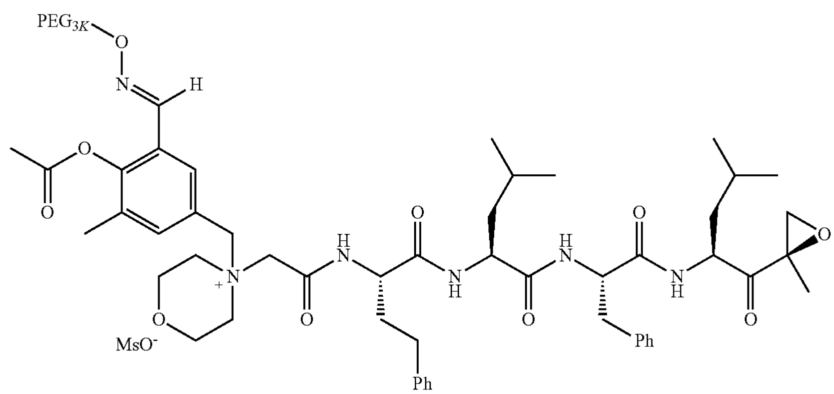 | 3K/1 | B |
| 29 | 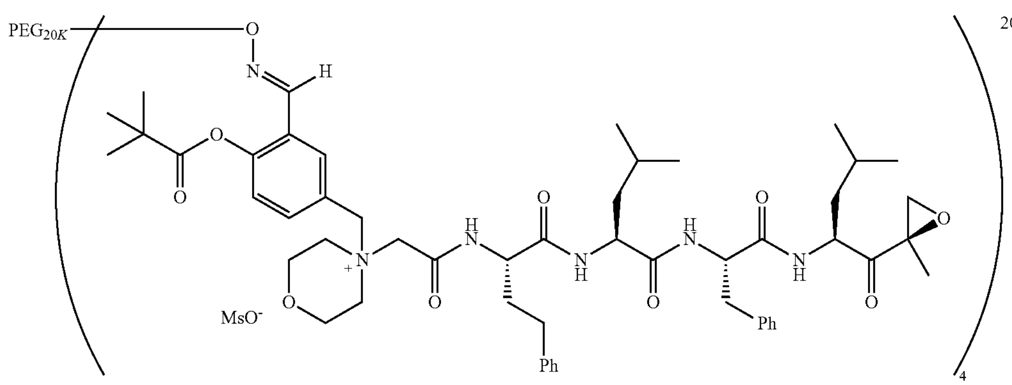 | 20K/4 | B |
| 30 | 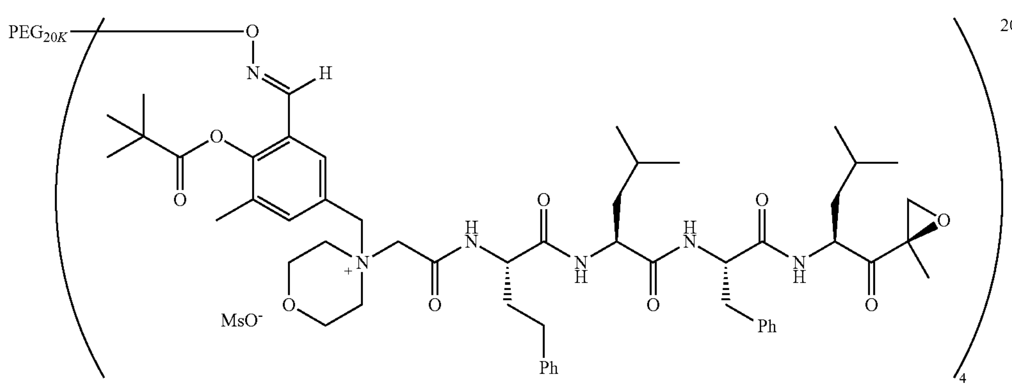 | 20K/4 | B |

TABLE 1-continued
| Example | Structure | PEG Size/Arms | PEG Linker Method |
|---|---|---|---|
| 31 | 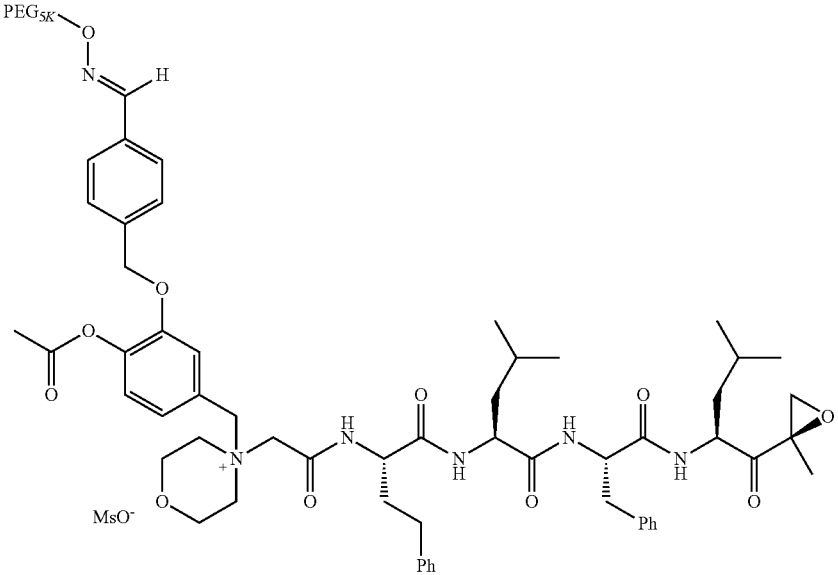 | 5K/1 | B |
| 32 | 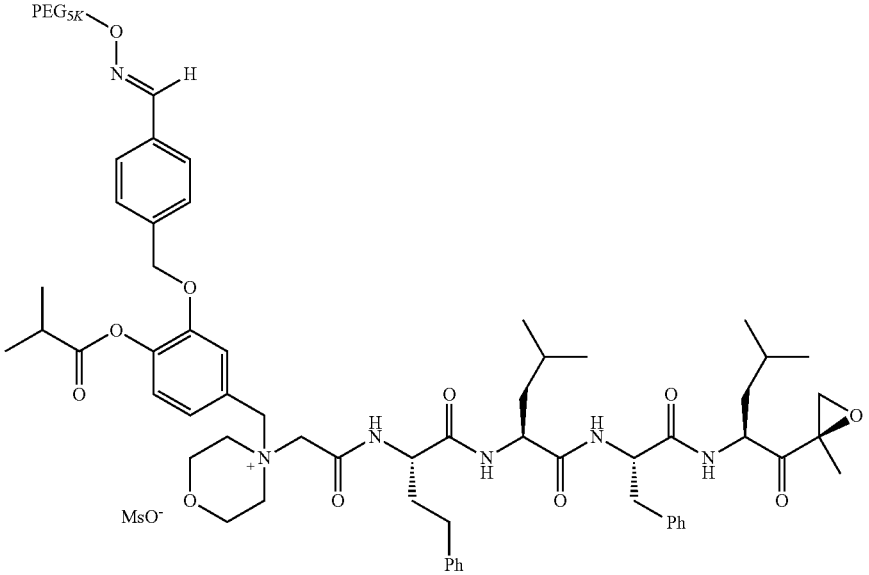 | 5K/1 | B |

TABLE 1-continued

| Example | Structure | PEG Size/Arms | PEG Linker Method |
|---|---|---|---|
| 33 | 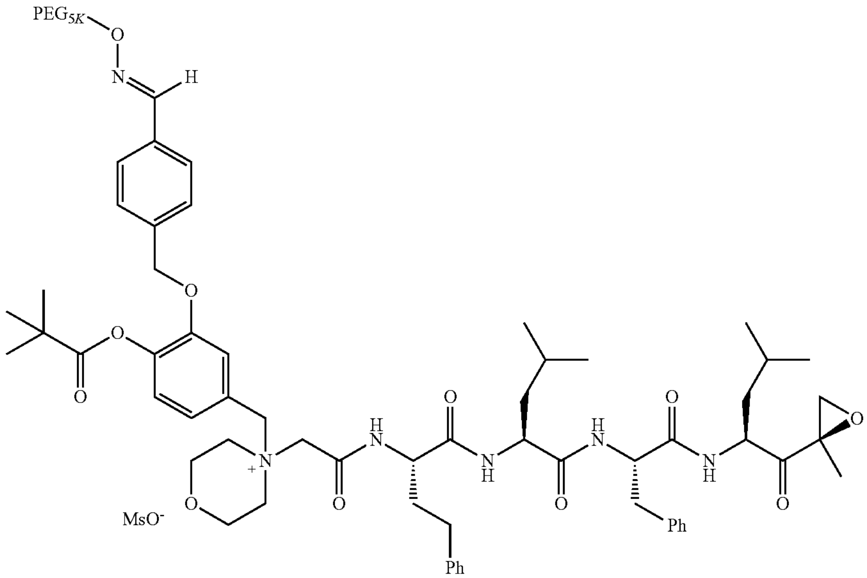 | 5K/1 | B |
| 34 | 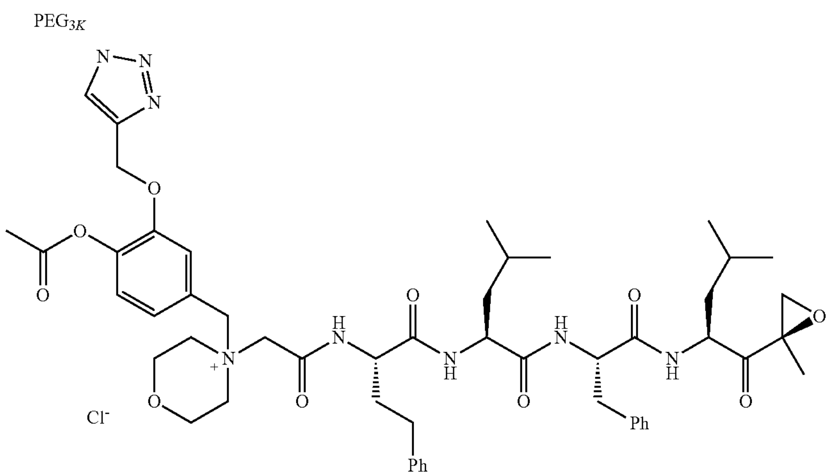 | 3K/1 | A |
| 35 | 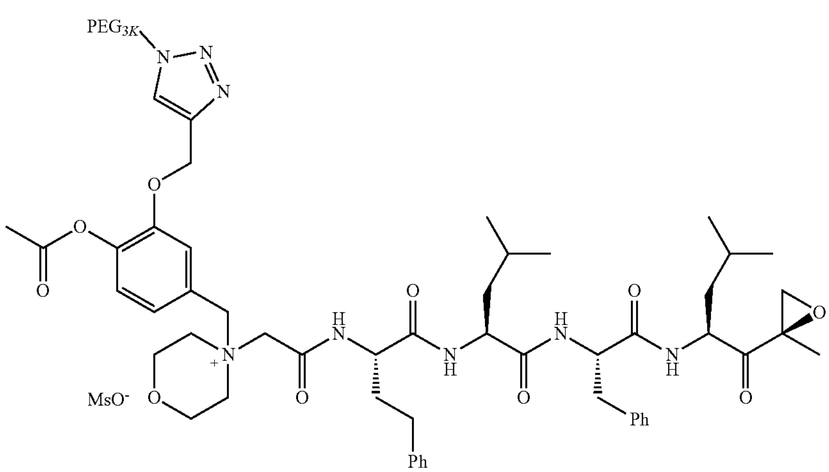 | 3K/1 | A |

TABLE 1-continued

| Example | Structure | PEG Size/Arms | PEG Linker Method |
|---|---|---|---|
| 36 | 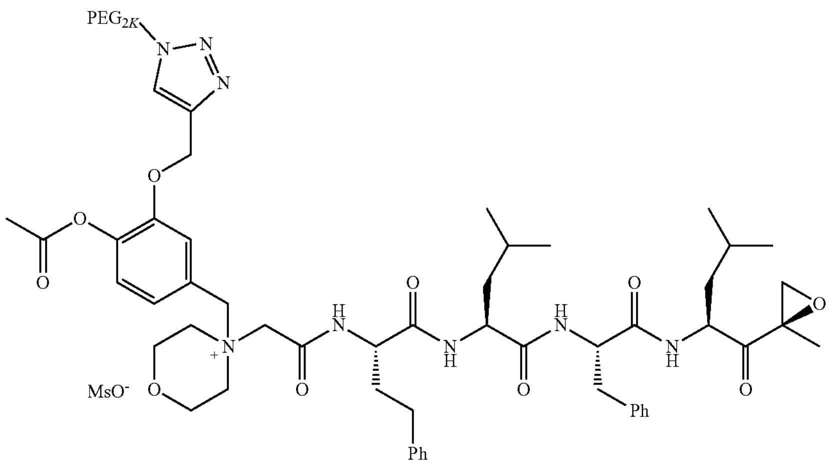 | 2K/1 | A |
| 37 | 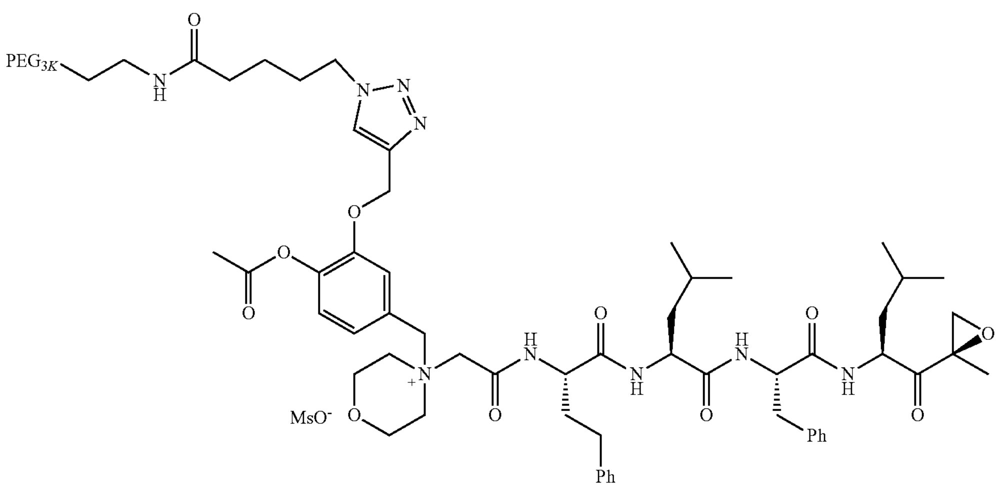 | 3K/1 | A |
| 38 | 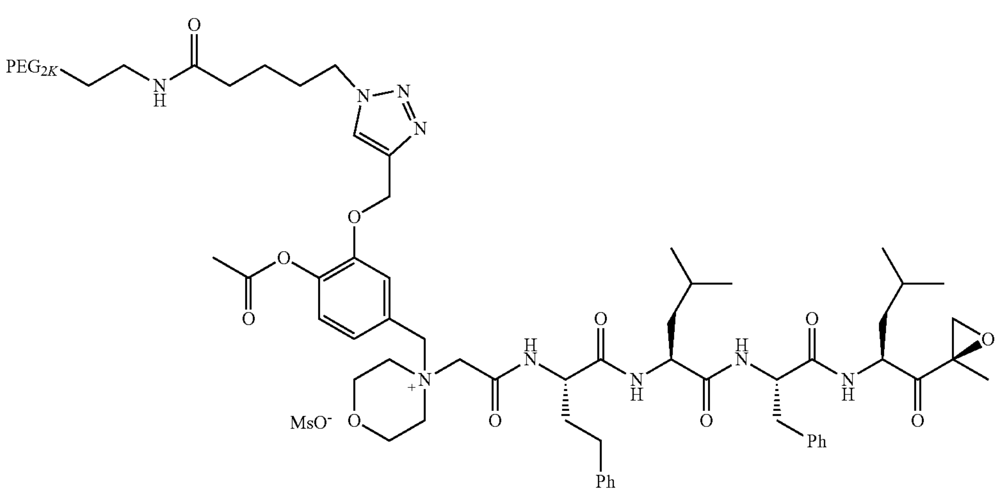 | 2K/1 | A |

| Example | Structure | PEG Size/Arms | PEG Linker Method |
|---|---|---|---|
| 39 | 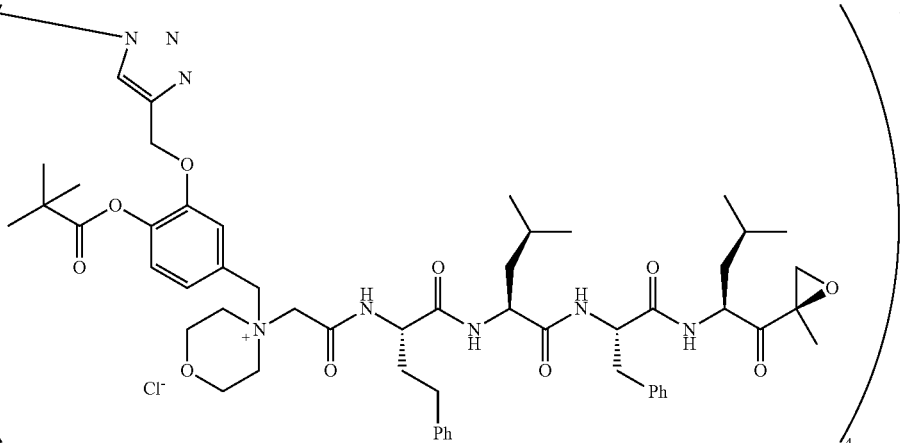 | 20K/4 | B |
Example 2: 4-(4-Acetoxy-2-((1-PEG$_{5K}$-1H-1,2,3-triazol-4-yl)methoxy)benzyl)-4-((4S,7S,10S,13S)-10-benzyl-7-isobutyl-15-methyl-13-((R)-2-methyl-oxirane-2-carbonyl)-2,5,8,11-tetraoxo-4-phenethyl-3,6,9,12-tetraazahexadecyl)morpholin-4-ium Methanesulfonate (9)
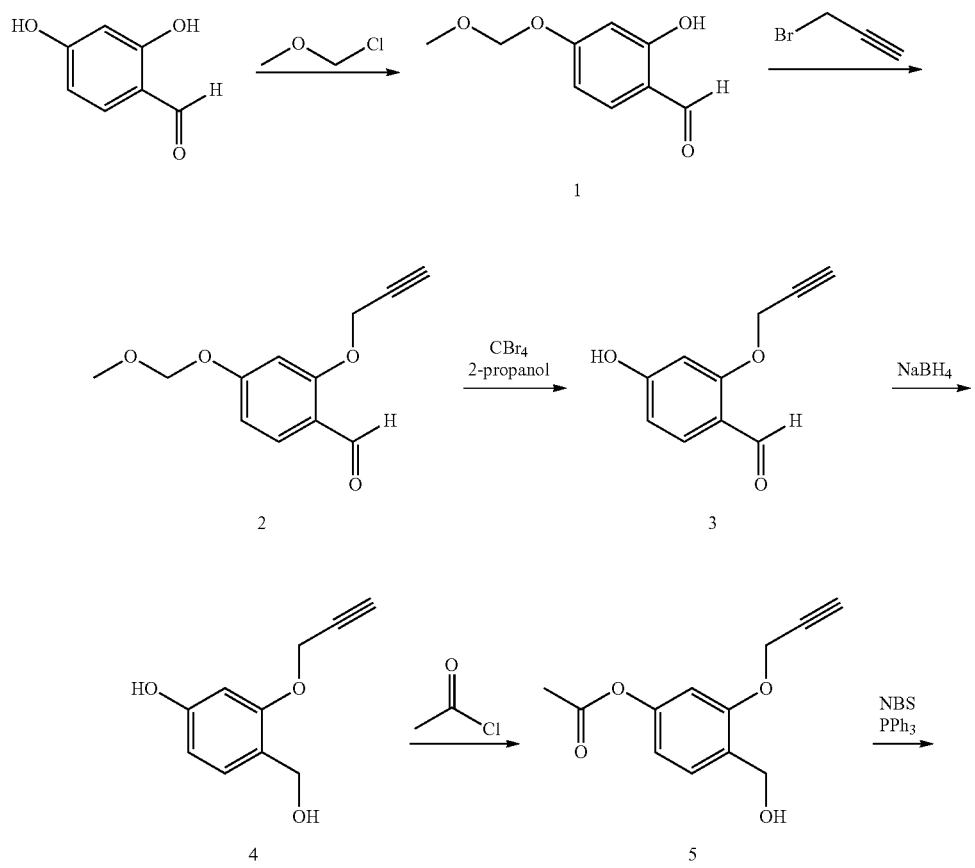

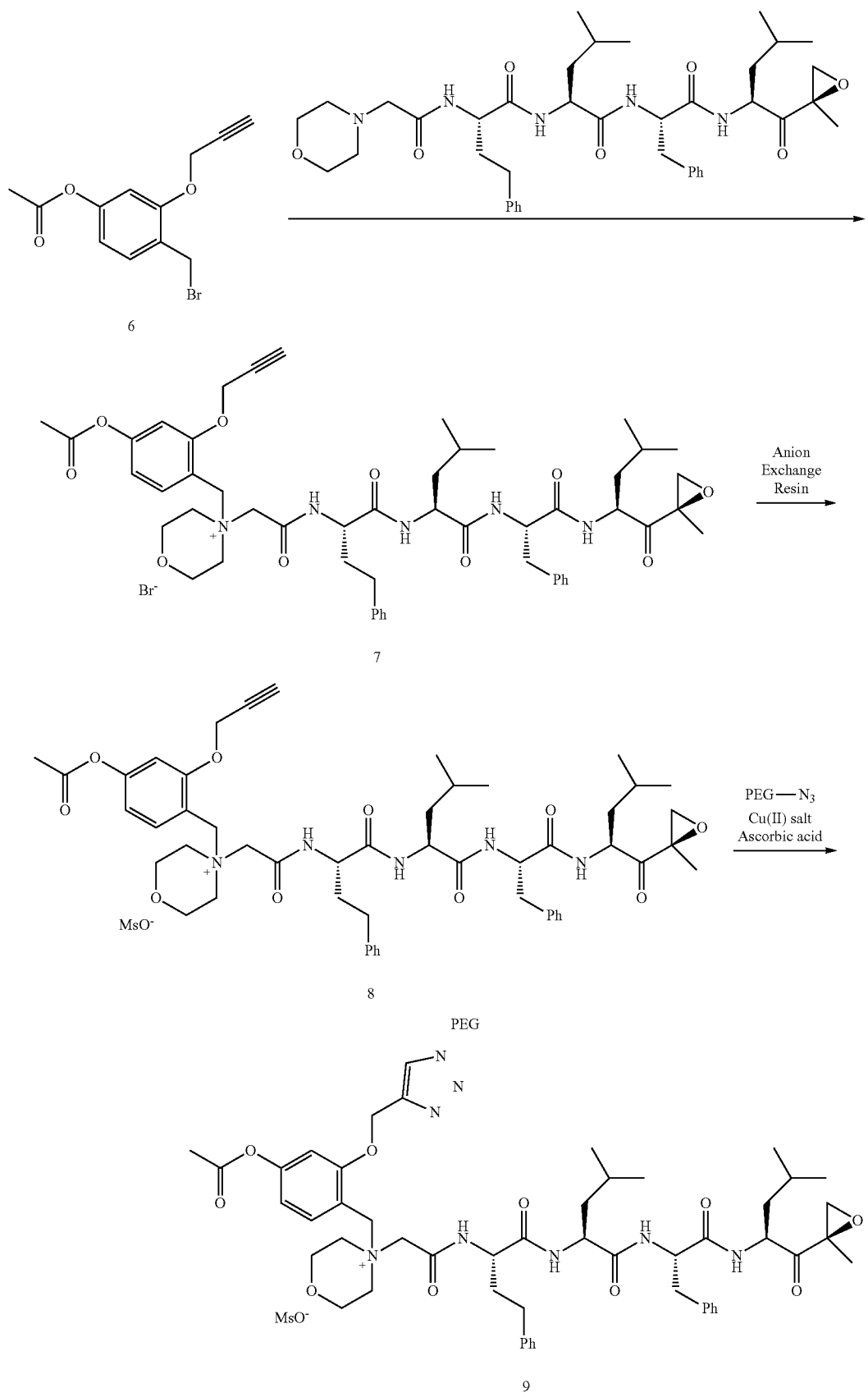

2-Hydroxy-4-(methoxymethoxy)benzaldehyde (1)

To a solution of compound 2,4-dihydroxybenzaldehyde (5.04 g, 36.24 mmol) in THF (100 mL) were added DIPEA (6.52 g, 54.35 mmol) and chloro(methoxy)methane (3.21 g, 39.86 mmol). The reaction mixture was stirred at RT overnight. An excess of solvent was concentrated and the residue was purified by flash column chromatography on silica gel (Petroleum Ether/EtOAc=15:1) to afford compound 1 (3.96 g, 60% yield); $^1$H NMR (300 MHz, CDCl$_3$): δ 11.41 (s, 1H), 9.76 (s, 1H), 7.48 (dd, J1=2.7 Hz, J2=8.4 Hz, 1H), 6.67 (dd, J1=2.4 Hz, J2=8.7 Hz, 1H), 6.62 (d, J=2.1 Hz, 1H), 5.25 (d, J=2.7 Hz, 2H), 3.51 (d, J=3.0 Hz, 3H).

4-(Methoxymethoxy)-2-(prop-2-ynyloxy)benzaldehyde (2)

To a mixture of NaH (900 mg, 21.252 mmol) in DMSO (100 mL) was added compound 1 (2.0 g, 10.63 mmol) in DMSO (50 mL) at 20° C. The mixture was stirred at the same temperature for 30 min and then 3-bromoprop-1-yne (1.90 g, 15.94 mmol) was added dropwise. The reaction mixture was stirred at the same temperature for 4 hours and then was poured into ice water (100 mL). The resulting solution was adjusted to pH=2-3 and EtOAc (100 mL) was added. The two phases were separated and the water phase was extracted with EtOAc (100 mL×3). The organic combined organic phases were dried and concentrated. The residue was purified by flash column chromatography on silica gel (Petroleum Ether/EtOAc=3:1) to afford compound 2 (1.89 g, 80% yield); $^1$H NMR (300 MHz, CDCl$_3$): δ 10.34 (s, 1H), 7.85 (d, J=9.3 Hz, 1H), 6.76 (m, 2H), 5.26 (s, 2H), 4.83 (d, J=2.4 Hz, 2H), 3.52 (s, 3H), 2.60 (q, J=2.4 Hz, 1H).

4-Hydroxy-2-(prop-2-ynyloxy)benzaldehyde (3)

To a solution of compound 2 (5.1 g, 23.18 mmol) in propan-2-ol (100 mL) was added CBr$_4$ (760 mg, 2.32 mmol). The reaction mixture was refluxed overnight. An excess of solvent was concentrated and the residue was purified by flash column chromatography on silica gel (Petroleum Ether/EtOAc=3:1) to afford compound 3 (2.44 g, 60% yield); $^1$H NMR (400 MHz, DMSO-d6): δ 10.76 (s, 1H), 10.11 (s, 1H), 7.60 (d, J=8.8 Hz, 1H), 6.59 (d, J=2.0 Hz, 1H), 6.52 (dd, J1=2.0 Hz, J2=8.8 Hz, 1H), 4.92 (d, J=2.4 Hz, 2H), 3.70 (q, J=2.4 Hz, 1H).

4-(Hydroxymethyl)-3-(prop-2-ynyloxy)phenol (4)

To a solution of compound 3 (2.45 g, 13.92 mmol) in MeOH (40 mL) was added NaBH$_4$ (618 mg, 16.698 mmol) in small portions at 0° C. The reaction mixture was stirred at the same temperature for 1 hour and then quenched with water (1.5 mL). An excess of solvent was concentrated and the residue was re-dissolved in EtOAc (100 mL). The resulting solution was dried and concentrated to afford compound 4 (1.80 g, 74% yield), which was used in the next step without further purification; $^1$H NMR (400 MHz, DMSO-d6): δ 6.98 (d, J=8.0 Hz, 1H), 6.32 (s, 1H), 6.26 (d, J=8.0 Hz, 1H), 4.65 (d, J=2.0 Hz, 2H), 4.32 (s, 2H), 3.54 (m, 1H).

4-(Hydroxymethyl)-3-(prop-2-ynyloxy)phenyl Acetate (5)

To a solution of compound 4 (1.20 g, 6.74 mmol) in DCM (30 mL) was added TEA (1.70 g, 16.85 mmol) followed by acetyl chloride (634 mg, 8 mmol) dropwise at 0° C. The reaction mixture was stirred at RT for 30 min. An excess of solvent was concentrated and the residue was purified by flash column chromatography on silica gel (Petroleum Ether/EtOAc=5:1) to afford compound 5 (360 mg, 30% yield); $^1$H NMR (400 MHz, DMSO-d6): δ 7.38 (d, J=8.0 Hz, 1H), 6.79 (d, J=2.0 Hz, 1H), 6.75 (dd, J1=2.0 Hz, J2=8.0 Hz, 1H), 5.09 (m, J=5.6 Hz, 1H), 4.82 (d, J=2.4 Hz, 1H), 4.46 (d, J=5.6 HZ, 2H), 3.60 (q, J=2.4 Hz, 1H), 2.26 (s, 3H).

4-(Bromomethyl)-3-(prop-2-ynyloxy)phenyl Acetate (6)

To a solution of compound 5 (360 mg, 1.64 mmol) in DCM (15 mL) was added PPh$_3$ (515 mg, 1.96 mmol) followed by NBS (318 mg, 1.80 mmol) in small portions at 0° C. The reaction mixture was stirred at the same temperature for 30 min. An excess of solvent was concentrated and the residue was purified by flash column chromatography on silica gel (Petroleum Ether/EtOAc=50:1) to afford compound 6 (190 mg, 41% yield); $^1$H NMR (400 MHz, CDCl3): δ 7.36 (d, J=8.4 Hz, 1H), 6.78 (d, J=2.0 Hz, 1H), 6.73 (dd, J1=2.0 Hz, J2=8.4 Hz, 1H), 4.77 (d, J=2.4 Hz, 2H), 4.54 (s, 2H), 2.56 (q, J=2.4 Hz, 1H), 2.31 (s, 3H).

4-(4-Acetoxy-2-(prop-2-yn-1-yloxy)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium Methanesulfonate (8)

To a solution of compound 6 (190 mg, 0.67 mmol) in MeCN (10 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (480 mg, 0.67 mmol). The reaction mixture was stirred at 45° C. overnight. An excess of solvent was concentrated and the residue was purified by flash column chromatography on silica gel (MeOH/EtOAc=1:50) to afford desired compound 7, which was transformed into the corresponding mesylate (340 mg, 74% yield) by treatment with ion exchange resin; $^1$H NMR (400 MHz, CDCl$_3$): δ 9.68 (m, 1H), 7.88 (m, 1H), 7.63 (m, 1H), 7.33-7.16 (m, 10H), 6.89 (m, 3H), 6.50 (m, 1H), 5.16 (m, 1H), 5.05 (m, 1H), 4.87 (m, 1H), 4.75 (m, 2H), 4.47 (m, 2H), 4.45-4.12 (m, 8H), 4.02 (m, 3H), 3.72 (m, 1H), 3.54 (m, 1H), 3.38 (m, 1H), 3.20 (m, 1H), 3.06 (m, 2H), 2.80 (s, 3H), 2.74 (m, 2H), 2.63 (m, 2H), 2.40-2.08 (m, 5H), 1.64 (m, 2H), 1.47 (s, 3H), 0.85 (m, 12H).

The compound of Example 2 was prepared from compound 8 and PEG$_{5K}$N$_3$ following general pegylation procedure A Example 13: 4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(3-((1-(PEG$_{20K}$-4-Arm)-1H-1,2,3-triazol-4-yl)methoxy)-4-(pivaloyloxy)benzyl) morpholin-4-ium Formate (7)
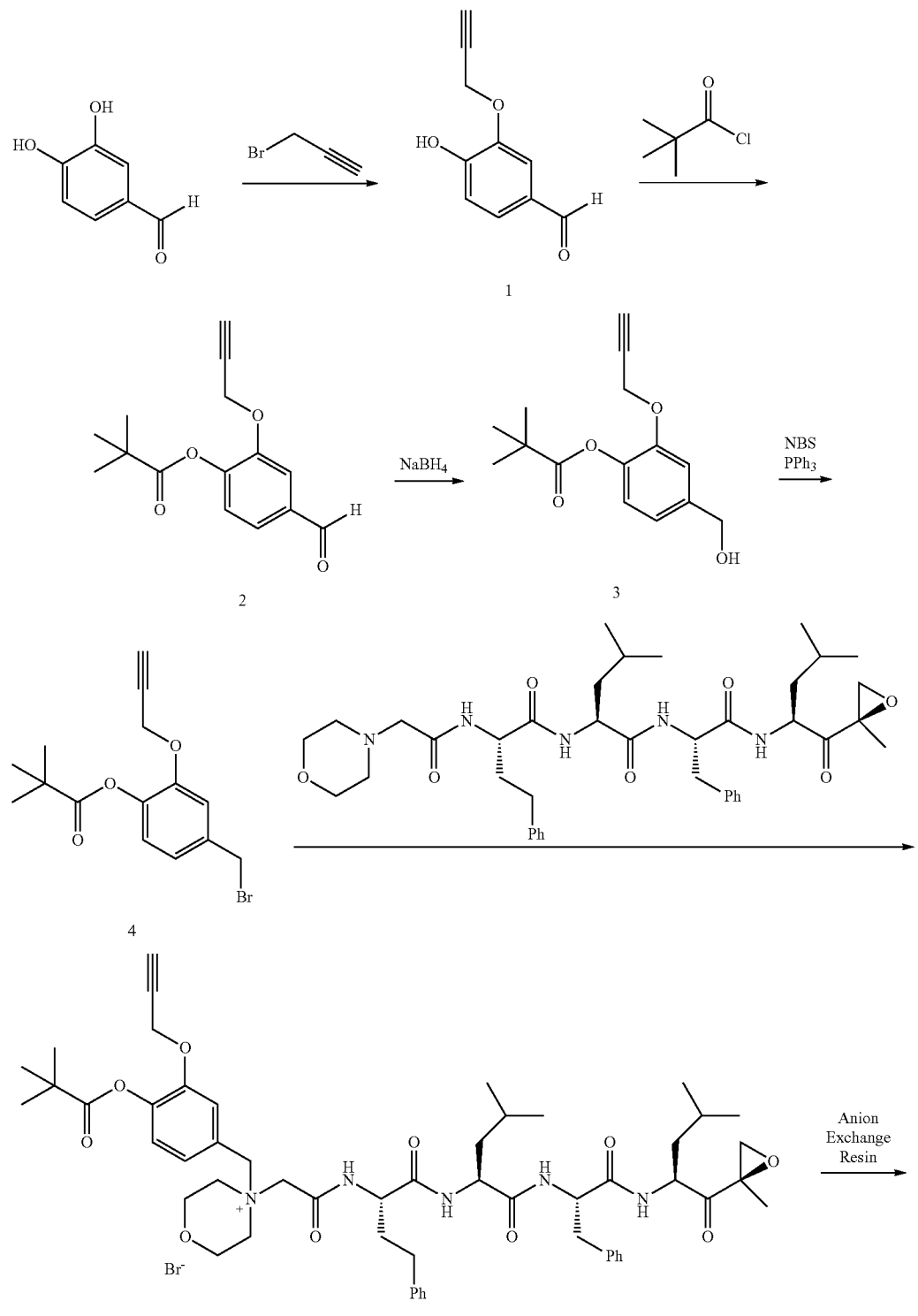

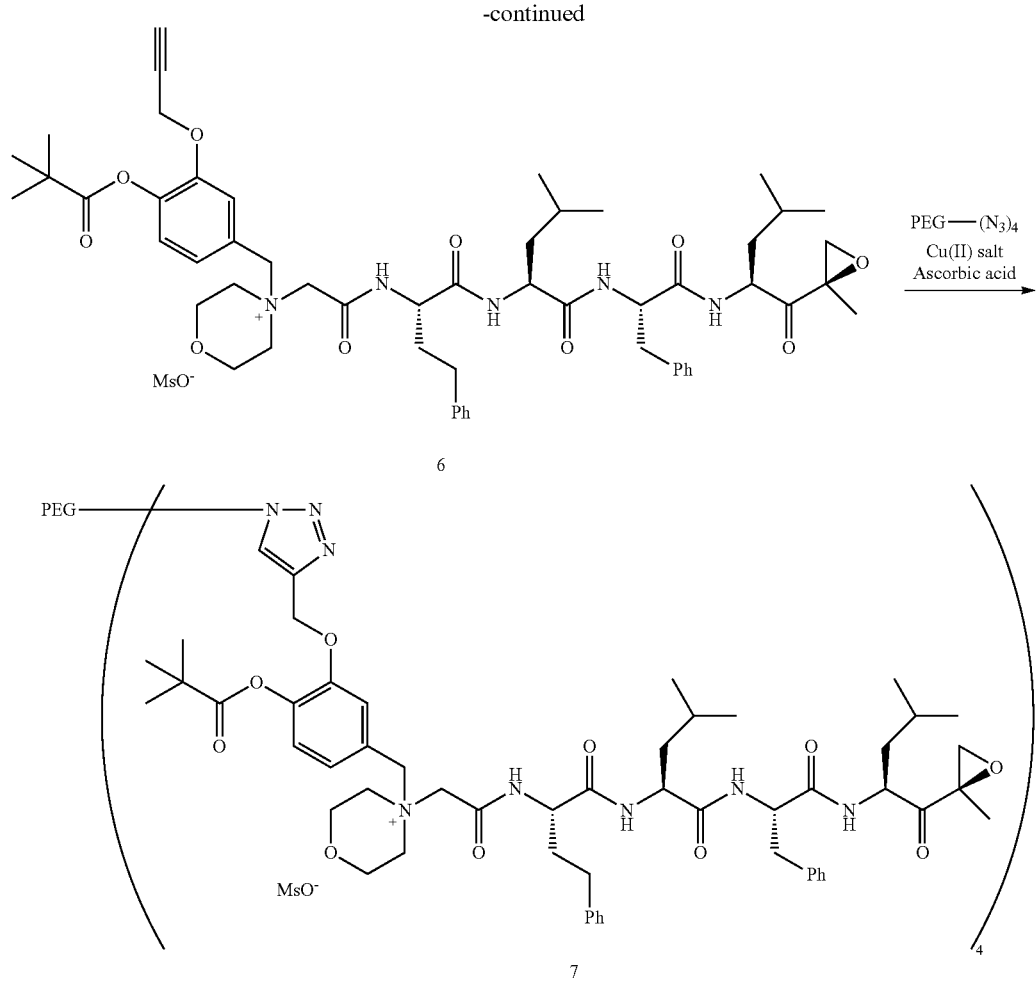

4-Hydroxy-3-(prop-2-ynyloxy)benzaldehyde (1)

To a mixture of NaH in DMSO (300 mL) was added 3,4-dihydroxybenzaldehyde (30 g, 217.39 mmol) in DMSO (50 mL) at 20° C. The mixture was stirred for 30 min and 3-bromoprop-1-yne (25.87 g, 217.39 mmol) was added. The reaction mixture was stirred at RT for one hour and then poured into ice water. The resulting solution was adjusted to pH=2 and then extracted with EtOAc (500 mL×3). The combined organic phases were dried over anhydrous $MgSO_4$ and concentrated. The residue was repeatedly crystallized from DCM/Petroleum Ether (30 mL/500 mL) to afford compound 1 (30 g, 78% yield); $^1H$ NMR ($CDCl_3$, 300 MHz): β 9.89 (s, 1H), 7.54 (d, J=1.2 Hz, 1H), 7.49 (dd, $J_1$=1.5 Hz, $J_2$=8.1 Hz, 1H), 7.09 (d, J=8.1 Hz, 1H), 4.82 (m, 2H), 2.62 (m, 1H).

4-Formyl-2-(prop-2-ynyloxy)phenylpivalate (2)

To a solution of compound 1 (3.0 g, 17 mmol) in DCM (120 mL) was added $Et_3N$ (3.45 g, 34 mmol) followed by pivaloyl chloride (2.34 g, 20.4 mmol) at 0° C. The reaction mixture was stirred at RT for 2 hours. The mixture was washed with saturated $NaHCO_3$ (20 mL) and water (20 mL), dried over anhydrous $MgSO_4$, and concentrated. The residue was purified by flash column chromatography on silica gel (Petroleum Ether/EtOAc=50:1) to afford compound 2 (2.10 g, 47% yield) as a white solid; $^1H$ NMR ($CDCl_3$, 300 MHz): δ 9.99 (s, 1H), 7.61 (d, J=1.8 Hz, 1H), 7.55 (dd, $J_1$=1.8 Hz, $J_2$=8.1 Hz, 1H), 7.26 (d, J=8.1 Hz, 1H), 4.77 (d, J=2.4 Hz, 2H), 2.58 (t, J=2.4 Hz, 1H), 1.42 (s, 9H).

4-(Hydroxymethyl)-2-(prop-2-ynyloxy)phenylpivalate (3)

To a solution of compound 2 (1.8 g, 6.9 mmol) in DCM/MeOH (100 mL/10 mL) was added $NaBH_4$ (0.37 g, 10.4 mmol) at 0° C. The reaction mixture was stirred at RT for 30 min. The mixture was quenched by acetone (3 mL) and the solvent was concentrated. The residue was purified by flash column chromatography on silica gel (Petroleum Ether/EtOAc=3:1) to afford compound 3 (1.50 g, 83% yield); $^1H$ NMR ($CDCl_3$, 300 MHz): δ 7.11 (m, 1H), 7.00 (m, 2H), 4.68 (m, 4H), 2.53 (m, 1H), 1.41 (s, 9H).

4-(Bromomethyl)-2-(prop-2-ynyloxy)phenylpivalate (4)

To a solution of compound 3 (1.50 g, 5.7 mmol) in DCM (60 mL) were added $PPh_3$ (1.80 g, 6.8 mmo) and NBS (1.11 g, 6.3 mmol) at 0° C. The reaction mixture was stirred at RT for 0.5 hour. An excess of solvent was concentrated and the residue was purified by flash column chromatography on silica gel (Petroleum Ether/EtOAc=50:1) to afford compound 4 (1.34 g, 81% yield); ¹H NMR (CDCl₃, 300 MHz): δ 7.12 (d, J=1.5 Hz, 1H), 7.03 (m, 2H), 4.70 (d, J=2.4 Hz, 2H), 4.51 (d, J=3.9 Hz, 2H), 2.56 (t, J=2.4 Hz, 1H), 1.40 (s, 9H).

4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(4-(pivaloyloxy)-3-(prop-2-yn-1-yloxy)benzyl)morpholin-4-ium methanesulfonate (6)

To a solution of compound 4 (2.38 g, 7.3 mmol) in MeCN (30 ml) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (2.64 g, 3.7 mmol). The reaction mixture was stirred at 45° C. overnight. An excess of solvent was concentrated and the residue was purified by flash column chromatography on silica gel (EtOAc/MeOH=100:6) to afford desired compound 5, which was transformed into the corresponding mesylate (1.23 g, 25% yield) by treatment with ion exchange resin; ¹H NMR (CDCl₃, 300 MHz): δ 9.83 (m, 1H), 7.92 (m, 1H), 7.50-7.11 (m, 13H), 7.03 (m, 1H), 6.62 (m, 1H), 5.25 (m, 1H), 5.15-4.90 (m, 2H), 4.88-4.75 (m, 2H), 4.70-4.20 (m, 7H), 4.20-3.90 (m, 3H), 3.70-3.40 (m, 4H), 3.26 (m, 1H), 3.15 (m, 2H), 2.90 (s, 3H), 2.85 (m, 2H), 2.40-2.10 (m, 2H), 1.87-1.63 (m, 5H), 1.55 (m, 3H), 1.41 (s, 9H), 1.38 (m, 2H), 0.89-1.05 (m, 12H).

Compound Example 13 was prepared from compound 6 and PEG₂₀ₖ(N₃)₄ following general pegylation procedure A. Compound Example 13 is also designated as OP-59381 in various of the figures illustrated herein. ¹H NMR (500 MHz, relaxation time=10 sec, DMSO-d₆) δ 8.47 (s, 4H), 8.42 (d, J=8.5 Hz, 4H), 8.29 (d, J=7.5 Hz, 4H), 8.11 (s, 4H), 8.07 (d, J=8 Hz, 4H), 7.53 (s, 4H), 7.26-7.29 (m, 4H), 7.11-7.19 (m, 32H), 7.05-7.06 (m, 4H), 5.21 (s, 8H), 4.95 (dd, J=12.5 Hz and 39.0 Hz, 8H), 4.52-4.54 (m, 12H), 4.28-4.38 (m, 16H), 4.17-4.20 (m, 4H), 4.06 (m, 20H), 3.78 (t, J=5.5 Hz, 8H), 3.61-3.65 (m, 8H), 3.50 (s, 2133H), 3.35-3.37 (m, 8H), 3.10 (d, J=5 Hz, 4H), 2.94-2.98 (m, 12H), 2.73-2.78 (m, 4H), 2.50-2.65 (m, 8H), 1.90-1.98 (m, 4H), 1.78-1.88 (m, 4H), 1.51-1.68 (m, 8H), 1.39 (s, 12H), 1.25-1.38 (m, 16H), 1.18 (s, 36H), 0.833-0.881 (m, 24H), 0.782-0.815 (m, 24H); Loading: 86%.

Example 18: 4-(3-Acetoxy-4-((PEG₅ₖ-imino)methyl)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium Methanesulfonate (8)

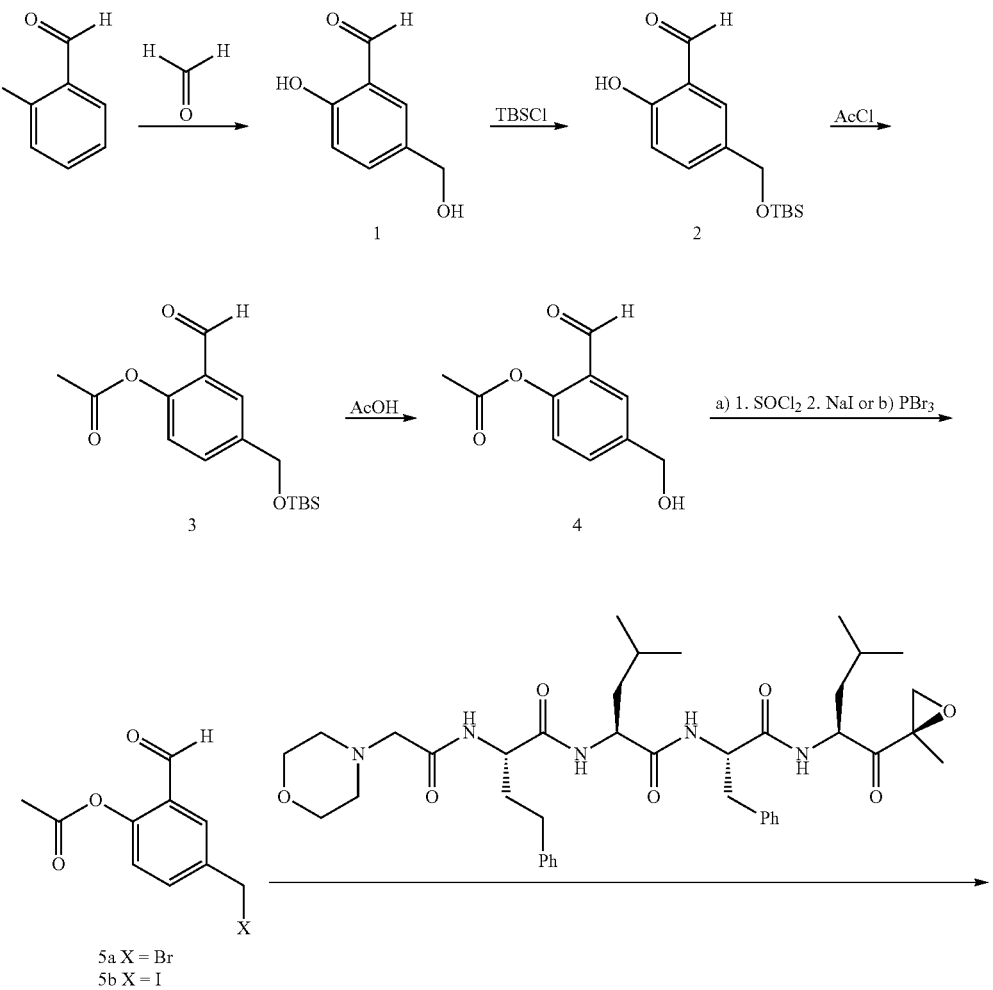

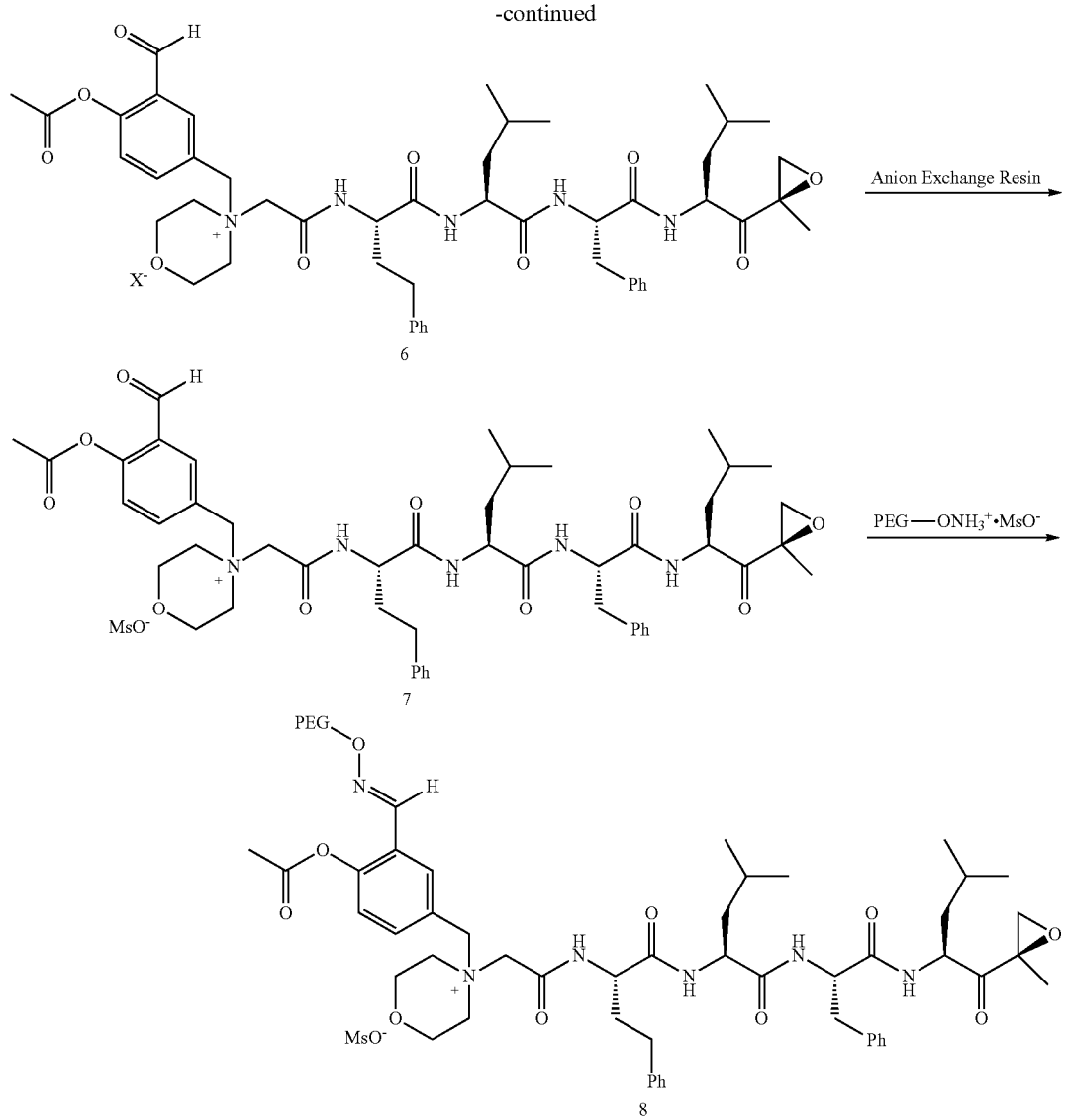

2-Hydroxy-5-(hydroxymethyl)benzaldehyde (1)

To an aqueous solution of formaldehyde (37%, 17 mL) were added 2-hydroxybenzaldehyde (10.3 g, 84.4 mmol) and concentrated HCl (42 mL). The reaction mixture was heated under reflux overnight. The mixture was cooled to RT and then extracted with EtOAc (200 mL). The organic phase was dried over anhydrous sodium sulfate and concentrated. The residue was purified by flash column chromatography on silica gel (Petroleum Ether/EtOAc=3:1) to afford compound 1 (1.97 g, 15% yield); $^1$H NMR (DMSO-$d_6$, 300 MHz): δ 10.61 (s, 1H), 10.26 (s, 1H), 7.60 (d, J=2.1 Hz, 1H), 7.46 (dd, J=2.4, 8.7 Hz, 1H), 6.96 (d, J=8.4 Hz, 1H), 5.18 (m, 1H), 4.42 (d, J=3.3 Hz, 2H).

5-(((tert-Butyldimethylsilyl)oxy)methyl)-2-hydroxybenzaldehyde (2)

To a solution of compound 1 (2.01 g, 13.2 mmol) in DCM (60 mL) was added imidazole (1.43 g, 21 mmol). The solution was cooled to 0° C. and tert-butylchloro dimethylsilane (2.57 g, 17.1 mmol) was added. The reaction mixture was stirred at RT for 3 h and then poured into water (50 mL). The two phases were separated and the organic phase was dried over anhydrous sodium sulfate and concentrated. The residue was purified by flash column chromatography on silica gel (Petroleum Ether/EtOAc=50:1) to afford compound 2 (3.2 g, 91% yield); $^1$H NMR (CDCl$_3$, 400 MHz): δ 10.85 (br, s, 1H), 9.78 (s, 1H), 7.41 (d, J=2.0 Hz, 1H), 7.35 (dd, J=2.0, 8.4 Hz, 1H), 6.85 (d, J=8.4 Hz, 1H), 4.59 (s, 2H), 0.82 (s, 9H), 0.00 (s, 6H).

4-((tert-Butyldimethylsilyloxy)methyl)-2-formylphenyl Acetate (3)

To a solution of compound 2 (25 g, 94 mmol) in DCM (500 mL) was added TEA (19.0 g, 188 mmol). The mixture was cooled to 0° C. and acetyl chloride (11.1 g, 141 mmol) was added. The reaction mixture was stirred at room temperature for 2 h. The mixture was washed with water (500 mL). The organic phase was dried over anhydrous sodium sulfate and concentrated. The residue was purified by flash column chromatography on silica gel (Petroleum Ether/EtOAc=100:1) to afford compound 3 (19.7 g, 68% yield); $^1$H NMR (CDCl$_3$, 400 MHz): δ 9.98 (s, 1H), 7.70 (d, J=2.0 Hz, 1H), 7.49 (dd, J=2.4, 8.4 Hz, 1H), 7.03 (d, J=2.4 Hz, 1H), 4.66 (s, 2H), 2.28 (s, 3H), 0.83 (s, 9H), 0.00 (s, 6H).

2-Formyl-4-(hydroxymethyl)phenyl Acetate (4)

Compound 3 (3.6 g, 11.7 mmol) was dissolved in AcOH/THF/H$_2$O (50 mL/25 mL/25 mL). The reaction mixture was stirred at 30° C. for 3 h. An excess of THF was removed and the resulting solution was adjusted to pH=7-8 and then extracted with EtOAc (50 mL×3). The combined organic phases were dried over anhydrous sodium sulfate and concentrated. The residue was purified by flash column chromatography on silica gel (Petroleum Ether/EtOAc=3:1) to afford compound 4 (2.04 g, 90% yield); $^1$H NMR (DMSO-d$_6$, 400 MHz): δ 10.08 (s, 1H), 7.85 (d, J=2.0 Hz, 1H), 7.67 (dd, J=2.4, 8.4 Hz, 1H), 7.26 (d, J=8.4 Hz, 1H), 4.57 (s, 2H), 2.35 (s, 3H).

4-(Bromomethyl)-2-formylphenyl Acetate (5a)

To a solution of compound 4 (2.03 g, 10.3 mmol) in DCM (80 mL) was added PBr$_3$ (2.79 g, 10.3 mmol) at 0° C. The reaction mixture was stirred at RT for 4 h. The reaction was quenched by addition of water (20 mL) and the resulting mixture was adjusted to pH=7 with saturated aqueous NaHCO$_3$. The organic phase was separated, dried over anhydrous sodium sulfate and concentrated. The residue was purified by flash column chromatography on silica gel (Petroleum Ether/EtOAc=3:1) to afford compound 5a (300 mg, 11% yield); $^1$H NMR (CDCl$_3$, 300 MHz): δ 10.12 (s, 1H), 7.92 (d, J=2.1 Hz, 1H), 7.68 (dd, J=2.4, 8.4 Hz, 1H), 7.22 (d, J=8.1 Hz, 1H), 4.54 (s, 2H), 2.42 (s, 3H).

4-(Iodomethyl)-2-formylphenyl Acetate (5b)

To a solution of compound 4 (5.0 g, 27.55 mmol) in DCM (300 mL) was added SOCl$_2$ (6.13 g, 51.55 mmol) at 0° C. The reaction mixture was heated under reflux overnight. The mixture was concentrated and the residue was purified by flash column chromatography on silica gel (Petroleum Ether/EtOAc=10:1) to afford the corresponding benzyl chloride (2.4 g, 44% yield); $^1$H NMR (CDCl$_3$, 300 MHz): δ 10.12 (s, 1H), 7.92 (d, J=2.4 Hz, 1H), 7.68 (dd, J=2.4, 8.4 Hz, 1H), 7.22 (d, J=2.4 Hz, 1H), 4.64 (s, 2H), 2.42 (s, 3H).

To a solution of benzyl chloride (2.4 g, 11.29 mmol) in acetone (160 mL) was added NaI (16.94 g, 112.94 mmol). The reaction mixture was stirred at 30° C. overnight. The mixture was concentrated and the residue was dissolved in DCM (100 mL). The resulting solution was washed with saturated aqueous Na$_2$S$_2$O$_3$ (50 mL×3) and water (50 mL), dried over anhydrous sodium sulfate and concentrated to afford compound 5b (2.1 g, 61% yield), which was used in the next step without further purification. $^1$H NMR (CDCl$_3$, 300 MHz): δ 10.10 (s, 1H), 7.90 (d, J=2.4 Hz, 1H), 7.66 (dd, J=2.1, 8.4 Hz, 1H), 7.16 (d, J=2.4 Hz, 1H), 4.49 (s, 2H), 2.41 (s, 3H).

4-(4-Acetoxy-3-formylbenzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium Methanesulfonate (7)

To a solution of compound 5b (380 mg, 1.48 mmol) in MeCN (5 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (532 mg, 0.74 mmol). The reaction mixture was stirred at 45° C. overnight. The solvent was removed under reduced pressure. The residue was purified by flash column chromatography on silica gel (DCM/MeOH=10:1) to afford desired compound (6), which was then transformed into the corresponding mesylate by treatment with ion exchange resin (280 mg, 39% yield); $^1$H NMR (CDCl$_3$, 400 MHz): δ 10.15 (s, 1H), 9.53 (br s, 1H), 8.03 (d, J=2.0 Hz, 1H), 7.85 (m, 1H), 7.68 (br s, 1H), 7.37 (d, J=8.0 Hz, 1H), 7.26-7.13 (m, 10H), 6.84 (br s, 1H), 6.52 (br s, 1H), 5.20 (m, 2H), 4.97 (m, 1H), 4.50-3.96 (m, 7H), 3.46-3.28 (m, 2H), 3.16 (m, 1H), 3.06-2.92 (m, 3H), 2.85-2.61 (m, 7H), 2.44 (s, 3H), 2.14 (m, 2H), 1.69-1.17 (m, 11H), 0.89-0.83 (m, 12H). Compound 5a could also be used for this reaction.

Example 18 was prepared from compound 7 and PEG$_{5K}$ONH$_3^+$·MsO$^-$ following general pegylation procedure A.

Example 23: 4-(3-Acetoxy-4-((PEG$_{3K}$-imino)methyl)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium Methanesulfonate (8)

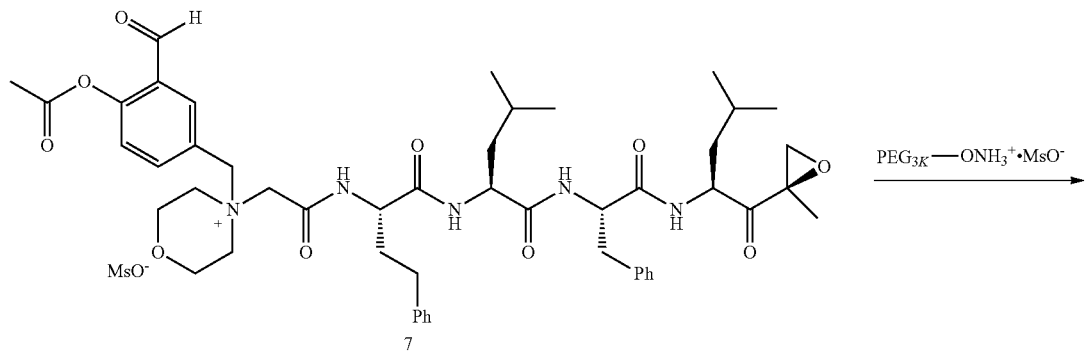

7

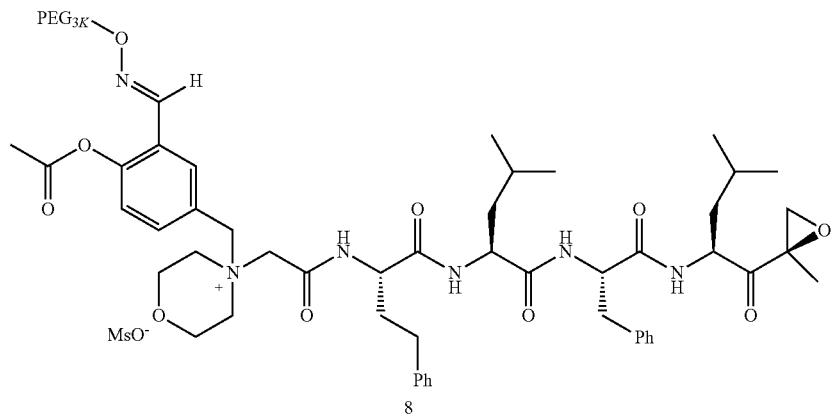

4-(4-Acetoxy-3-formylbenzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium Methanesulfonate (7)

To a solution of compound 5b (380 mg, 1.48 mmol) in MeCN (5 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (532 mg, 0.74 mmol). The reaction mixture was stirred at 45° C. overnight. The solvent was removed under reduced pressure. The residue was purified by flash column chromatography on silica gel (DCM/MeOH=10:1) to afford desired compound (6), which was then transformed into the corresponding mesylate by treatment with ion exchange resin (280 mg, 39% yield); $^1$H NMR (CDCl$_3$, 400 MHz): δ 10.15 (s, 1H), 9.53 (br s, 1H), 8.03 (d, J=2.0 Hz, 1H), 7.85 (m, 1H), 7.68 (br s, 1H), 7.37 (d, J=8.0 Hz, 1H), 7.26-7.13 (m, 10H), 6.84 (br s, 1H), 6.52 (br s, 1H), 5.20 (m, 2H), 4.97 (m, 1H), 4.50-3.96 (m, 7H), 3.46-3.28 (m, 2H), 3.16 (m, 1H), 3.06-2.92 (m, 3H), 2.85-2.61 (m, 7H), 2.44 (s, 3H), 2.14 (m, 2H), 1.69-1.17 (m, 1 1H), 0.89-0.83 (m, 12H).

Example 23 was prepared by methods analogous to those described in Example 16, wherein the intermediates were made in similar fashion (using acetyl chloride to generate the corollary intermediate 1 shown in eg 16 and compound 7 in International application no. PCT/US2017/03429) and PEG$_{3K}$ONH$_3^+$·MsO$^-$ following general pegylation procedure A.

Example 26: 4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(4-(isobutyryloxy)-3-((PEG$_{5K}$-imino)methyl)benzyl)morpholin-4-ium Methanesulfonate (6)

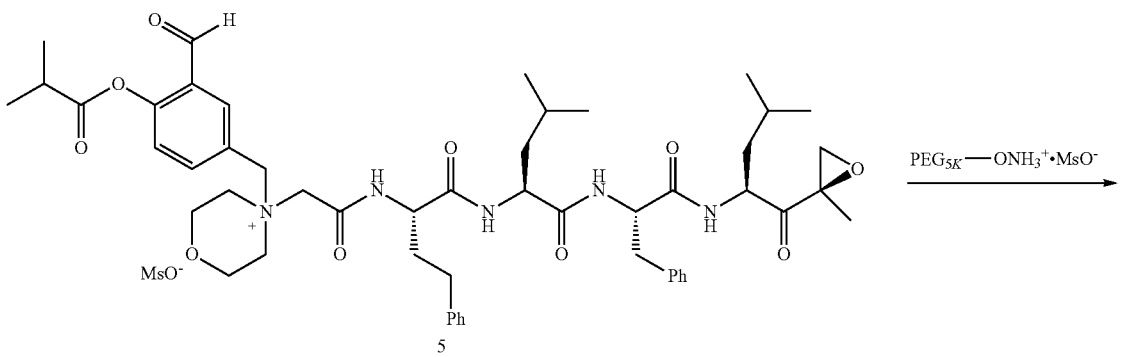

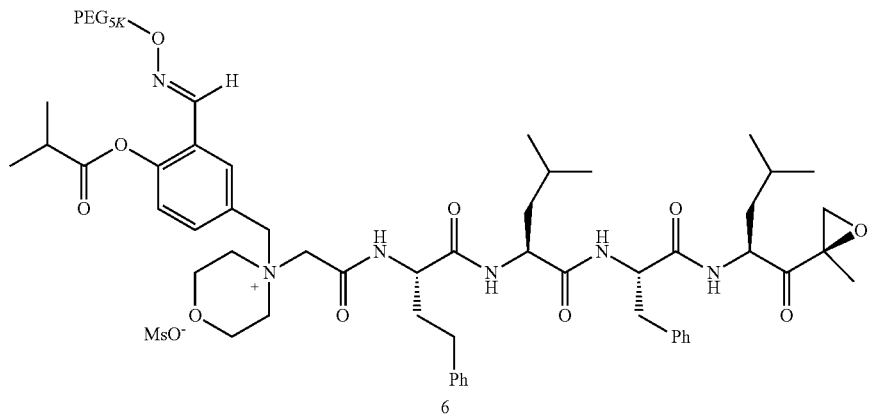

6

4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(3-formyl-4-(isobutyryloxy)benzyl)morpholin-4-ium Methanesulfonate (5)

To a solution of compound 3 (550 mg, 1.657 mmol) in MeCN (8 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (393 mg, 0.547 mmol). The reaction mixture was stirred at 40° C. overnight. An excess of solvent was concentrated and the residue was crystallized repeatedly from (EtOAc/Et$_2$O=1:5) to afford the desired compound 4, which was transformed into the corresponding mesylate 5 (115 mg, 7.5% yield) by treatment with ion exchange resin; $^1$H NMR (400 MHz, CDCl$_3$): δ 10.18 (s, 1H), 9.68 (m, 1H), 8.04 (m, 1H), 7.89 (m, 1H), 7.81 (s, 1H), 7.35 (m, 1H), 7.30 (m, 1H), 7.11-7.29 (m, 9H), 6.79 (s, 1H), 6.44 (m, 1H), 5.18 (m, 2H), 4.99 (m, 1H), 4.41 (m, 3H), 4.20 (m, 3H), 3.99 (m, 3H), 3.40 (m, 1H), 3.30 (m, 1H), 3.20 (m, 1H), 2.95 (m, 2H), 2.92 (m, 1H), 2.79 (m, 3H), 2.75 (m, 2H), 2.21 (m, 1H), 2.09 (m, 1H), 1.83 (m, 4H), 1.62 (m, 2H), 1.49 (m, 4H), 1.38 (m, 6H), 1.24 (m, 2H), 0.88 (m, 12H).

Example 26 was prepared by methods analogous to those described in Example 16, wherein the intermediates were made in similar fashion (using isopropanoyl chloride to generate the corollary intermediate 1 shown in eg 16, and compound 5 (in International application no. PCT/US2017/03429)) and PEG$_{5K}$ONH$_3^+$.MsO$^-$ following general pegylation procedure B.

Example 32: 4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(4-(isobutyryloxy)-3-((4-(PEG$_{5K}$-imino)methyl)benzyl)oxy)benzyl)morpholin-4-ium Methanesulfonate (8)

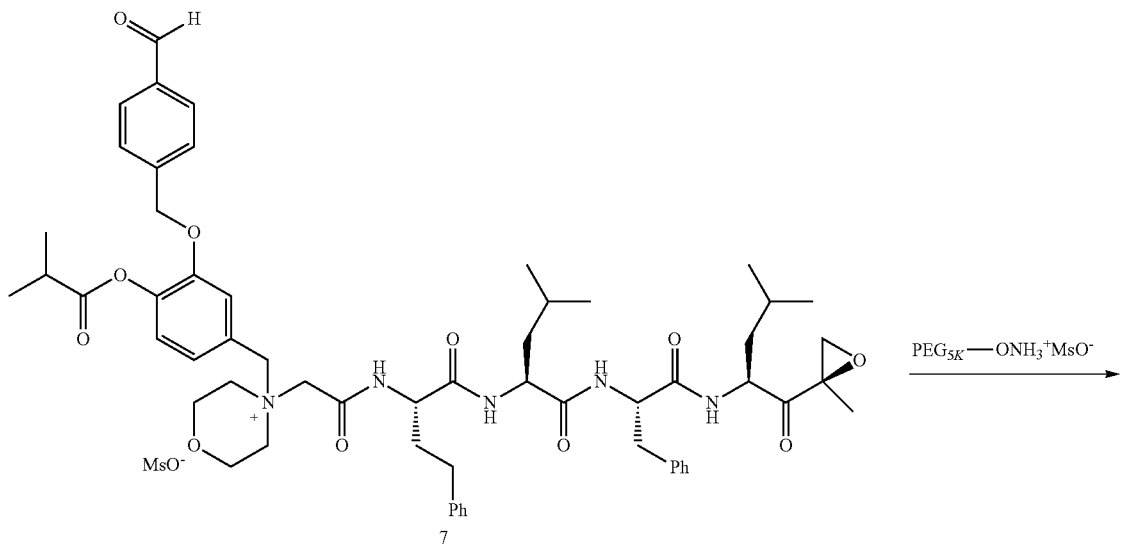

7

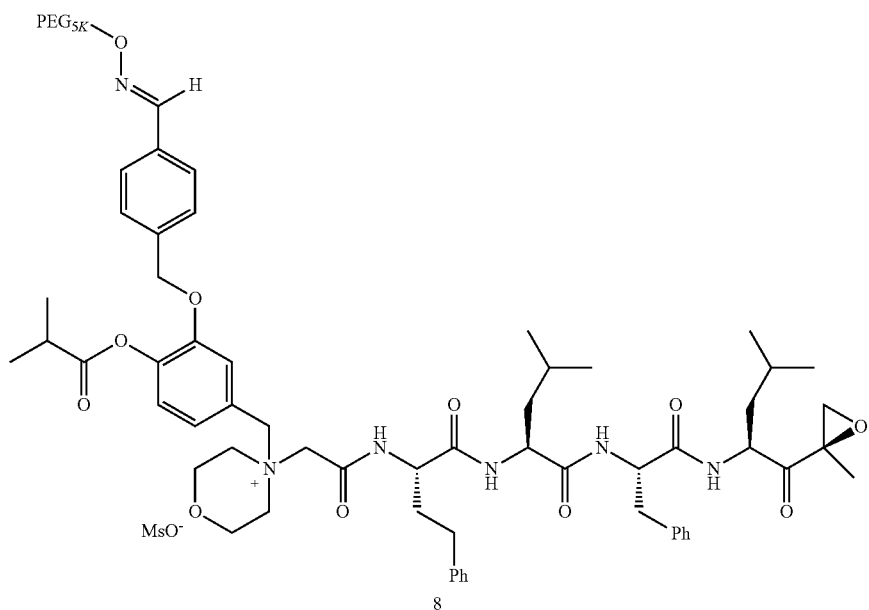

4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(3-(4-formylbenzyloxy)-4-(isobutyryloxy)benzyl)morpholin-4-ium Methanesulfonate (7)

To a solution of compound 5 (310.4 mg, 0.80 mmol) in MeCN (2 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (286 mg, 0.30 mmol). The reaction mixture was stirred at 45° C. for 48 hours. An excessive solvent was evaporated and the residue was repeatedly crystallized from MeCN/Et₂O (1/5, v/v) to afford the desired product 6, which was then transformed into the corresponding mesylate compound 7 (280 mg, 83% yield) by treatment with ion exchange resin.

A solution of compound 6 (280 mg, 0.25 mmol), 2-amino-5-methoxybenzoic acid (14.0 mg, 0.026 mmol) and PEG-O-NH₂ (mesylate salt, 1.16 g, 0.227 mmol) in DCM (3 mL) was stirred at r.t. for 2 h. The reaction mixture was then concentrated and the residue was dissolved in i-PrOH at 40° C. The solution was cooled to room temperature and Et₂O was added to induce crystallization. The mixture was kept in ice bath for 10 min and formed solid was collected by filtration. Crystallization from i-PrOH/Et₂O (5:2) was repeated twice until all 7 was removed to afford 8 (1.0 g, 72% yield).

Example 34: 4-(4-Acetoxy-3-((1-PEG₃ₖ-1H-1,2,3-triazol-4-yl)methoxy)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium Chloride

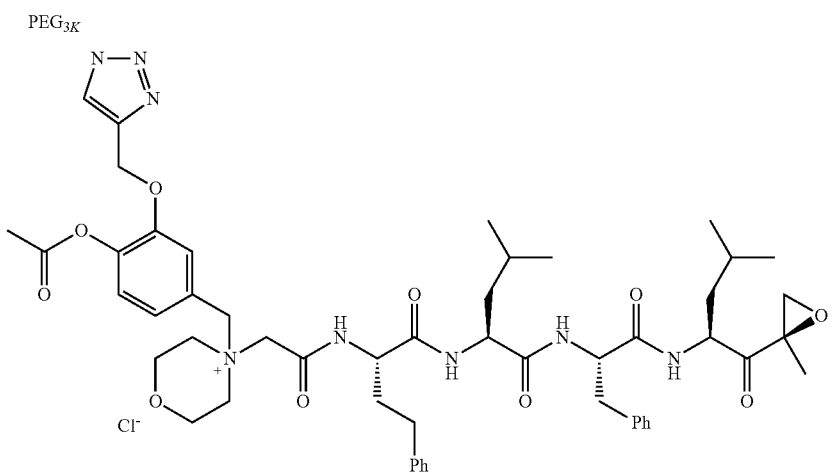

Example 34 was prepared using a method analogous to that taught in Examples 5-11 in International application no. PCT/US2017/03429 and Method A, but using the chloride salt intermediate having a chloride anion as the counter ion.

Example 35: 4-(4-Acetoxy-3-((1-PEG$_{3K}$-1H-1,2,3-triazol-4-yl)methoxy)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium Mesylate

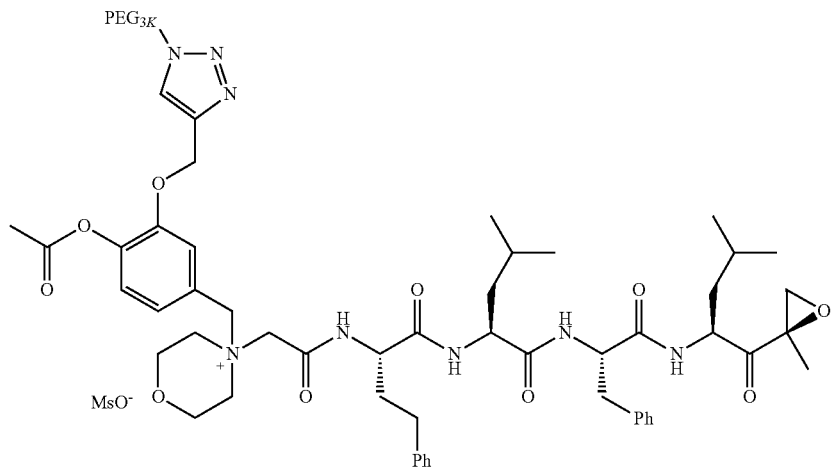

Example 35 was prepared using a method analogous to that taught in Examples 5-11 in International application no. PCT/US2017/03429 and Method A using a PEG$_{3K}$N$_3$. $^1$H NMR (DMSO-d6, 400 MHz): δ 9.19 (M, 1H), 8.24 (m, 2H), 8.12 (m, 1H), 7.90 (m, 1H), 7.62 (m, 1H), 7.22 (m, 13H), 7.0 (m, 1H), 5.26 (m, 2H), 4.88 (m, 2H), 4.53 (m, 3H), 4.37 (br s, 4H), 4.05 (m, 5H), 3.81 (m, 2H), 3.68 (m, 4H), 3.52 (br s, 339H), 3.30 (m, 4H), 3.24 (s, 4H), 2.94 (m, 2H), 2.75 (m, 1H), 2.63 (m, 2H), 2.24 (s, 3H), 1.87 (m, 2H), 1.59 (m, 2H), 1.40 (m, 7H), 0.84 (m, 12H)

The present invention provides pharmaceutical compositions comprising a pegylated carfilzomib compound of Formulas I or II, and an array of excipients and buffers from which to choose. The invention provides stable, isotonic frozen and dry lyophilized formulations, as described herein. These pharmaceutical compositions are useful for delivering biologically active pegylated carfilzomib compounds for the treatment of cancer. These compositions (also referred to herein as formulations) include, without limitation, stable formulations that may be administered by parenteral routes of administration, including administration intravenously and subcutaneously to a patient in need of treatment. The compositions are adequately stable as a liquid, for use in both clinical and commercial cancer settings.

The letter and numeric designations as used in the formulations described herein, are defined as follows:

"A" is for an acetate buffer system at the concentration noted;
"G" is for a glutamate buffer system at the concentration indicated;
"H" is for histidine;
"M" is for mannitol;
"T" is for Tris-HCl;
"Na" is for sodium chloride;
"Pro" is for proline;
"Gly" is for glycine;

The number 5, 6, 7 and 8 designates a pH for the formulation;
"Su" stands for sucrose followed by a number designating the % sucrose contained in the formation;

Thus, a formulation designated herein as "A5Su" means the formulation contains 10 mM Acetate, 9.0% Sucrose and has a pH of 5.0, in addition to the mg amount or mg/mL concentration of the active carfilzomib amount present in the pegylated carfilzomib API compound. Solutions made and tested herein were prepared by adding half of the desired water to a batch container and subsequently measuring out the amount of each component (i.e. acetate, sucrose, and excipient such as PS80) to reach the desired (or designated) concentration of each component. The exact concentrations/amounts were calculated using the molar mass of each component/chemical. The calculated amounts were added to the batch container; the resulting solution was stirred well until all components are mixed and dissolved. The initial pH of the solution was measured and the solution was titrated to the appropriate pH using 10N NaOH or 37% HCl stock solutions, depending upon desired/stated pH. The remaining volume of water needed to achieve the final concentration was added to the batch container and the final pH and temperature of the solution was taken. The solution was filtered aseptically through a 0.22 micron cellulose acetate filter into an appropriate sized container. Starting reagents are commercially available and were purchased from Sigma-Aldrich.

Some of the tests conducted herein involve measuring the osmolality of the representative formulation or solution. Freezing point depression osmolality measurements were collected using an Advanced Instruments 3250 Single Sample Osmometer. All samples were sterile filtered with 0.2 micron PES filters prior to measurement to insure no particulation. An average of three measurements were performed for each sample point. The instrument operation was verified with 100, 200 and 290 mOsm standards prior to sample data collection.

Carfilzomib (CFZ) is a marketed proteasome inhibitor under the brand name Kyprolis® and is indicated for the treatment of relapsed or refractory multiple myeloma. The current route of administration for Kyprolis is IV (intravenous). From a patient convenience point of view, a subcutaneous formulation would be highly desired to convert a 30-90 minute intravenous administration into a 5 min or less subcutaneous injection. One significant challenge in creating a subcutaneous formulation is the solubility of carfilzomib. The currently approved formulation is a dry lyophilized formulation, which when reconstituted with the proper amount of sterile water as instructed on the approved label, results in a clear administrable liquid solution having about 2 mg/mL concentration of carfilzomib in Captisol®. In order to increase solubility of carfilzomib in water, pegylated carfilzomib compounds have been discovered and made with varying lengths of PEG attached to it. The PEG group is attached to carfilzomib with covalently bound linkers that are designed to be cleaved once the PEG-CFZ construct is administered parenterally into the human body.

The following pegylated carfilzomib compounds were used in the experiments described herein illustrating the stability, longevity and clarity of the formulations of the present invention. Example 39 (OP-0059381) is carfilzomib with a 20kPEG attached to it; example 26 (OP-0214575) has a 5kPEG attached to it; and example 34 (OP-0214576-1) has a 3kPEG attached to it.

In order to identify stable formulations of PEG-CFZ, various formulations were made wherein the desired pegylated carfilzomib compound (API) was dissolve in experimental compositions of excipients, and the stability and quantity of the intact, non-degraded API was monitored and measured in the frozen state (−20° C. or below). Formulations of API was also prepared and tested to determine the ability of each exemplary formulation to provide adequate stability in the liquid state to be suitable for clinical and commercial administration. Here, these formulations were stored at least 8 hours at room temperature and 2 days at a temperatures ranging from 2-8° C. All formulations that were tested contained desired API compounds at 1 mg/mL concentrations.

For each formulation, the stability of the API was tested using three observable and/or measurable characteristics, as follows:
1. Integrity of the molecule, as assessed by the reverse phase assay;
2. Clarity of the solution, via visual assessment; and
3. Concentration of the API material in the solution, as assessed by material recovery after centrifugation Results Integrity of the API: The first study criteria focused on reducing or minimizing hydrolysis of the carfilzomib epoxide ring, as hydrolysis results in an inactive degradation by-product and impurity. Various exemplary formulations wherein the API (pegylated carfilzomib compound example 26) was dissolved in a solution as described in Table 2.

TABLE 2

| Formulation Designation | pH | Buffer system | Excipient(s) included |
|---|---|---|---|
| A5Su | 5 | 10 mM acetate | 9% sucrose |
| H6Su | 6 | 10 mM histidine | 9% sucrose |
| T7Su | 7 | 10 mM Tris-HCl | 9% sucrose |
| T8Su | 8 | 10 mM Tris-HCl | 9% sucrose |
| T7Na | 7 | 10 mM Tris-HCl | 140 mM sodium chloride |
| T7Pro | 7 | 10 mM Tris-HCl | 220 mM L-proline |
| T7Gly | 7 | 10 mM Tris-HCl | 293 mM glycine |
| T7NaSu | 7 | 10 mM Tris-HCl | 70 mM sodium chloride, 4.5% sucrose |

The pH range tested was 5-8 in appropriate buffers. The excipient sucrose was kept constant from pH 5 to 8 to more directly test the effect of varying pH from a slightly acidic pH to a slightly basic pH, at an isotonic level of 9%.

Another aspect of this study was to test the effect of an excipient at the same pH. For this purpose, in a constant composition of 10 mM Tris-HCl at pH 7, the following excipients were tested: sucrose (polyol), sodium chloride (salt), proline (representative amino acid), glycine (representative amino acid), and a combination of sodium chloride and sucrose.

FIG. 1 shows the results obtained after 3 days of incubating each formulation at 25° C., for exemplary pegylated carfilzomib compound 26 (a 5kPEG-CFZ construct). The graph depicts two outputs for each formulation in this study: (a) percent main peak at Time 0 ($T_0$) and Time 3 days @25° C. ($T_3$), as measured by the reverse phase assay, on the left hand y-axis, and (b) percent API material recovered at $T_3$. The main peak in the reverse phase assay represents intact API, whereas chemical modifications in the compound show up as pre- or post-main peaks, thus lowering the percent of main peak. FIG. 1 reveals that the formulations with the highest levels of intact API peaks after 3 days at 25° C. were A5Su, T7NaSu and T7Na. The formulations that performed poorly included H6Su and T8Su. The material recovery was also high for A5Su, T7NaSu and T7Na.

Visual inspection was performed for all the formulations shown in FIG. 1 after 3 days at 25° C., and the findings are provided in Table 3 below.

TABLE 3

| Formulation | Visual observation |
|---|---|
| A5Su | Clear |
| H6Su | Turbid |
| T7Su | Turbid |
| T8Su | Turbid |
| T7Na | Turbid |
| T7Pro | Turbid |
| T7Gly | Turbid |
| T7NaSu | Turbid |

Turbid means that the solution was cloudy, indicating that the carfilzomib API has not completely gone into solution. Turbidity indicated that for the API to fully dissolve more time was needed. However, turbidity can also indicate that it had reached the solubility limit. Turbidity is generally undesirable. The only formulation that appeared visibly clear after 3 days at 25° C. was A5Su. All other formulations appeared turbid, indicating that some impurity had formed which was not completely soluble in the formulation. Such impurities would likely not be desired and indicate degradation of the API or other excipient and reduced API efficacy for the composition after that time period under those particular storage conditions.

Figure 2:
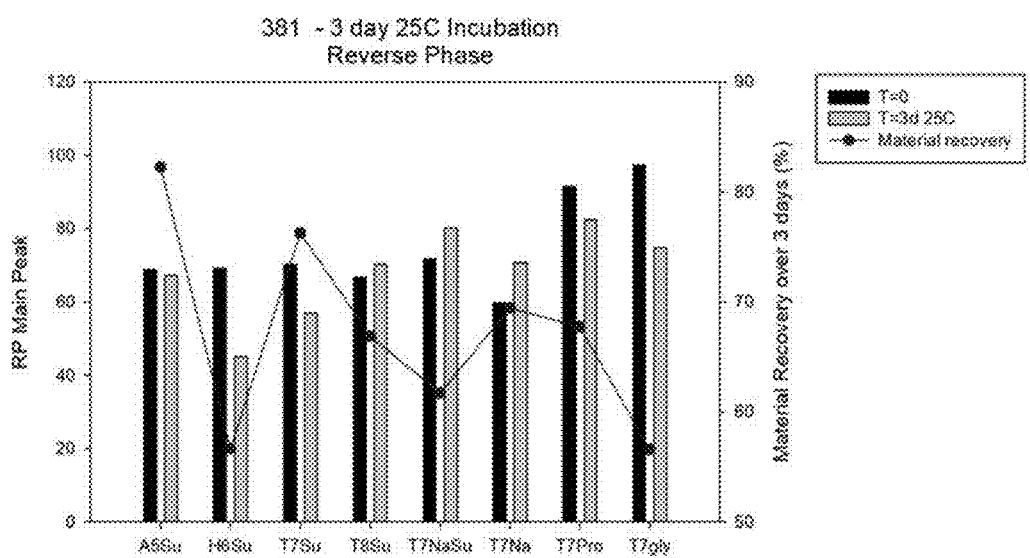
FIG. 2 is a bar graph displaying the % API (20K pegylated carfilzomib—example 39 herein) remaining as measured by reverse phase chromatography after storage at 25° C. for 3 days.

FIG. 2 illustrates results of similar measurements taken with the same formulations prepared with exemplary pegylated carfilzomib compound no. 39 instead of example 26. API material recovery is similarly shown in red and percent main API peak at $T_o$ and $T_3$, as measured by the same reverse phase assay, after storage at 25° C. for 3 days, is shown. Solutions for temperature and time storage conditions were generally prepared as follows—CFZ API was dissolved in formulation buffer by stirring at room temperature for a period of 5 minutes until complete dissolution. Samples were then sterile filtered using 0.2 micron PES filters under aseptic conditions into 3 cc vials, using a 1 ml fill. Samples were capped and crimped and placed at the desired or stated storage conditions, such as at 4° C., 25° C. or 37° C. incubators for the duration of the stability study. At each time point, the samples were pulled from incubators and an aliquot was taken for analysis.

The percent recovery of the exemplary pegylated carfilomib compounds were measured as a function of reverse phase assays for the peak(s) representing the active molecule/compound. The percent was determined based on the area under the curve, as described below. The reverse phase assays were conducted as follows—CFZ samples were analyzed by reverse phase using a Phenomenex Gemini C18, 50×4.6 mm, 3 micron particle size column with a 47 minute HPLC method. The column was held at 28 C and autosampler at 5 C for the duration of the sample run. CFZ samples are diluted to 0.4 mg/mL in mobile phase A for HPLC injection. The sample was eluted using a gradient method of 100% mobile phase A (0.1M Sodium Perchlorate Buffer, pH 3.1/Acetonitrile, 60/40, v/v) to 100% mobile phase B (0.1M Sodium Perchlorate Buffer, pH 3.1/Acetonitrile, 10/90, v/v) over 38 minutes. A wash step of 100% B lasting 5 minutes followed the gradient. A 5 minute re-equilibration step with 100% mobile phase A insured that the column was brought to the initial sample loading condition. The CFZ eluted at approximately 20-25 minutes. Main peak percentage was determined by taking Area Under the Curve integration. To calculate % recovery of the sample, a standard curve was generated using the CFZ standard (1 mg/mL CFZ in ACN diluted to 0.4 mg/mL CFZ in mobile phase A). The total integrated area for each point on the curve was plotted against the injection load, and fit with a trend-line. The concentration of each unknown sample was calculated using the equation of the trend-line generated from this calibration curve by plugging in the total integrated area.

Results in FIG. 2 reveal that the formulations that appeared stable after 3 days at 25° C., i.e. had the lowest loss of main API peak, were A5Su, T8Su, T7NaSu, T7Na and T7Pro. However, the material recovery profile (red points) was the highest for formulation A5Su.

The results of FIGS. 1 and 2 indicate that the A5Su formulation exhibited the most stability amongst those prepared and tested, for each of the 5kPEG-CFZ and 20kPEG-CFZ compounds.

The increased stability may be due, at least in part, to a reduced pH. To help ascertain whether or not pH had this effect, a second study was conducted, to compare pH3 and pH4 formulations to that of the A5Su formulation at pH5. The study design is shown in Table 4 below.

TABLE 4

| Formulation name | pH | buffer | Excipient |
| --- | --- | --- | --- |
| C3Su | 3 | 10 mM citrate | 9% sucrose |
| C4Su | 4 | 10 mM citrate | 9% sucrose |
| A5Su | 5 | 10 mM acetate | 9% sucrose |

These three compositions were then tested using all three representative PEG-CFZ constructs, namely a 3kPEG-CFZ (example 34), the 5kPEG-CFZ (example 26) and the 20kPEG-CFZ (example 39). The main API peak losses for example 34 (shown as compound 576 in Table 5) is shown in table 5.

TABLE 5

|   |   | 25 C. loss per 8 hr | 4 C. loss per 1 week | −70 C. loss per 2 weeks |
| --- | --- | --- | --- | --- |
| 576 | C3Su | 0.0 | 7.7 | 5.3 |
| 576 | C4Su | 0.0 | 8.0 | 5.1 |
| 576 | A5Su | 0.0 | 3.6 | 1.2 |

As seen in table 5, there was no loss detected (as a percentage; within experimental variability) for all 3 formulations at 25° C. after 8 hours. This indicates that these exemplary liquid formulations of pegylated carfilzomib compounds are viable for administration to a patient, either clinically or possibly commercially, after storage at room temperature after 8 hours. For storage of exemplary formulations of example 39 at each of 4° C. and −70° C. after a 2 week incubation period, both representative compositions exhibited the lowest loss in main API peak in the A5Su formulation. Further, all three representative formulations for 3kPEG-CFZ (example 34) in Table 5 appeared clear, with no particles or particulate matter visibly detected.

TABLE 6

|   | 25 C. loss per 8 hr | 4 C. Loss per 1 week | −70 C. loss per 2 weeks |
| --- | --- | --- | --- |
| C3Su | 1.1 | 1.6 | 0.9 |
| C4Su | 1.5 | 2.6 | 4.1 |
| A5Su | 0.0 | 0.0 | 0.0 |

Table 6 shows the rate of main API peak loss (as a percentage) for a representative 5kPEG-CFZ construct (compound example 26) at 25° C., 4° C. and −70° C., for the indicated formulations at pH 3, 4 and 5. Similar to what was observed in Table 5 above for the 3kPEG-CFZ construct (example 34), there was minimal main API peak loss at each of the storage conditions of 25° C. (8 h), 4° C. (in 1 week) and −70° C. (in 2 weeks).

TABLE 7

|   | 25 C. loss per 8 hr | 4 C. loss per 1 week | −70 C. loss per 2 weeks |
| --- | --- | --- | --- |
| C3Su | 20.3 | 33.5 | 25.7 |
| C4Su | 9.5 | 31.1 | 16.1 |
| A5Su | 7.0 | 28.1 | 6.4 |

Table 7 shows the rate of main API peak loss for the 20kPEG-CFZ construct compound example 39 herein) at 25° C., 4° C. and −70° C., respectively, for the formulations at pH 3, 4 and 5. Similar to what was observed in the case of the 3kPEG-CFZ construct, it was seen that there was minimal main API peak loss at 25° C. (8 h), 4° C. (in 1 week) or at −70° C. (in 2 weeks) for the representative A5Su composition. What is notable with these results is that on an absolute scale, it was observed that the 20kPEG-CFZ compound was more unstable in the A5Su formulation than the 3kPEG-CFZ and 5kPEG-CFZ constructs in the same A5Su composition make-up. More notably, is that the 20K pegylated carfilzomib compound was generally less stable to the storage conditions over time than the corresponding 3K and 5K pegylated carfilomib compounds, in the same compositional make-up.

Table 8 shows the results of a stability investigation in A5Su was performed at 20 mg/mL concentrations for each of the 3kPEG-CFZ, 5kPEG-CFZ and 20kPEG-CFZ representative pegylated carfilzomib compounds. This study shows that higher API concentration in a given formulation resulted in greater stability of the constructs at the conditions tested. It was also found that at lower concentrations, the larger peg size carfilzomib API (20kPEG-CFZ construct) was more unstable in the A5Su formulation compared to those of the 3kPEG-CFZ and 5kPEG-CFZ representative compounds.

TABLE 8

| | 25° C. loss per 8 hr | 4° C. Loss per 1 week | −70° C. loss per 2 weeks |
|---|---|---|---|
| 3K PEG-CFZ | 0.0 | 0.0 | 0.4 |
| 5K PEG-CFZ | 0.0 | 0.0 | 0.0 |
| 20K PEG-CFZ | 1.8 | 1.4 | 0.0 |

Each of the 3 PEG-CFZ construct examples were prepared as a A5Su formulation for animal dosing. These formulations were evaluated by visual assessment. Visual observation indicated no visible particulation in any of the 3 prepared samples. Endotoxin tests showed that all 3 samples contained endotoxins at levels of <1.0 EU/mL. Osmolality measurements for all 3 formulations were in the range of 299-307 mOsm. Reverse phase chromatographic assay was utilized to monitor the main API peak of all the constructs pre and post dosing. No significant loss of main API peak was detected for any of the constructs in any of the dosing studies. No significant loss of area under the curve was detected between pre and post dosing samples. This indicates that the active biological compounds in these formulations will have efficacy in the intended biological activity.

Stable, Isotonic Lyophilized Formulations for Intravenous and Subcutaneous Administration The present invention also provides stable, isotonic, dry lyophilized pharmaceutically acceptable compositions of pegylated carfilzomib compounds. A representative exemplary stable, dry lyophilized formulation, includes without limitation, G5Su2M4, which is a composition of 10 mM glutamate (buffer), 2.0% sucrose, 4% mannitol, 0.006% polysorbate 80, API at pH 5.0. Further, formulations of the present invention may further include hyaluronidase. Hyaluronidase is believed to assist with subcutaneous delivery of the API and potentially mitigate, reduce or prevent aggregation of the API and/or formulation excipients at the site of injection. Hyaluronidase is also believed to reduce the degree of local dermal irritation at the injection site.

To identify a stable lyophilized formulation of a representative 3K-pegylated carfilzomib compound (example 28 in Table 2), the compound API was dissolved in representative lyophilization compatible solutions and the stability of each exemplary solution was compared. Comparisons were made between formulations immediately upon dissolution and after completion of the lyophilization cycle. In addition, after reconstituting lyophilized batches (lyophilates), the stability of each reconstituted liquid formulation was tested to determine safe and acceptable or allowable handling times prior to drug administration, either clinical or commercial. It was seen that representative reconstituted formulations could be safely administered after at least 8 hours at room temperature and 2 days at 2-8° C. All initial screening of the constructs were performed at 5-40 mg/mL API concentrations.

For each exemplary formulation, the stability of the API was tested or measured by six different criteria or methods, as follows:

1. Integrity of the molecule, as assessed by the reverse phase assay;
2. Clarity of the solution, as determined by a visual assessment;
3. Concentration of the API material in the solution, as assessed by API material recovery after centrifugation;
4. pH of the formulation;
5. Osmolality of the exemplary solution; and
6. Sub-visible particle counts by light obscuration.

The lyophilization cycle parameters, i.e., the temperature, and the ramp and hold times, which were used in the experimental preparation are described and provided in Table 9 below. The hold step signifies no change in conditions where the samples were held at a given temperature and pressure for the duration of the step. A ramp step means that the samples were brought to desired temperature via a gradual increase or decrease until the stated temperature is reached.

TABLE 9

| Temperature (° C.) | Time (min) | Hold/Ramp step |
|---|---|---|
| 5 | 60 | H |
| −45 | 100 | R |
| −45 | 120 | H |
| −12 | 65 | R |
| −12 | 200 | H |
| −45 | 65 | R |
| −45 | 150 | H |
| −25 | 60 | R |
| −25 | 1800 | H |
| 25 | 550 | R |
| 25 | 780 | H |

The lyophilization process employed utilized a vacuum pressure of 150 mTorr.

Results

Initial lyophilization studies were conducted on exemplary formulations of API compound example 28 herein (a 3 KPEG-CFZ). The formulation consisted of the API in a desired mg amount or mg/mL concentration, 10 mM Glutamate, with 2.0% Sucrose, 4% mannitol, 0.006% polysorbate 80, and had a solution pH of 5.0. The test formulations below had various solution concentrations of API example 28 of 5, 20, and 40 mg/mL. Additionally a 10 mM histidine, pH 5.0, 2.0% sucrose, 4% mannitol, 0.006% polysorbate 80 formulation was examined at 20 mg/mL of exemplary pegylated carfilomib compound example 8 (same 3K-PEG CFZ).

FIG. 3-A shows images of the resulting dry solid lyophilization cakes obtained from the formulations prepared above. As shown, lyo cakes of compound Example 28 formulated in G5Su2M4 solution (10 mM glutamate, pH 5.0, 2.0% sucrose, 4% mannitol, 0.006% polysorbate 80) in 3 different concentrations—40 mg/mL; 20 mg/mL and 5 mg/mL. Each prepared compositional solution was frozen and lyophilized in the standard fashion. FIG. 3-A also shows the resulting dry solid lyophilization cake from a formulation solution of H5Su2M4 (10 mM histidine, pH 5.0, 2.0% sucrose, 4% mannitol, 0.006% polysorbate 80 formulations) at a 40 mg/mL concentration of compound example 28.

FIG. 3-B depicts bar graphs of the percent main compound example 28 peak in the reverse phase in-tact API measurement assay. In FIG. 3-B, the black bar represents a pre-lyophilization assay measurement, while the red bar represents a post lyophilization API peak measurement. The green bar represents a measurement taken after the lyophilization cake was reconstituted to form a clear solution and stored at 25° C. for 8 hours. Finally, the yellow bar represents an assay measurement taken after the corresponding lyophilization cake was reconstituted to form a solution and stored at 2-8° C. for 24 hours. FIG. 3-B highlights that no main API peak was lost during lyophilization and no main API peak was lost after incubations of the reconstituted solutions. Concentration of the material in the solution was obtained from reverse phase areas under the curve and did not change upon lyophilization and subsequent solution incubations.

Reconstitution of these dry solid lyophilized cakes with sterile water resulted in clear, particle free solutions. Reconstitution times were all under one minute, with the exception of the 40 mg/mL formulation. The 40 mg/mL concentration cake when reconstituted formed a clear solution only after a slightly longer time, i.e., in under two minutes. Osmolality measurements for all formulations were in the range of 300-307 mOsm. pH readings were all in the range of 5.0-5.1. As mentioned, the API reverse phase in-tact remaining compound percentages were assayed prior to and immediately after completion of the lyophilization cycle. In addition, the temperature and time periods of 25° C. for 8 hours, and between 2-8° C. for 24 hours at which the reconstituted solutions were allowed to stand were selected to mimic real world representative clinical and commercial settings for the FDA approved dosing and administration of carfilzomib.

The invention further provides pharmaceutical compositions that may be administered subcutaneously. Hylauronidase has been used in the pharmaceutical industry with certain drug products as an additive to formulations with the intent to convert an IV administered formulation to a subcutaneously administered formulation. However, hyaluronidase has not been successful in converting every drug tested to a subcutaneous administration. It is not predictable whether or not the addition of hyaluronidase will meet the requirements for subcutaneous administration of any given drug product, let alone for a pegylated carfilzmib compound. The present invention contemplates and provides compositions and formulations, as described herein, further including hyaluronidase. To this end, described below, and with reference to FIGS. 4-A and 4-B, are tests using compound example 28 wherein this compound was co-formulated with 2000 units/mL hyaluronidase (designated as PH 20, and is commercially available from various sources). A formulation solution consisting of 10 mM glutamate, pH 5.0, 2.0% sucrose, 4% mannitol, 0.006% polysorbate 80 and compound example 28 at a concentration of 20 mg/mL was prepared. This formulation (first vial) also included 2000 units/mL of hyaluronidase. It was lyophilized and the resulting dry solid lyophilization cake (See FIG. 4-A) was assayed (See FIG. 4-B) as described hereinabove to determine the percentage of main API peak remaining. The first vial in FIG. 4-A is an image of the resulting lyophilization cake obtained from the G5Su2M4 formulation described above. The second vial depicted in FIG. 4-A is a resulting placebo lyophilization cake from a solution formulation containing only hyaluronidase. This vial was prepared and lyophilized simply as a control. As described above with respect to FIG. 3-B, the API percent main peaks of both vials were measured by a reverse phase assay. As shown in FIG. 4-B, the black bar represents the API main peak of the pre-lyophilization formulation solution, while the red bar represents that of the post lyophilization cake after reconstitution with sterile water. The green bar represents the main API peak reading after each respective vial was reconstituted to form a solution that was stored at 25° C. for 8 hours and stored at 2-8° C. for 24 hours (yellow bar).

Reconstitution of both cakes (first and second vials in FIG. 4-A) with sterile water resulted in clear, particle free solutions. Reconstitution times for both vials were under one minute. Osmolality measurements for both reconstituted formulations were in the range of 300-302 mOsm. pH readings were both reconstituted formulations were found to be in the range of 5.0-5.1. The percent main peak for the pegylated carfilzomib compound example 28 was measured by reverse phase assay both prior to lyophilization and immediately after completion of the lyophilization cycle. In addition, both reconstituted solutions were stored to 25° C. for 8 hours and to 2-8° C. for 24 hours to measure stability of the API over these periods of time at these tested conditions or storage. As shown in FIG. 4-B, the reconstituted API formulation and the placebo hyaluronidase formulation show no main peak loss during lyophilization. More importantly, both of these formulation did not show any main API peak loss after incubations and storage of the reconstituted solutions at the designated times under the designated storage environments. Moreover, the concentrations of the compound example 28 in the solution, as measured by the reverse phase areas under the curve, did not change upon lyophilization and subsequent storage of the reconstituted solution. This supports and suggests that under the tested and similar conditions, the formulations of the present invention provide suitable stable, in-tact solutions which may be stored for prolonged periods of time and confidently and safely administered to patients in a research, clinical or commercial setting. The formulations of the present invention reduce the degree of degradation of a pegylated carfilzomib compound API resulting in formulations that may be stored conveniently without impurity formation and solutions that remain relatively clear of particulate matter, impurities, and contain a significant portions of, or even as much of, the active pharmaceutical ingredient as when the drug product was originally manufactured.

Hyaluronidase was sourced from Calbiochem (ovine testes, 38594-100KU, Calbiochem) and was buffer exchanged into the above formulation prior to addition of enough 3K PEG-CFZ API to achieve 20 mg/mL concentration.

The stability and safety of the formulations of the present invention were also tested or measured by particle counts and the size of particles in reconstituted solutions as a percent of the solution volume. FIGS. 5-A and 5-B illustrate the results of such particle counts, wherein the particle sizes measured is either >10µ or >25µ in diameter. The solutions used in the test include pegylated compound example 28 as the API at a concentration of 20 mg/mL, in a formulation solution consisting essentially of a composition of G5Su2M4 and 0.006% polysorbate 80. The various conditions in which the formation of particulate matter was measured in each test formulation is represented in Table 10 below. Each test formulation listed in Table 10 below was prepared in a compounding fashion and lyophilized at 1 mL fill volumes in 3 mL vials. They were then screened post lyophilization for particle formation content, as a measure of stability.

TABLE 10

| Formulation | Buffer | Cryo-protectant | Bulking Agent | Amino Acid | Surfactant |
|---|---|---|---|---|---|
| 1 | 10 mM glutamate | 2% sucrose | 4% Mannitol | none | none |
| 2 | 10 mM glutamate | 2% sucrose | 4% Mannitol | none | 0.006% PS80 |
| 3 | 10 mM glutamate | 2% sucrose | 4% Mannitol | none | 0.05% pluronic F68 |
| 4 | 10 mM glutamate | 1.2% sucrose | 4% Mannitol | 0.5% lysine | 0.006% PS80 |
| 5 | 10 mM glutamate | 0.6% sucrose | 4% Mannitol | 0.8% lysine | 0.006% PS80 |
| 6 | 10 mM glutamate | 1.2% sucrose | 4% Mannitol | 0.5% Arginine | 0.006% PS80 |
| 7 | 10 mM glutamate | 0.6% sucrose | 4% Mannitol | 0.8% Arginine | 0.006% PS80 |

Each formulation vial was tested for particle counts by sub visible light obscuration methodology, before and after lyophilization. This methodology involved using liquid particle counting system (HIAC/Royco 9703 or 9703+). In case of post lyophilized samples, reconstitution was performed prior to measurement and samples were allowed to equilibrate for a period of two hours prior to analysis. Prior to measurement, all samples were degassed for a period of one hour using a vacuum chamber. Post degassing the samples, water controls and particle standards were measured by the instrument. Water control samples measurement readings of zero had to be obtained prior to standard particle control and sample measurements. In brief, samples were gently swirled by hand as to not generate any bubbles, then measured by the instrument using a 0.2 mL sip per measurement. A total of 4 sips were performed per sample, with the last three sips being averaged. No sample dilution was performed for any of the samples tested.

As shown in FIGS. 5-A and 5-B, a significant increase in particle counts can be seen in formulations 1-3. The addition of a surfactants polysorbate 80 and pluronic F68 only slightly decreased or reduced the propensity to form particulate matter in the formulation (10 mM glutamate+2% sucrose+4% mannitol at pH 5.0). it was found that the addition of an amino acid, such as lysine or arginine, in small amounts in combination with a surfactant such as polysorbate 80 results in lowering particle counts in both tested formulations, counts >10μ and counts >25 microns in size.

By way of summary, the representative formulation made and tested by lyophilization are represented in Table 11 below.

TABLE 11

| Formulation | mgs of Example 28 in each lyophilized cake |
|---|---|
| G5SU2M4, 40 mg/ml example 28 | 40 mg |
| G5SU2M4, 40 mg/ml example 28 | 20 mg |
| H5SU2M4, 5 mg/ml example 28 | 5 mg |
| H5SU2M4, 40 mg/ml example 28 | 40 mg |
| G5SU2M4, 20 mg/ml example 28, hyaluronidase | 20 mg |
| G5Su1.2-2M4 0.5-0.8K or R, 20 mg/mL example 28 (all formulations from FIG. 5/Table 10 | 20 mg |

Administration of the Pharmaceutical Compositions of the Invention

The pharmaceutical compositions of the present invention may be parenterally administered. For example, parenterally administered compositions may be formulated as injections (intravenous, intramuscular, or subcutaneous), drop infusion preparations, or suppositories. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent. Parenterally administrable compositions suitable for infusion, injection or sub-cutaneous administration generally include sterile aqueous solutions (where water soluble) or dispersions and/or sterile powders for the extemporaneous preparation of sterile solutions or dispersions for either infusion or injection. For intravenous administration, suitable carriers include sterile water for injection, sterile buffers, as described above. In all cases, the compositions, particularly for human use, treatment and consumption, must be sterile and should be fluid to the extent that it is easy to add to or pull up into a syringe or infusion bag. The composition should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. Thus, in some aspects, the invention provides compositions that may include antibacterial or antifungal agents. In some aspects of the invention, the compositions provided herewith may include isotonic agents, for example, sugars, polyalcohols such as mannitol, sorbitol, and sodium chloride in the composition, as exemplified and tested hereinabove. Prolonged absorption of the injectable compositions can be brought about by including in the composition an agent that delays absorption, for example, aluminum monostearate and gelatin.

Sterile injectable solutions can be prepared by incorporating the active PEG carfilzomib compounds, in the required amount in an appropriate solvent with one or a combination of ingredients enumerated above, as required, followed by filtered sterilization. Generally, dispersions are prepared by incorporating the carfilzomib into a sterile vehicle, which contains a basic dispersion medium and the required other ingredients from those enumerated above. In the case of sterile powders, such as the lyophilized cakes made and described herein, for the preparation of sterile injectable solutions, a suitable method of preparation is freeze-drying (lyophilization), which provides a powder form of the active pegylated carfilzomib compound plus any additional desired ingredient from a previously sterile-filtered solution thereof.

The dosage amount of the pegylated carfilzomib compounds used in the pharmaceutical compositions of the invention described herein and the precise time of administration depends on the type of nature of the cancer to be treated, and the age, condition, and body weight of the patient. The composition that will yield the most effective results in terms of efficacy of treatment in a given patient will also depend upon the activity, pharmacokinetics, and bioavailability of the particular PEG carfilzomib compound, physiological condition of the patient as stated above (including age, sex, disease type and stage, general physical condition, responsiveness to a given dosage, and type of medication), route of administration, and the like. Although the dosage will vary depending on the symptoms and severity of the disorder to be treated or prevented, the route of administration and the form of the drug, in general, a daily dosage of from 0.01 to 2000 mg of the compound is recommended for an adult human patient, and this may be administered in a single dose or in divided doses. More information on the dosage amounts for compounds of the invention is provided herein below. In general, compositions intended for parenteral use (e.g., intravenous, subcutaneous injection) include a solubilizing agent. The solubilizing agent may be a substituted cyclodextrin.

The actual dosage amounts of the PEG carfilzomib compound utilized in the pharmaceutical compositions provided by the invention may be an amount which is clinically proven to be effective, and/or commercially approved as effective, to achieve the desired therapeutic response for a cancer patient, including without limitation, for a multiple myeloma patient. In some aspects, the invention provides pharmaceutical compositions as an aqueous solution containing about 0.1-20% w/v of a compound disclosed herein, among other substances, for parenteral administration. Typical dose ranges for the PEG carfilzomib compound are from about 0.01 to about 50 mg/kg of body weight per day, given in 1-4 divided doses each day. Each divided dose will contain one or more of the compounds provided by the invention. The desired, specific compound dosage amount should be an amount sufficient to provide a therapeutically effective dosage of free acting carfilzomib in the plasma of the patient, the effective dosage amount being based on regulatory approved use, for regulatory approved indications. This effective amount may vary from patient to patient, and is generally dependent on several factors including the overall health of a patient, and the specific formulation composition and route of administration of the chosen compound(s). In some embodiments, the PEG carfilzomib compounds that may be used in the present invention are described in U.S. Pat. No. 9,309,283.

Carfilzomib is currently approved in doses, provided once daily for the first 2 consecutive days every week for 3 consecutive weeks in a 28 day cycle, in an amount sufficient to provide a patient plasma concentration ranging from 20 mg/m$^2$ to 56 mg/m$^2$. Thus, a higher molecule weight PEG carfilzomib compound of the invention should be administered in amounts sufficient to pharmacokinetically provide amounts approximately equivalent to approved dosing ranges. For example, a 2K PEG compound of the invention is approximately 24% by weight of free carfilzomib. Thus, using an average male with 1.9 m2 average body surface, to achieve about an equivalent dose of 27 mg/m$^2$, one would have to dose about 215 mg of the 2 k PEG CFZ compound. Similarly, one may dose about 1100 mg of a 20K PEG CFZ compound to deliver the same amount of carfilzomib as would a 70 mg/m$^2$ dose of the currently approved formulation for carfilzomib.

The pharmaceutical compositions of the present invention include various excipients as described herein. For instance, the at least one excipient may include a sugar additive such as sucrose, sorbital, glycerin, maltose, lactose, erythrose, dextrose, lactobiose, or a cyclodextrin, or a charged amino acid such as proline, glycine, arginine, histidine, aspartic acid, glutamic acid or glutamate, or a neutral, hydrophobic amino acid such as valine, leucine, alanine, methionine. The excipient may be a salt selected from the group consisting of sodium chloride, potassium chloride, ammonium sulfate, potassium chlorate, calcium chloride, zinc chloride, guanidine hydrochloride, ammonium chloride, potassium sulfate, ammonium aspartate, arginine-HCl, lysine-HCl, magnesium chloride and barium sulfate. If the excipient is a sugar, it is generally included in an amount ranging from about 0.1-30% by total weight of the composition or % weight per volume of the solution formulation or if it is an amino acid then it is generally included in an amount ranging from about 0.1-10% by total weight of the composition.

The pharmaceutical compositions of the invention may further include other excipients as well, that are pharmaceutically acceptable. The term "pharmaceutically acceptable" as herein with respect to excipients, carriers and/or diluents in the compositions of the present invention, refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. "Pharmaceutically acceptable carrier" as used herein means a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient.

Additional excipients include, use of surfactants including, without limitation, PS20, PS80, PL F68 (and other pluronics in the F and L series) triblock surfactant polymers, docusate sodium, benzaconium chloride, triton X 100, and tetra functional block O polymers. A surfactant that may be included is generally one that lowers surface tension (such as an alcohol), SDS, protamine sulfate, or butane. The surfactant, if included in the compositions of the invention, should be included in amounts ranging from 0.005 to 3% by weight.

For dry lyophilized compositions provided by the present invention, a sugar such as sucrose, sorbitol, glycerin, maltose, lactose, erythrose, dextrose, lactobiose, cyclodextrins, sugar derivatives and adducts maybe included. The sugar or sugar derivative is generally included in an amount ranging from about 0.1-30% by weight. Where the excipient may be an amino acid, it maybe any suitable amino acid including proline glycine, lysine, arginine, histidine, aspartic acid, valine, leucine, alanine, methionine, proline, glutamic acid, glutamate. The amino acid should generally be present in an amount ranging from about 0.1-10% by weight. The compositions of the present invention may further include a salt. The salt may function as a buffering effect or provide other advantages to the composition. The salt may be, for instance, NaCl, KCl, ammonium sulfate, potassium chlorate, calcium Cl, Zn Cl, guanidine hydrochloride, ammonium chloride, potassium sulfate, amino acid salts including without limitation, ammonium aspartate, arginine-HCl, and lysine-HCl, magnesium chloride, and barium sulfate. When a salt is included, it is generally included in an amount ranging from about 30-300 mM by volume of the solution composition.

Additional examples of materials which can typically serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

Pharmaceutical compositions typically include a pharmaceutically acceptable carrier. As used herein the language "pharmaceutically acceptable carrier" includes a buffer, sterile water for injection, solvents, dispersion media, coatings, antibacterial and antifungal agents, isotonic and absorption delaying agents, and the like, compatible with pharmaceutical administration. In some embodiments, a pharmaceutically acceptable carrier is an acid-base buffer system, such as a citrate buffer, to maintain a stable pH for the resulting solution. In some embodiments, a pharmaceutically acceptable carrier is sterile water for injection. In some embodiments, a pharmaceutically acceptable carrier comprises citric acid.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of the injectable pharmaceutical form may be brought about by the inclusion of agents which delay absorption such as aluminum monostearate and gelatin. In some cases, in order to prolong the effect of a drug, it is desirable to slow the absorption of the drug from subcutaneous or intramuscular injection. For example, delayed absorption of a parenterally administered drug form is accomplished by dissolving or suspending the drug in an oil vehicle.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The pharmaceutical compositions of the invention described herein may be administered to humans and other animals, including mammals, for therapy by any suitable route of administration.

Methods of Use

The biological effects of proteasome inhibition are useful and desirable. Proteasome inhibition has been suggested as a prevention and/or treatment of a multitude of diseases including, but not limited to, proliferative diseases, neurotoxic/degenerative diseases, Alzheimer's, ischemic conditions, inflammation, auto-immune diseases, HIV, cancers, organ graft rejection, septic shock, inhibition of antigen presentation, decreasing viral gene expression, parasitic infections, conditions associated with acidosis, macular degeneration, pulmonary conditions, muscle wasting diseases, fibrotic diseases, bone and hair growth diseases. Therefore, pharmaceutical formulations comprising the PEG carfilzomib compounds of the invention in therapeutically effective dosage amounts provide a means of administering a drug to a patient and treating these conditions.

At the cellular level, the accumulation of polyubiquitinated proteins, cell morphological changes, and apoptosis have been reported upon treatment of cells with various proteasome inhibitors. Proteasome inhibition has also been disclosed, and clinically and commercially proven as a useful antitumor therapeutic strategy. To this end, the compounds and compositions including the compounds of the present invention are useful for treating cancer, including without limitation, newly diagnosed and/or relapsed and refractory multiple myeloma.

Both in vitro and in vivo models have shown that malignant cells, in general, are susceptible to proteasome inhibition. In fact, proteasome inhibition has already been validated as a therapeutic strategy for the treatment of multiple myeloma. This could be due, in part, to the highly proliferative malignant cell's dependency on the proteasome system to rapidly remove proteins (Rolfe et al., *J. Mol. Med* (1997) 75:5-17; Adams, *Nature* (2004) 4: 349-360). Provided herein is a method of treating cancer comprising administering to a patient in need of such treatment a therapeutically effective amount of a pegylated carfilzomib compound of formulas I and II, or any specifically exemplified PEG carfilzomib compound, as provided or described herein.

As used herein, the term "cancer" includes, but is not limited to, blood borne cancers and solid tumors. Cancer may afflict components of blood, bone, organs, skin tissue and the vascular system, including, but not limited to, cancers of the bladder, blood, bone, brain, breast, cervix, chest, colon, endrometrium, esophagus, eye, head, kidney, liver, lung, lymph nodes, mouth, neck, ovaries, pancreas, prostate, rectum, renal, skin, stomach, testis, throat, and uterus. Specific cancers include, but are not limited to, leukemia (acute lymphocytic leukemia (ALL), acute myelogenous leukemia (AML), chronic lymphocytic leukemia (CLL), chronic myelogenous leukemia (CML), hairy cell leukemia), mature B cell neoplasms (small lymphocytic lymphoma), B cell prolymphocytic leukemia, lymphoplasmacytic lymphoma (such as Waldenstrbm's macroglobulinemia), splenic marginal zone lymphoma, plasma cell myeloma, plasmacytoma, monoclonal immunoglobulin deposition diseases, heavy chain diseases, extranodal marginal zone B cell lymphoma (MALT lymphoma), nodal marginal zone B cell lymphoma (NMZL), follicular lymphoma, mantle cell lymphoma, diffuse B cell lymphoma, mediastinal (thymic) large B cell lymphoma, intravascular large B cell lymphoma, primary effusion lymphoma and Burkitt lymphoma/leukemia), mature T cell and natural killer (NK) cell neoplasms (T cell prolymphocytic leukemia, T cell large granular lymphocytic leukemia, aggressive NK cell leukemia, adult T cell leukemia/lymphoma, extranodal NK/T cell lymphoma, enteropathy-type T cell lymphoma, hepatosplenic T cell lymphoma, blastic NK cell lymphoma, mycosis fungoides (Sezary syndrome), primary cutaneous anaplastic large cell lymphoma, lymphomatoid papulosis, angioimmunoblastic T cell lymphoma, unspecified peripheral T cell lymphoma and anaplastic large cell lymphoma), Hodgkin lymphoma (nodular sclerosis, mixed celluarity, lymphocyte-rich, lymphocyte depleted or not depleted, nodular lymphocyte-predominant), non-hodgkin's lymphoma, myeloma (multiple myeloma, indolent myeloma, smoldering myeloma), chronic myeloproliferative disease, myelodysplastic/myeloproliferative disease, myelodysplastic syndromes, immunodeficiency-associated lymphoproliferative disorders, histiocytic and dendritic cell neoplasms, mastocytosis, chondrosarcoma, Ewing sarcoma, fibrosarcoma, malignant giant cell tumor, myeloma bone disease, osteosarcoma, breast cancer (hormone dependent, hormone independent), gynecological cancers (cervical, endometrial, fallopian tube, gestational trophoblastic disease, ovarian, peritoneal, uterine, vaginal and vulvar), basal cell carcinoma (BCC), squamous cell carcinoma (SCC), malignant melanoma, dermatofibrosarcoma protuberans, Merkel cell carcinoma, Kaposi's sarcoma, astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, teratoma, malignant mesothelioma (peritoneal mesothelioma, pericardial mesothelioma, pleural mesothelioma), gastro-enteropancreatic or gastroenteropancreatic neuroendocrine tumor (GEP-NET), carcinoid, pancreatic endocrine tumor (PET), colorectal adenocarcinoma, colorectal carcinoma, aggressive neuroendocrine tumor, leiomyosarcomamucinous adenocarcinoma, Signet Ring cell adenocarcinoma, hepatocellular carcinoma, cholangiocarcinoma, hepatoblastoma, hemangioma, hepatic adenoma, focal nodular hyperplasia (nodular regenerative hyperplasia, hamartoma), non-small cell lung carcinoma (NSCLC) (squamous cell lung carcinoma, adenocarcinoma, large cell lung carcinoma), small cell lung carcinoma, thyroid carcinoma, prostate cancer (hormone refractory, androgen independent, androgen dependent, hormone-insensitive), and soft tissue sarcomas (fibrosarcoma, malignant fibrous hystiocytoma, dermatofibrosarcoma, liposarcoma, rhabdomyosarcoma leiomyosarcoma, hemangiosarcoma, synovial sarcoma, malignant peripheral nerve sheath tumor/neurofibrosarcoma, extraskeletal osteosarcoma).

In one aspect, the invention provides a pharmaceutically acceptable composition comprising a pegylated carfilzomib compound, or a pharmaceutical acceptable salt thereof, that is administered to patient for the treatment of multiple myeloma. Further, and in another aspect of the invention, the multiple myeloma can include either or both newly diagnosed or relapsed and/or refractory multiple myeloma.

Figure 6:
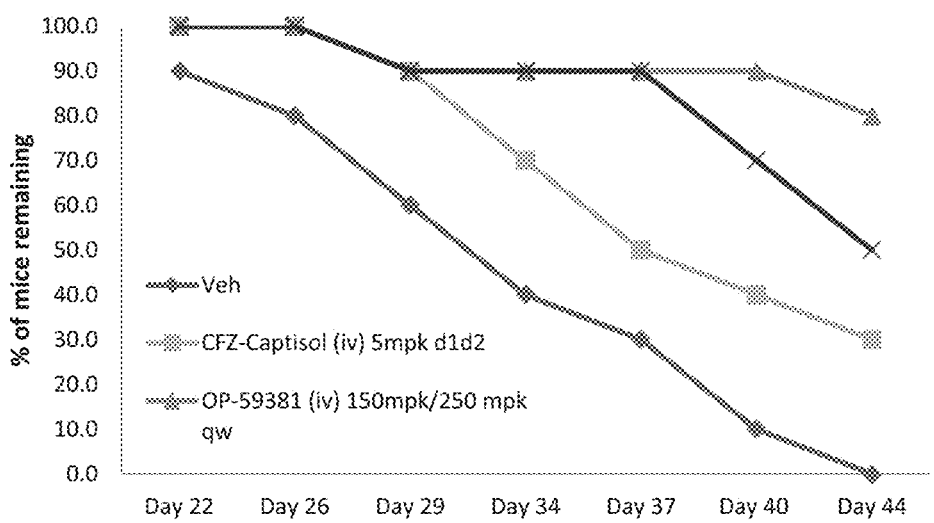
FIG. 6 is a graph the results of the in-vitro effects of an exemplary pegylated carfilzomib compound in a cancer tumor xenograph model.
Figure 7:
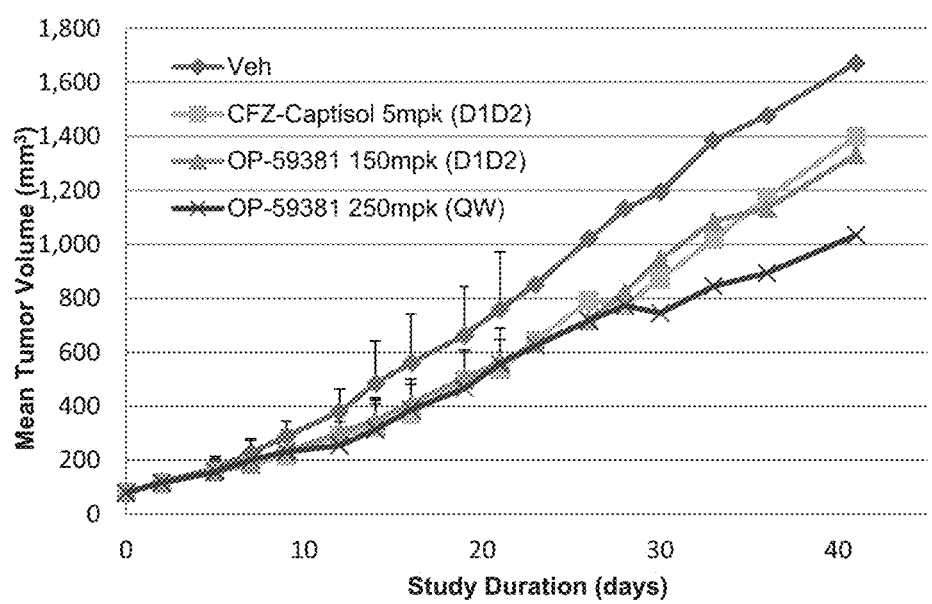
FIG. 7 is a graph the results of the effects of an exemplary pegylated carfilzomib compound described herein on a cancerous tumor.

FIGS. 6 and 7 reveal the efficacy of a representative pegylated carfilzomib compound Example 13 in a mouse xenograft model of human colorectal adenocarcinoma cancer cell. Tumors in the vehicle group grew linearly during the study. Once-weekly intravenous dosing with compound Example 13 (200 mpk, or 150 rising to 250 mpk after 3 week) or with CFZ-captisol (5 mpk) provided significant attenuation of tumor growth (compared to vehicle control) within 19 days of the first dose administration. In addition, intravenous dosing with the both formulations was associated with significant attenuation of weight gain.

Additional embodiments include methods for affecting the proteasome-dependent regulation of oncoproteins and methods of treating or inhibiting cancer growth, each method including exposing a cell (in vivo, e.g., in a patient, or in vitro) to a composition disclosed herein. HPV-16 and HPV-18-derived E6 proteins stimulate ATP- and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. One embodiment is a method for treating p53-related apoptosis, including administering to a patient an effective amount of a composition disclosed herein.

It has also been demonstrated that inhibitors that bind to the 20S proteasome stimulate bone formation in bone organ cultures. Furthermore, when such inhibitors have been administered systemically to mice, certain proteasome inhibitors increased bone volume and bone formation rates over 70% (Garrett, I. R. et al., *J. Clin. Invest.* (2003) 111: 1771-1782), therefore suggesting that the ubiquitin-proteasome machinery regulates osteoblast differentiation and bone formation. Therefore, the disclosed compositions may be useful in the treatment and/or prevention of diseases associated with bone loss, such as osteoporosis.

Further, the invention provides compositions that are also useful as diagnostic agents (e.g., in diagnostic kits or for use in clinical laboratories) for screening for proteins (e.g., enzymes, transcription factors) processed by Ntn hydrolases, including the proteasome. The disclosed compositions are also useful as research reagents for specifically binding the X/MB1 subunit or α-chain and inhibiting the proteolytic activities associated with it. For example, the activity of (and specific inhibitors of) other subunits of the proteasome can be determined.

In embodiment 71 of the invention, there is provided a method of treating cancer in a subject in need of treatment, the method comprising administering to the subject an effective dosage amount of a pharmaceutical composition comprising an effective amount of a PEG carfilzomib compound of Formula I. In embodiment 72, the invention provides the method of embodiment 71 wherein the cancer is multiple myeloma. In embodiment 73, the invention provides the method of any one of embodiments 71-72 wherein the effective dosage amount of PEG carfilzomib is in the range from about 100 mg to about 2000 mg. In embodiment 74, the invention provides the method of any one of embodiments 71-73 wherein the effective dosage amount is in the range from about 150 mg to about 1000 mg per day. In embodiment 75, the invention provides the method of any one of embodiments 71-74 wherein the effective dosage amount of the PEG carfilzomib compound administered is in the range from about 200 mg to about 500 mg per day. In embodiment 76, the invention provides the method of any one of embodiments 71-73 wherein the effective dosage amount of a 2K PEG carfilzomib compound administered is in the range from about 150 mg to about 600 mg per day. In embodiment 77, the invention provides the method of any one of embodiments 71-73 wherein the effective dosage amount of a 3K PEG carfilzomib compound administered is in the range from about 300 mg to about 2000 mg per day. In embodiment 78, the invention provides the method of any one of embodiments 71-73 wherein the effective dosage amount of a 5K PEG carfilzomib compound administered is in the range from about 800 mg to about 3000 mg per day. In embodiment 79, the invention provides the method of any one of embodiments 71-73 wherein the effective dosage amount of a 20K PEG carfilzomib compound administered is in the range from about 800 mg to about 3000 mg per day. In embodiment 80, the invention provides the method of any one of embodiments 71-73 wherein the effective dosage amount of a PEG carfilzomib compound administered is in the range from about 200 mg to about 1500 mg per day. In embodiment 81, the invention provides the method of any one of embodiments 71-73 wherein the effective dosage amount of the PEG carfilzomib compound administered is in the range from about 5 mg/kg to about 50 mg/kg by weight of the subject per day. In embodiment 82, the invention provides the method of any one of embodiments 71-73 wherein the effective dosage amount of a 2K, 3K or 5K PEG carfilzomib compound administered is in the range from about 200 mg to about 800 mg per day. In embodiment 83, the invention provides the method of any one of embodiments 71-73 wherein the effective dosage amount of a 2K or 3K PEG carfilzomib compound administered is in the range from about 200 mg to about 500 mg per day. In embodiment 84, the invention provides the method of any one of embodiments 71-73 wherein the effective dosage amount of a 5K or 20K PEG carfilzomib compound administered is in the range from about 400 mg to about 1000 mg per day. In embodiment 85, the invention provides the method of any one of embodiments 71-84, wherein the method further comprises administration of a steroid. In embodiment 86, the invention provides the method of embodiment 85 wherein the steroid is selected from the group consisting of dexamethasone and prednisone. In embodiment 87, the invention provides the method of any one of embodiments 85-86 wherein the steroid is dexamethasone. In embodiment 88, the invention provides the method of any one of embodiment 85-86 wherein the steroid is prednisone. In embodiment 89, the invention provides the method of any one of embodiments 71-88 wherein the method further comprises administration of an immunomodulatory agent selected from the group consisting of thalidomide, lenalidomide and pomalidomide. In embodiment 90, the invention provides the method of embodiment 89, wherein the immunomodulatory agent is lenalidomide or pomalidomide. In embodiment 91, the invention provides the method of any one of embodiments 89-90, wherein the immunomodulatory agent is lenalidomide. In embodiment 92, the invention provides the method of any one of embodiments 89-90, wherein the immunomodulatory agent is pomalidomide. In embodiment 93, the invention provides the method of any one of embodiments 71-88 wherein the method further comprises administration of a CD-38 inhibiting agent. In embodiment 94, the invention provides the method of embodiment 93, wherein the CD-38 inhibiting agent is daratumumab. In embodiment 95, the invention provides the method of any one of embodiments 71-94 wherein the cancer is relapsed or refractory multiple myeloma. In embodiment 96, the invention provides the method of any one of embodiments 71-94 wherein the cancer is new diagnosed multiple myeloma. In embodiment 97, the invention provides the method of embodiment 96 wherein the cancer is new diagnosed multiple myeloma and wherein the patient is stem cell transplant eligible, as determined by a licensed, authorized medical practitioner. In embodiment 98, the invention provides the method of embodiment 96 wherein the cancer is new diagnosed multiple myeloma and wherein the patient is not stem cell transplant eligible, as determined by a licensed, authorized medical practitioner. In embodiment 99, the invention provides the method of any one of embodiments 71-98, wherein the method comprises administering to the subject a pharmaceutical composition comprising a PEG carfilzomib compound of Formula 1. In embodiment 101, the invention provides the method of any one of embodiments 99-100 wherein the pharmaceutical composition is a freeze-dried preparation that can be reconstituted prior to administration.

Combinations

While a PEG-carfilzomib compound of the invention can be dosed or administered as the sole active pharmaceutical agent, it can also be used in combination with one or more agents, such a second anti-cancer agent. When administered as a combination, the PEG carfilzomib active ingredient and the other agent may be formulated as separate compositions that are administered simultaneously or sequentially at different times, or both active agents can be given as a single composition.

The phrase "co-therapy" (or "combination-therapy"), in defining the use of PEG carfilzomib compound of the present invention and another anti-cancer agent, is intended to embrace administration of each agent in a sequential manner in a regimen that will provide beneficial effects of the drug combination, and is intended as well to embrace co-administration of these agents in a substantially simultaneous manner, such as in a single dosage formulation having a fixed ratio of these active agents, or in multiple, separate dosage formulations for each active agent. Thus, the invention is not limited in the sequence of administration, i.e, the PEG carfilzomib compound(s) may be administered either prior to, simultaneously with or after administration of the other agent.

In certain embodiments, a PEG-carfilzomib compound described herein is conjointly administered with one or more other proteasome inhibitor(s). Another proteasome inhibitor may include, for example, bortezomib, oprozomib or ixazomib. In another embodiment, the PEG carfilzomib compound described herein is administered in combination with an immunomodulatory compound, including thalidomide, lenalidomide and pomalidomide. In an embodiment from the immediately preceding embodiment, the PEG carfilzomib is administered in combination with an immunomodulatory agent selected from lenalidomide and pomalidomide. In a further embodiment, the invention provides a method of treating cancer in a subject by administering to the subject a combination therapy comprising a PEG carfilzomib compound of Formula I or II and an immunomodulatory agent. In a further embodiment, the cancer is multiple myeloma.

In certain embodiments, a PEG-carfilzomib compound described herein is conjointly administered with one or more chemotherapeutics. Suitable chemotherapeutics may include, natural products such as *vinca* alkaloids (i.e. vinblastine, vincristine, and vinorelbine), taxanes (e.g., docetaxel, paclitaxel, e.g., docetaxel), epidipodophyllotoxins (i.e. etoposide, teniposide), antibiotics (dactinomycin (actinomycin D) daunorubicin, doxorubicin and idarubicin; e.g., doxorubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, ifosphamide, cyclophosphamide and analogs, melphalan, chlorambucil, e.g., melphalan), ethylenimines and methylmelamines (hexaamethylmelaamine and thiotepa), alkyl sulfonates (busulfan), nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine); aromatase inhibitors (anastrozole, exemestane, and letrozole); platinum coordination complexes (cisplatin, carboplatin), procarbazine, hydroxyurea, mitotane, aminoglutethimide; DNA binding/Cytotoxic agents (e.g., Zalypsis); histone deacetylase (HDAC) inhibitors (e.g., trichostatin, sodium butyrate, apicidan, suberoyl anilide hydroamic acid (SAHA (Vorinostat)), trichostatin A, depsipeptide, apicidin, A-161906, scriptaid, PXD-101, CHAP, butyric acid, depudecin, oxamflatin, phenylbutyrate, valproic acid, MS275 (N-(2-Aminophenyl)-4-[N-(pyridine-3-ylmethoxy-carbonyl)aminomethyl]benzamide), LAQ824/LBH589, C1994, MGCD0103, ACY-1215, Panobinostat); hormones (i.e. estrogen) and hormone agonists such as leutinizing hormone releasing hormone (LHRH) agonists (goserelin, leuprolide and triptorelin). Other chemotherapeutic agents may include mechlorethamine, camptothecin, ifosfamide, tamoxifen, raloxifene, gemcitabine, navelbine, or any analog or derivative variant of the foregoing.

In certain embodiments, a PEG-carfilzomib compound described herein is conjointly administered with a cytokine. Cytokines include, but are not limited to, Interferon-γ, -α, and -β, Interleukins 1-8, 10 and 12, Granulocyte Monocyte Colony-Stimulating factor (GM-CSF), TNF-α and -β, and TGF-β.

In certain embodiments, a PEG-carfilzomib compound described herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof (e.g., hydrocortisone, dexamethasone, methylprednisolone and prednisolone; e.g., dexamethasone). In certain embodiments, a PEG-carfilzomib compound described herein are conjointly administered with dexamethasone. In certain embodiments, conjoint therapy includes the dosing regimens provided on the KYPROLIS (carfilzomib) label, as approved by the US FDA and by the EMA.

In some embodiments, a PEG-carfilzomib compound described herein is conjointly administered with an immunotherapeutic agent. Suitable immunotherapeutic agents may include, but are not limited to, MDR modulators (verapamil, valspordar, biricodar, tariquidar, laniquidar), cyclosporine, thalidomide, and monoclonal antibodies. The monoclonal antibodies can be either naked or conjugated such as rituximab, tositumomab, alemtuzumab, epratuzumab, ibritumomab tiuxetan, gemtuzumab ozogamicin, bevacizumab, cetuximab, erlotinib and trastuzumab.

In certain embodiments, a PEG-carfilzomib compound described herein is conjointly administered with one or more histone deacetylase (HDAC) inhibitors (e.g., trichostatin, sodium butyrate, apicidan, suberoyl anilide hydroamic acid ("SAHA" (Vorinostat)), trichostatin A, depsipeptide, apicidin, A-161906, scriptaid, PXD-101, CHAP, butyric acid, depudecin, oxamflatin, phenylbutyrate, valproic acid, MS275 (N-(2-Aminophenyl)-4-[N-(pyridine-3-ylmethoxycarbonyl)aminomethyl]benzamide), LAQ824/LBH589, CI994, MGCD0103, ACY-1215, Panobinostat; e.g., SAHA, ACY-1215, Panobinostat).

In certain embodiments, a PEG-carfilzomib compound described herein is conjointly administered with one or more nitrogen mustards (mechlorethamine, ifosphamide, cyclophosphamide and analogs, melphalan, chlorambucil, e.g., melphalan).

In certain embodiments, a PEG-carfilzomib compound described herein is conjointly administered with one or more DNA binding/Cytotoxic agents (e.g., Zalypsis).

In certain embodiments, a PEG-carfilzomib compound described herein is conjointly administered with one or more taxanes (e.g., docetaxel, paclitaxel, e.g., docetaxel).

In certain embodiments, a PEG-carfilzomib compound described herein is conjointly administered with one or more antibiotics (dactinomycin (actinomycin D) daunorubicin, doxorubicin and idarubicin; e.g., doxorubicin).

The foregoing is merely illustrative of the invention and is not intended to limit the invention to the disclosed uses. Variations and changes, which are routine to one skilled in the art, are intended to be within the scope and nature of the invention, which are defined in the appended claims.

What is claimed is:

1. A pharmaceutical composition comprising (a) a pegylated carfilzomib compound in an amount ranging from 100 mg to 3000 mg; and (b) 10 mM glutamate, 2% w/v sucrose, and 4% w/v mannitol, or 10 mM glutamate, 2% w/v sucrose, 4% w/v mannitol, and 0.006% w/v polysorbate 80, or 10 mM glutamate, 2% w/v sucrose, 4% w/v mannitol, and 0.05% w/v pluronic F68, or 10 mM glutamate, 2% w/v sucrose, 4% w/v mannitol, 0.5% w/v lysine and 0.006% w/v polysorbate 80, or 10 mM glutamate, 2% w/v sucrose, 4% w/v mannitol, 0.8% w/v lysine and 0.006% w/v polysorbate 80, or 10 mM glutamate, 2% w/v sucrose, 4% w/v mannitol, 0.5% w/v arginine and 0.006% w/v polysorbate 80, or 10 mM glutamate, 2% w/v sucrose, 4% w/v mannitol, 0.8% w/v arginine and 0.006% w/v polysorbate 80.

2. The pharmaceutical composition of claim 1 wherein the pegylated carfilzomib compound has a structure of formula I

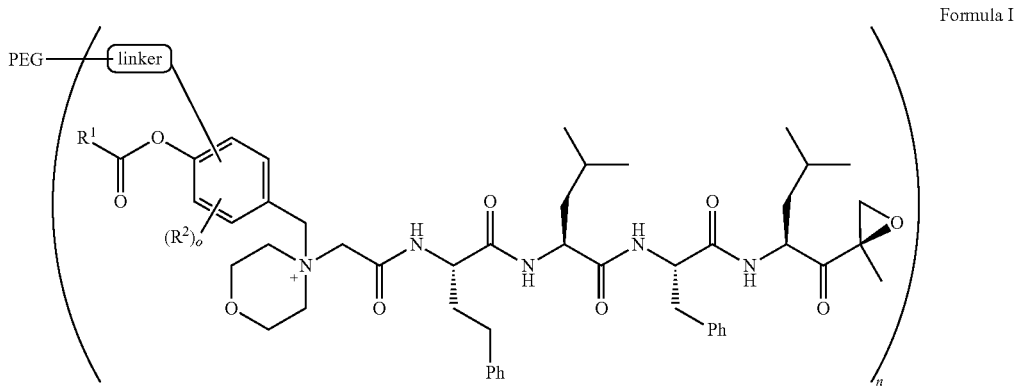

Formula I or a pharmaceutically acceptable salt thereof, wherein
R$^1$ is C$_{1-10}$alkyl or C$_{3-7}$cycloalkyl;
each R$^2$, independently, is C$_{1-6}$alkyl, —OCH$_3$ or halogen;
o is an integer selected from 0, 1, 2 or 3;
linker is a moiety having the structure of

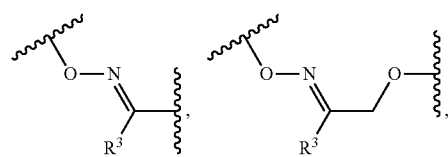

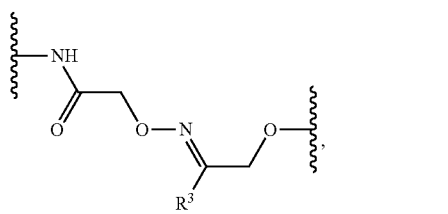

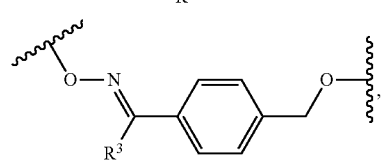

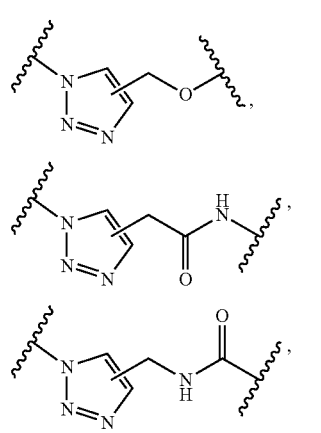

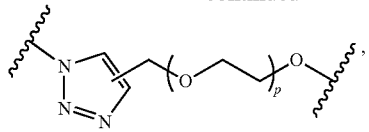

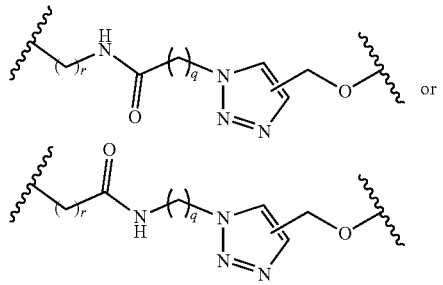

wherein R$^3$ is H or CH$_3$;
n is an integer selected from 1, 2, 3 or 4;
p is an integer selected from 0, 1, 2, 3 or 4;
q is an integer selected from 1, 2, 3, 4, 5, 6, 7, 8 or 9;
r is an integer selected from 0, 1, 2, 3, 4 or 5; and
PEG is a polyethylene glycol polymeric moiety having a molecular weight ranging from about 500 to about 20,000.

3. The composition of claim 2, wherein the linker is a moiety having the structure of

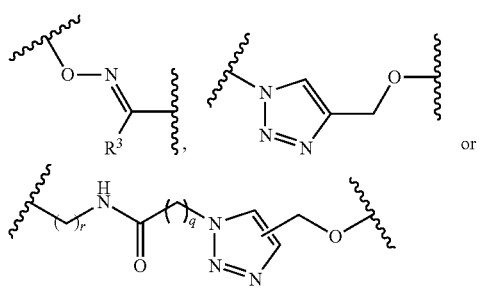

wherein R$^3$ is H or CH$_3$;
q is 4; and
r is 2.

4. The composition of claim 1, wherein the pegylated carfilzomib compound has the structure of
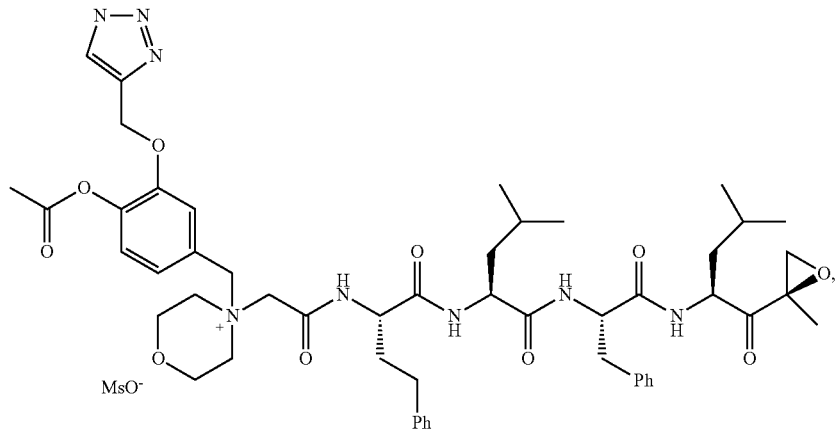
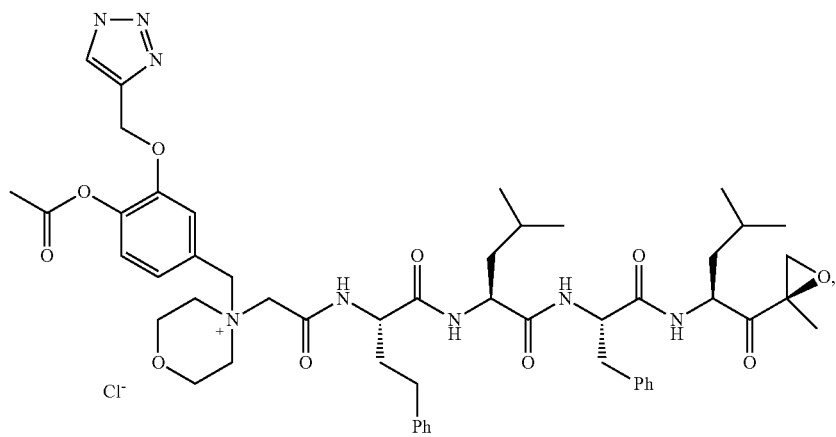
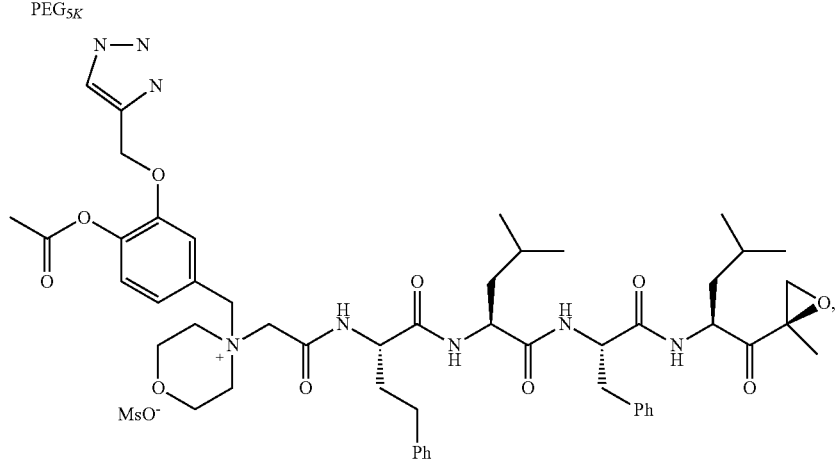

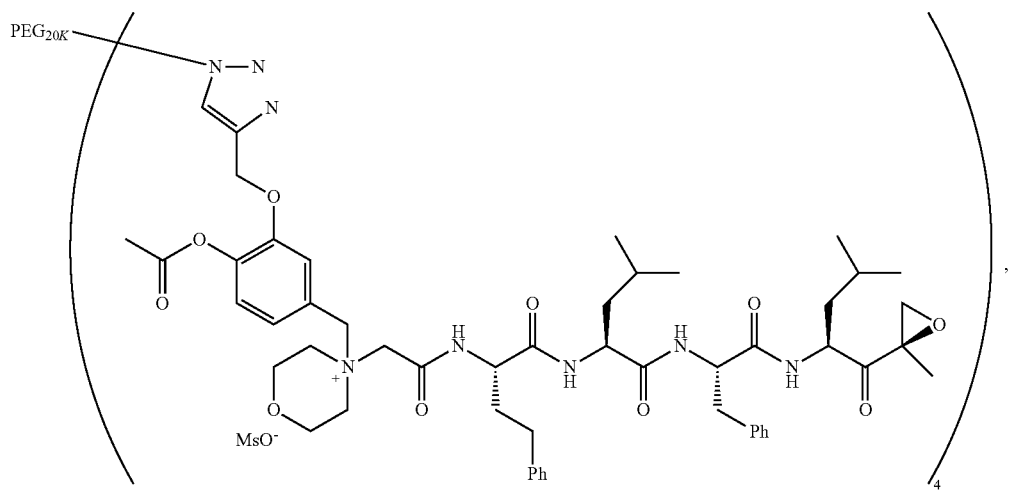
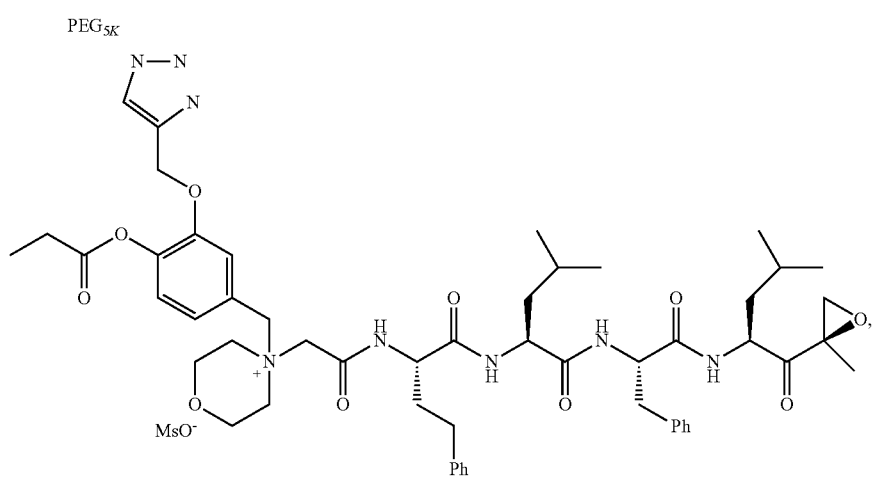
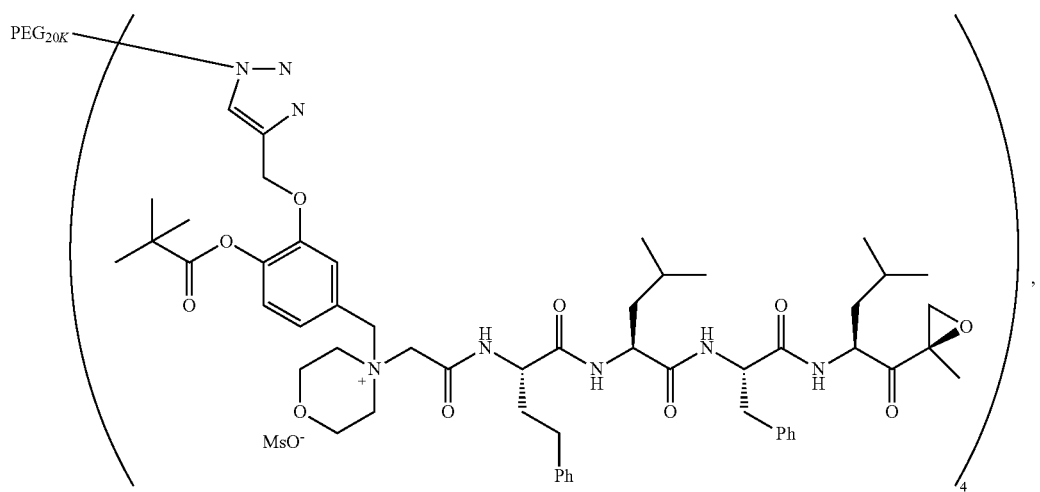

-continued
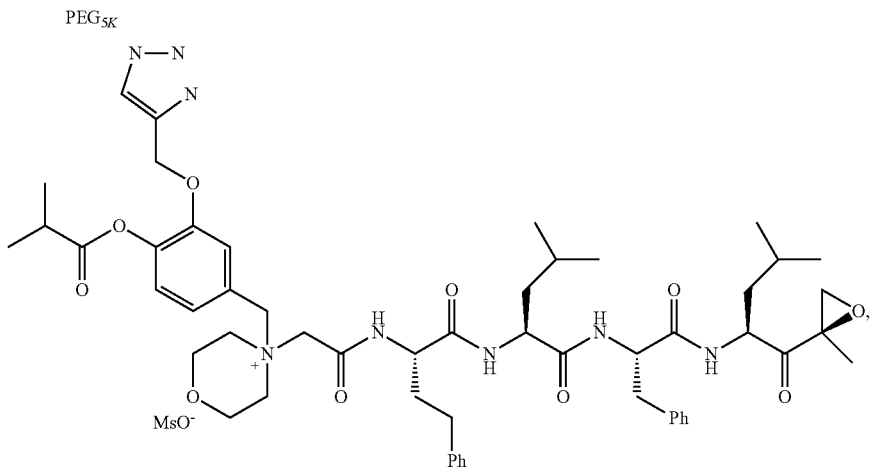
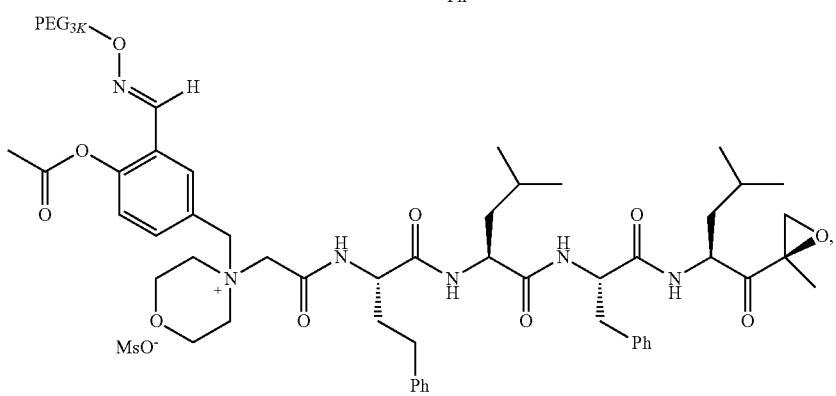
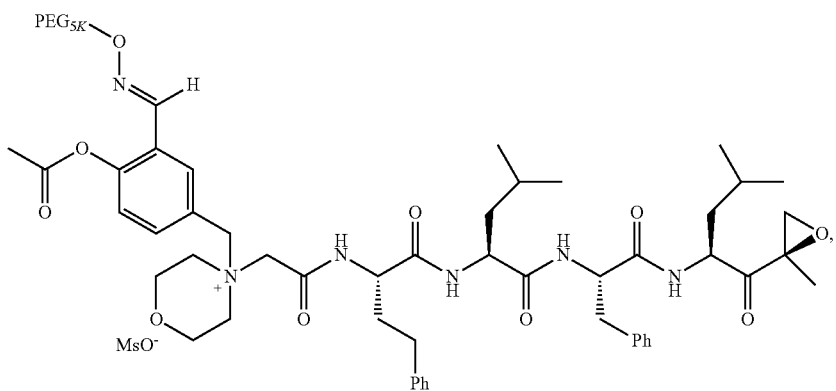
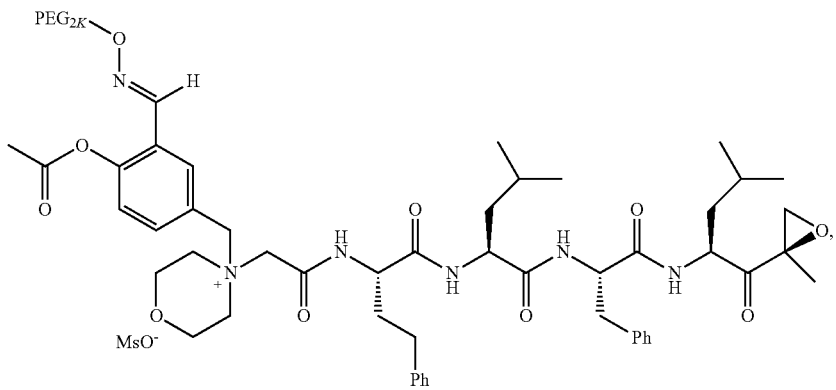

-continued
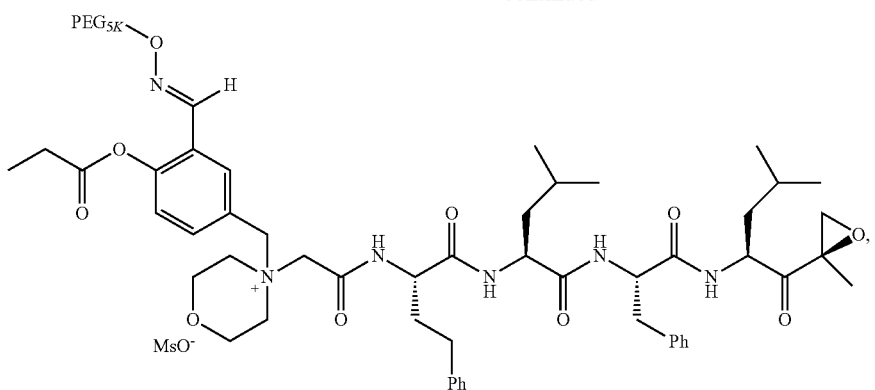
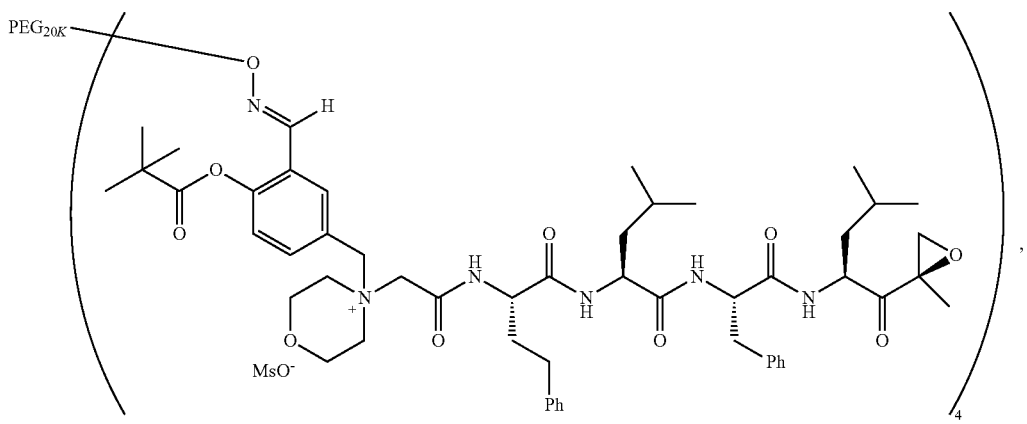
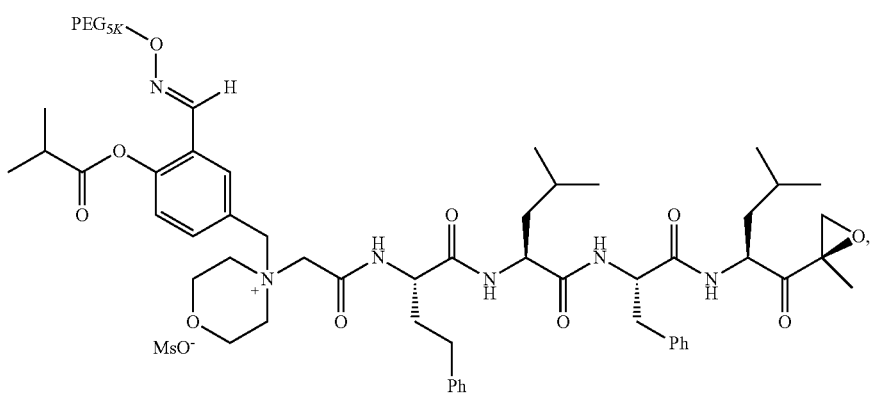
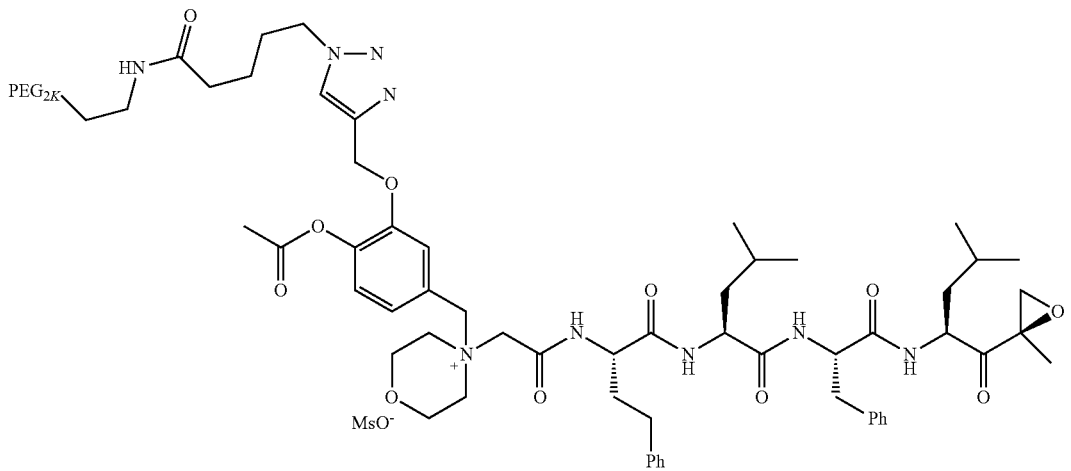
or

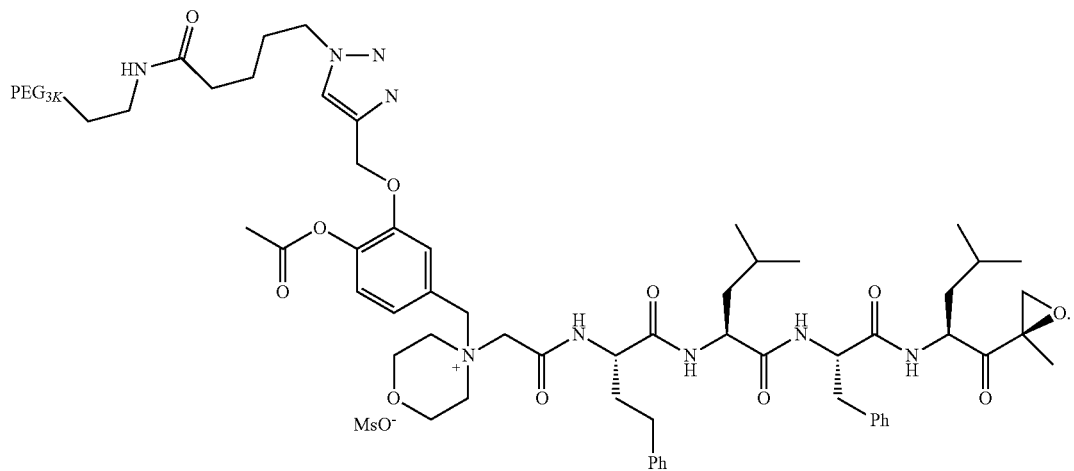
5. The composition of claim 1, wherein the pegylated carfilzomib compound has the structure of
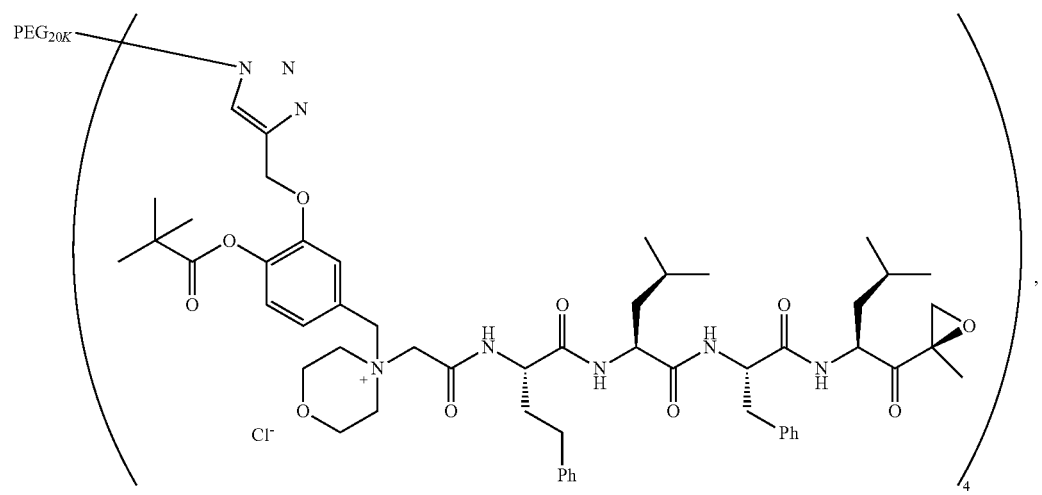
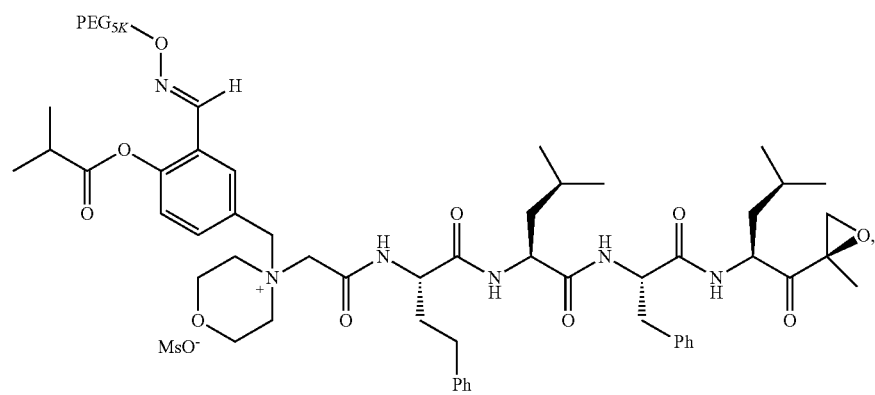

-continued

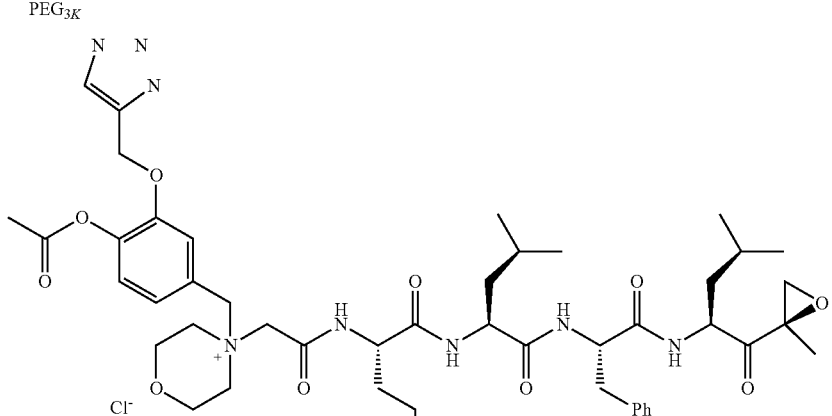

or

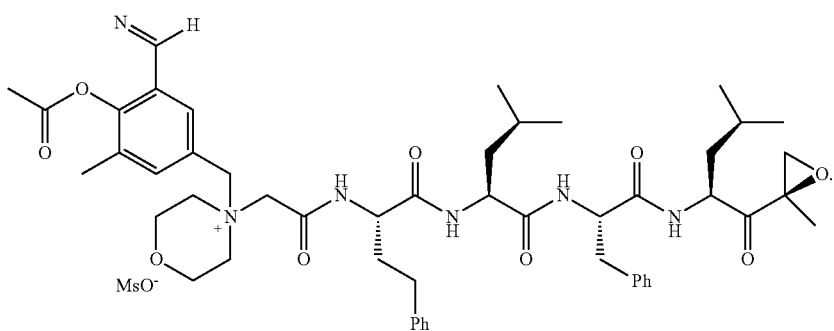

6. The pharmaceutical composition of claim 1, wherein the composition is a frozen formulation, wherein the pH of the formulation is in the range from 5.0 to 8.0.

7. The pharmaceutical composition of claim 1, wherein the composition is a dry lyophilized formulation.

8. The pharmaceutical composition of claim 1 wherein when the composition is dissolved in an amount of water to achieve about 10 mg/mL of the pegylated carfilzomib compound, the pH of the composition is about 5.0.

9. The pharmaceutical composition of claim 1, wherein the pharmaceutical composition comprises the pegylated carfilzomib compound in an amount ranging from 150 mg to 2000 mg.

10. The pharmaceutical composition of claim 1 wherein the composition further comprises hyaluronidase.

11. The pharmaceutical composition of claim 10 wherein the hyaluronidase is present in an amount of about 2000 units/mL.

12. The pharmaceutical composition of claim 1 that does not contain a cyclodextrin.

13. The pharmaceutical composition of claim 7 wherein the lyophilized formulation when dissolved in 1.0 ml of water at room temperature provides a clear solution within a time period of about 3 minutes.

14. The pharmaceutical composition of claim 1 that is administered parenterally by infusion or injection.

15. The pharmaceutical composition of claim 1 that is administered intravenously by infusion or injection.

16. The pharmaceutical composition of claim 1 that is administered by sub-cutaneous injection.

17. A method of treating cancer comprising administering to a patient in need thereof, a therapeutically effective amount of the pharmaceutical composition of claim 1.

18. The method of claim 17 wherein the cancer is multiple myeloma.

19. The method of claim 18 wherein the multiple myeloma is relapsed, refractory or relapsed and refractory multiple myeloma.

20. The method of claim 18 wherein the multiple myeloma is newly diagnosed multiple myeloma.

21. A process of making the pharmaceutical composition of claim 1 for the treatment of multiple myeloma, the process comprising the step of (a) combining a pegylated carfilzomib compound in an amount effective to treat multiple myeloma with 10 mM glutamate, 2% w/v sucrose, and 4% w/v mannitol, or 10 mM glutamate, 2% w/v sucrose, 4% w/v mannitol, and 0.006% w/v polysorbate 80, or 10 mM glutamate, 2% w/v sucrose, 4% w/v mannitol, and 0.05% w/v pluronic F68, or 10 mM glutamate, 2% w/v sucrose, 4% w/v mannitol, 0.5% w/v lysine and 0.006% w/v polysorbate 80, or 10 mM glutamate, 2% w/v sucrose, 4% w/v mannitol, 0.8% w/v lysine and 0.006% w/v polysorbate 80, or 10 mM glutamate, 2% w/v sucrose, 4% w/v mannitol, 0.5% w/v arginine and 0.006% w/v polysorbate 80, or 10 mM glutamate, 2% w/v sucrose, 4% w/v mannitol, 0.8% w/v arginine and 0.006% w/v polysorbate 80; and (b) mixing the combination to provide a clear solution.

* * * * *